United States Patent
Yantasee et al.

(10) Patent No.: US 11,224,573 B2
(45) Date of Patent: Jan. 18, 2022

(54) THERAPEUTIC CONSTRUCTS FOR CO-DELIVERY OF MITOTIC KINASE INHIBITOR AND IMMUNE CHECKPOINT INHIBITOR

(71) Applicants: Oregon Health & Science University, Portland, OR (US); PDX Pharmaceuticals, Inc., Portland, OR (US)

(72) Inventors: Wassana Yantasee, Lake Oswego, OR (US); Moataz Reda, Portland, OR (US); Worapol Ngamcherdtrakul, Portland, OR (US)

(73) Assignees: Oregon Health & Science University, Portland, OR (US); PDX Pharmaceuticals, Inc., Portland, OR (US)

(*) Notice: Subject to any disclaimer, the term of this patent is extended or adjusted under 35 U.S.C. 154(b) by 0 days.

(21) Appl. No.: 17/023,311

(22) Filed: Sep. 16, 2020

(65) Prior Publication Data
US 2021/0030679 A1  Feb. 4, 2021

Related U.S. Application Data

(63) Continuation of application No. PCT/US2020/041852, filed on Jul. 13, 2020.
(Continued)

(51) Int. Cl.
*A61K 9/14* (2006.01)
*A61K 31/519* (2006.01)
(Continued)

(52) U.S. Cl.
CPC .............. *A61K 9/143* (2013.01); *A61K 9/146* (2013.01); *A61K 31/519* (2013.01);
(Continued)

(58) Field of Classification Search
None
See application file for complete search history.

(56) References Cited

U.S. PATENT DOCUMENTS

| 6,406,705 B1 | 6/2002 | Davis et al. |
| 7,045,356 B2 | 5/2006 | Trubetskoy et al. |

(Continued)

FOREIGN PATENT DOCUMENTS

| WO | WO2006076636 A1 | 7/2006 |
| WO | WO2016149378 A1 | 9/2016 |

(Continued)

OTHER PUBLICATIONS

CpG 7909: PF 3512676, PF-3512676, Drugs R.D. 7 (2006) pp. 312-316. (Year: 2006).*

(Continued)

*Primary Examiner* — Dominic Lazaro
(74) *Attorney, Agent, or Firm* — Tanya M. Harding; Lee & Hayes, P.C.

(57) ABSTRACT

Disclosed herein are therapeutic constructs including a delivery particle, at least one mitotic kinase inhibitor, and at least one immune checkpoint inhibitor. Also disclosed are therapeutic constructs including a mitotic kinase inhibitor, an immune checkpoint inhibitor, and a chemical linker. These therapeutic constructs cause cancer death by both therapeutic and immune effects and promote targeted delivery of more therapeutics to the surviving cancer cells in a positive feed-back loop. They enhance therapeutic index of free drugs and can be used intratumorally or systemically. This strategy can treat broad cancer types and is particular useful for cancer without obvious receptors for cancer-targeted delivery of otherwise toxic therapeutics.

51 Claims, 22 Drawing Sheets

Specification includes a Sequence Listing.

Related U.S. Application Data

(60) Provisional application No. 62/873,770, filed on Jul. 12, 2019.

(51) Int. Cl.
  *C07K 16/28* (2006.01)
  *A61K 47/68* (2017.01)
  *A61K 9/00* (2006.01)
  *B82Y 5/00* (2011.01)

(52) U.S. Cl.
  CPC ...... *A61K 47/6803* (2017.08); *A61K 47/6849* (2017.08); *C07K 16/2827* (2013.01); *A61K 9/0019* (2013.01); *B82Y 5/00* (2013.01)

(56) References Cited

U.S. PATENT DOCUMENTS

| | | | |
|---|---|---|---|
| 9,884,026 | B2 | 2/2018 | Fahmy et al. |
| 9,885,082 | B2 | 2/2018 | Hrdlicka |
| 9,976,147 | B2 | 5/2018 | Kortylewski et al. |
| 10,285,950 | B2 | 5/2019 | Frederick et al. |
| 2003/0018002 | A1 | 1/2003 | Sagara |
| 2006/0293396 | A1 | 12/2006 | Bringley et al. |
| 2007/0184068 | A1 | 8/2007 | Renner et al. |
| 2008/0161547 | A1 | 7/2008 | Khvorova et al. |
| 2008/0214436 | A1 | 9/2008 | Yu et al. |
| 2008/0279954 | A1 | 11/2008 | Davis et al. |
| 2009/0110719 | A1 | 4/2009 | Roy et al. |
| 2012/0207795 | A1 | 8/2012 | Zink et al. |
| 2013/0337067 | A1 | 12/2013 | Prakash et al. |
| 2016/0108123 | A1* | 4/2016 | Freeman ............ A61K 39/3955 424/85.2 |
| 2017/0172923 | A1 | 6/2017 | Won |
| 2017/0173169 | A1* | 6/2017 | Yantasee ............... A61K 38/16 |
| 2018/0071387 | A1 | 3/2018 | Coulter et al. |
| 2018/0155189 | A1 | 6/2018 | Zink et al. |
| 2018/0169255 | A1 | 6/2018 | Gao et al. |
| 2018/0200196 | A1 | 7/2018 | Fahmy et al. |
| 2018/0207273 | A1 | 7/2018 | Dranoff et al. |
| 2018/0312536 | A1 | 11/2018 | Sakamuri et al. |
| 2018/0369375 | A1 | 12/2018 | De Waal Malefyt et al. |
| 2019/0008962 | A1 | 1/2019 | Borghi et al. |
| 2019/0048049 | A1 | 2/2019 | Dasseux |
| 2021/0008198 | A1 | 1/2021 | Yantasee et al. |

FOREIGN PATENT DOCUMENTS

| | | | |
|---|---|---|---|
| WO | WO2016189532 | A1 | 12/2016 |
| WO | WO2017040660 | | 3/2017 |
| WO | WO2017120537 | | 7/2017 |
| WO | WO-2017120537 | A1 * | 7/2017 ............... A61P 31/12 |

OTHER PUBLICATIONS

Argyo, et al., "Multifunctional Mesoporous Silica Nanoparticles as a Universal Platform for Drug Delivery," Chem. Mater., vol. 26, No. 1, 2014, pp. 435-451.
Barbe, et al., "Silica Particles: A Novel Drug-Delivery System," Advanced Materials, vol. 16, 2004, pp. 1959-1966.
Bharali, et al., "Organically modified silica nanoparticles: A nonviral vector for in vivo gene delivery and expression in the brain," PNAS, vol. 102, No. 32, 2005, p. 11539-11544.
Butte, et al., "Programmed Death-1 Ligand 1 Interacts Specifically with the B7-1 Costimulatory Molecule to Inhibit T Cell Responses," Immunity, vol. 27, No. 1, 2007, pp. 111-122.
De Braud, et al., "A phase I, dose-escalation study of volasertib combined with nintedanib in advanced solid tumors," Ann. Oncol., vol. 26, No. 11, 2015, pp. 2341-2346.
Ellis, et al., "A Randomized, Open-Label Phase II Trial of Volasertib as Monotherapy and in Combination With Standard-Dose Pemetrexed Compared With Pemetrexed Monotherapy in Second-Line Treatment for Non-Small-Cell Lung Cancer," Clinical Lung Cancer, vol. 16, No. 6, 2015, pp. 457-465.
Esteva, et al., "Immunotherapy and targeted therapy combinations in metastatic breast cancer," Lancet Oncology, vol. 20, No. 3, 2019, pp. e175-e186.
Friedberg, et al., "Phase II Study of Alisertib, a Selective Aurora A Kinase Inhibitor, in Relapsed and Refractory Aggressive B- and T-Cell Non-Hodgkin Lymphomas," Journal of Clinical Oncology, vol. 32, No. 1, 2014, pp. 44-50.
Frost, et al., "Phase I study of the Plk1 inhibitor BI 2536 administered intravenously on three consecutive days in advanced solid tumours," Curr. Oncol., vol. 19, No. 1, 2012, pp. e28-e35.
Gjertsen & Schoffski, "Discovery and development of the Polo-like kinase inhibitor volasertib in cancer therapy," Leukemia, vol. 29, No. 1, 2015, pp. 11-19.
Gorgun, et al., "A novel Aurora-A kinase inhibitor MLN8237 induces cytotoxicity and cell-cycle arrest in multiple myeloma," Blood, vol. 115, No. 25, 2010, pp. 5202-5213.
Gutteridge, et al., "Plk1 Inhibitors in Cancer Therapy: From Laboratory to Clinics," Molecular Cancer Therapeutics, vol. 15, No. 7, 2016, pp. 1427-1435.
Jiao, et al., "PARP Inhibitor Upregulates PD-L1 Expression and Enhances Cancer-Associated Immunosuppression," Clin. Cancer Res., vol. 23, No. 14, 2017, pp. 3711-3720.
Kanwal, et al., "Immunotherapy in Advanced Non-small Cell Lung Cancer Patients: Ushering Chemotherapy Through the Checkpoint Inhibitors?," Cureus, vol. 10, No. 9, 2018, 7 pgs.
Karwacz, et al., "PD-L1 co-stimulation contributes to ligand-induced T cell receptor down-modulation on CD8+ T cells," EMBO Mol. Med., vol. 3, No. 10, 2011, pp. 581-592.
Khair, et al., "Combining Immune Checkpoint Inhibitors: Established and Emerging Targets and Strategies to Improve Outcomes in Melanoma," Frontiers in Immunology, vol. 10, No. 453, 2019, 20 pgs.
Laquerre, et al., "A potent and selective Polo-like kinase 1 (Plk1) inhibitor (GSK461364) induces cell cycle arrest and growth inhibition of cancer cell." 98th AACR Annual Meeting, Los Angeles, CA, Apr. 14-18, 2007; Cancer Res. vol. 67 No. 9 Suppl., Abstract 5389, 2007.
Lin, et al., "A phase I study of two dosing schedules of volasertib (BI 6727), an intravenous polo-like kinase inhibitor, in patients with advanced solid malignancies," Br. J. Cancer, vol. 110, No. 10, 2014, pp. 2434-2440.
Liu, et al., "PLK1, A Potential Target for Cancer Therapy," Translational Oncology, vol. 10, No. 1, 2017, pp. 22-32.
Morry, et al., "Targeted Treatment of Metastatic Breast Cancer by PLK1 siRNA Delivered by an Antioxidant Nanoparticle Platform," Mol. Cancer Ther., vol. 16, No. 4, 2017, pp. 763-772.
Ngamcherdtrakul, et al., "Cationic Polymer Modified Mesoporous Silica Nanoparticles for Targeted siRNA Delivery to HER2+ Breast Cancer," Advanced Functional Materials, vol. 25, No. 18, 2015, pp. 2646-2659.
Ngamcherdtrakul, et al., "Lyophilization and stability of antibody-conjugated mesoporous silica nanoparticle with cationic polymer and PEG for siRNA delivery," Int. J. Nanomedicine, vol. 13, 2018, pp. 4015-4027.
Peng, et al., "Chemotherapy Induces Programmed Cell Death-Ligand 1 Overexpression via the Nuclear Factor-?B to Foster an Immunosuppressive Tumor Microenvironment in Ovarian Cancer," Cancer Research, vol. 75, No. 23, 2015, pp. 5034-5045.
Reynolds, et al., "Severe immune-related adverse effects (irAE) requiring hospital admission in patients treated with immune checkpoint inhibitors for advanced malignancy: Temporal trends and clinical significance.," Journal of Clinical Oncology, vol. 36, Suppl. 15, 2018, p. 3096.
Rudolph, et al., "BI 6727, A Polo-like Kinase Inhibitor with Improved Pharmacokinetic Profile and Broad Antitumor Activity," vol. 15, No. 9, 2009, pp. 3094-3102.
Ruoslahti, "Specialization of tumour vasculature," Nat. Rev. Cancer, vol. 2, 2002, pp. 83-90.
Schmit & Ahmad, "Regulation of mitosis via mitotic kinases: new opportunities for cancer management," Mol. Cancer Ther., vol. 6, No. 7, 2007, pp. 1920-1931.

(56) References Cited

OTHER PUBLICATIONS

Schoffski, et al., "A phase I, dose-escalation study of the novel Polo-like kinase inhibitor volasertib (BI 6727) in patients with advanced solid tumours," European Journal of Cancer, vol. 48, No. 2, 2012, pp. 179-186.
Steegmaier, et al., "BI 2536, a potent and selective inhibitor of polo-like kinase 1, inhibits tumor growth in vivo," Current Biology, vol. 17, No. 4, 2007, pp. 316-322.
Syn, et al., "De-novo and acquired resistance to immune checkpoint targeting," Lancet Oncology, vol. 18, No. 12, 2017, pp. e731-e741.
Topalian, et al., "Immune Checkpoint Blockade: A Common Denominator Approach to Cancer Therapy," Cancer Cell, vol. 27, No. 4, 2015, pp. 450-461.
Zhang, et al., "Cyclin D-CDK4 kinase destabilizes PD-L1 via Cul3SPOP to control cancer immune surveillance," Nature, vol. 553, No. 7686, 2018, pp. 91-95.
Cooper, et al., "CPG 7909 Adjuvant Improves Hepatitis B Virus Vaccine Seroprotection in Antiretroviral-Treated HIV-Infected Adults", AIDS, vol. 19, No. 14, 2005, pp. 1473-1476.
Bringley, et al., "Controlled, simultaneous assembly of polyethylenimine onto nanoparticle silica colloids," Lanqmuir., vol. 22, No. 9, 2006, pp. 4198-4207.
Buchman, et al., "Silica nanoparticles and polyethyleneimine (PEI)—mediated functionalization: a new method of PEI covalent attachment for siRNA delivery applications," Bioconjugate Chemistry, vol. 24, No. 12, 2013, pp. 2076-2087.
Choi & Lee, "Enhanced gene delivery using disulfide-crosslinked low molecular weight polyethylenimine with listeriolysin o-polyethylenimine disulfide conjugate," J. Control. Release, vol. 131, No. 1, 2008, pp. 70-76.
European Office Action dated Feb. 10, 2021 for European Patent Application No. 16765662.8, a counterpart of U.S. Appl. No. 15/429,971, 7 pages.
Gref, et al., "'Stealth' corona-core nanoparticles surface modified by polyethylene glycol (PEG): influences of the corona (PEG chain length and surface density) and of the core composition on phagocytic uptake and plasma protein adsorption," Colloids and Surfaces B Biointerfaces, vol. 18, No. 3-4, 2000, pp. 301-313.
Ha & Breuer, "Mitotic Kinases and p53 Signaling," Biochemistry Research International, vol. 2012, 2012, 14 pages.
Hatakeyama, et al., "Assessment of in vivo siRNA delivery in cancer mouse models," Methods Mol. Biol., vol. 1402, 2016, pp. 189-197.
Haussecker, Dirk, "The Business of RNAi Therapeutics in 2012," Mol. Ther. Nucleic Acids, vol. 2, No. 8, 2012, 12 pages.
He, et al., "Core-shell nanoscale coordination polymers combine chemotherapy and photodynamic therapy to potentiate checkpoint blockade cancer immunotherapy," Nature Communications, vol. 7, 2016, 12 pages.
Heo, et al., "Sequential delivery of an anticancer drug and combined immunomodulatory nanoparticles for efficient chemoimmunotherapy," Int. J. Nanomedicine, vol. 10, 2015, pp. 5981-5993.
Hong, et al., "AZD9150, a next-generation antisense oligonucleotide inhibitor of STAT3 with early evidence of clinical activity in lymphoma and lung cancer," Science Translational Medicine, vol. 7, No. 314, 2015, 13 pages.
Johnston & Grandis, "STAT3 Signaling: Anticancer Strategies and Challenges," Molecular Interventions, vol. 11, No. 1, 2011, pp. 18-26.
Kanasty, et al. "Delivery materials for siRNA therapeutics," Nat. Mater., vol. 12, No. 11, 2013, pp. 967-977.
Kim & Kim, "Bioreducible polymers for gene delivery," React. Funct. Polym., vol. 71, No. 3, 2011, pp. 344-349.
Lee, et al., "Controlled synthesis of PEI-coated gold nanoparticles using reductive catechol chemistry for siRNA delivery," J. Cont. Release, vol. 155, No. 1, 2011, pp. 3-10.

Mao, et al., "Influence of Polyethylene Glycol Chain Length on the Physicochemical and Biological Properties of Poly (ethylene imine)—graft-Poly(ethylene glycol) Block Copolymer/SiRNA Polyplexes," Bioconjugate Chem., vol. 17, No. 5, 2006, pp. 1209-1218.
Meng, et al., "Use of size and a copolymer design feature to improve the biodistribution and the enhanced permeability and retention effect of doxorubicin-loaded mesoporous silica nanoparticles in a murine xenograft tumor model," ACS Nano, vol. 5, No. 5, 2011, pp. 4131-4144.
Mitra, et al., "Novel epithelial cell adhesion molecule antibody conjugated polyethyleneimine-capped gold nanoparticles for enhanced and targeted small interfering RNA delivery to retinoblastoma cells," Mol. Vis., vol. 19, 2013, pp. 1029-1038.
Morry, et al., "Dermal delivery of HSP47 siRNA with NOX4-modulating mesoporous silica-based nanoparticles for treating fibrosis," Biomaterials, vol. 66, 2015, pp. 41-52.
Neu, et al., "Bioreversibly crosslinked polyplexes of PEI and high molecular weight PEG show extended circulation times in vivo," J. Contr. Release, vol. 124, No. 1-2, 2007, pp. 69-80.
Non Final Office Action dated Nov. 27, 2020 for U.S. Appl. No. 16/999,948, "Immunotherapeutic Constructs and Methods of Their Use", Yantasee, 10 pages.
Pan, et al., "Intradermal delivery of STAT3 siRNA to treat melanoma via dissolving microneedles," Scientific Reports, vol. 8, No. 1117, 2018, 11 pages.
Park, et al., "Clustered Magnetite Nanocrystals Cross-Linked with PEI for Efficient siRNA Delivery," Biomacromolecules, vol. 12, No. 2, 2011 pp. 457-465.
Pierce, et al., "In-situ tumor vaccination: Bringing the fight to the tumor," Hum. Vaccin. Immunother., vol. 11, No. 8, 2015, pp. 1901-1909.
Pradhan, et al., "The effect of combined IL10 siRNA and CpG ODN as pathogenmimicking microparticles on Th1/Th2 cytokine balance in dendritic cells and protective immunity against B cell lymphoma," Biomaterials, vol. 35, No. 21, 2014, pp. 5491-5504.
Shao, et al., "Nanoparticle-Based Immunotherapy for Cancer," American Chemical Society, vol. 9, No. 1, 2015, pp. 16-30.
Shen, et al., "Cyclodextrin and polyethylenimine functionalized mesoporous silica nanoparticles for delivery of siRNA cancer therapeutics," Theranostics, vol. 4, No. 5, 2014, pp. 487-497.
Slowing, et al., "Mesoporous Silica Nanoparticles for Drug Delivery and Biosensing Applications," Advanced Functional Materials, vol. 17, No. 8, 2007, pp. 1225-1236.
Tang, et al., "Mesoporous silica nanoparticles: synthesis, biocompatibility and drug delivery," Adv. Mater., vol. 24, No. 12, 2012, pp. 1504-1534.
Tarn, et al., "Mesoporous Silica Nanoparticle Nanocarriers: Biofunctionality and Biocompatibility," Accounts of Chemical Research, vol. 46, No. 3, 2013, pp. 792-801.
Toy and Roy, "Engineering nanoparticles to overcome barriers to immunotherapy," Bioeng. and Translat. Med., vol. 1, No. 1, 2016, pp. 47-62.
Xia, et al., "Polyethyleneimine Coating Enhances the Cellular Uptake of Mesoporous Silica Nanoparticles and Allows Safe Delivery of siRNA and DNA Constructs," ACS Nano, vol. 3, No. 10, 2009, pp. 3273-3286.
Yan, et al., "Combining Immune Checkpoint Inhibitors With Conventional Cancer Therapy," Front. Immunol., vol. 9, No. 1739, 2018, 13 pages.
Zhang, et al., "Differential Expression of Syndecan-1 Mediates Cationic Nanoparticle Toxicity in Undifferentiated versus Differentiated Normal Human Bronchial Epithelial Cells," ACS Nano, vol. 5, No. 4, 2011, pp. 2756-2769.
Zhang, et al., "Synthesis of poly(ethylene glycol) (PEG)—grafted colloidal silica particles with improved stability in aqueous solvents," J Colloid. Interface Sci., vol. 310, No. 2, 2007, pp. 446-455.
PCT Search Report & Written Opinion for Application No. PCT/US2020/041852, dated Oct. 9, 2020, 10 pages.

* cited by examiner

→ 4% antibody loading (BCA)
p-iPLK1-NP

SEQUENCE LISTING

```
<160> NUMBER OF SEQ ID NOS: 3

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct
```

```
<400> SEQUENCE: 1
gugggcgugg uaccaucugu u                                          21

<210> SEQ ID NO 2
<211> LENGTH: 21
<212> TYPE: RNA
<213> ORGANISM: Artificial Sequence
<220> FEATURE:
<223> OTHER INFORMATION: Synthetic Construct

<400> SEQUENCE: 2
uauucauucu ucuugauccg g                                          21

<210> SEQ ID NO 3
<211> LENGTH: 19
<212> TYPE: RNA
<213> ORGANISM: Artificial Sequence
<220> FEATURE:
<223> OTHER INFORMATION: Synthetic Construct

<400> SEQUENCE: 3
uuagucgaca uguaaacca                                             19
```

THERAPEUTIC CONSTRUCTS FOR CO-DELIVERY OF MITOTIC KINASE INHIBITOR AND IMMUNE CHECKPOINT INHIBITOR

CROSS-REFERENCE TO RELATED APPLICATIONS

This application is a continuation of International Application No. PCT/US20/41852, filed Jul. 13, 2020, which in turn claims priority of the earlier filing date of U.S. Provisional Application No. 62/873,770, filed on Jul. 12, 2019. Each of these earlier filed applications is incorporated by reference herein in its entirety.

STATEMENT REGARDING FEDERALLY SPONSORED RESEARCH OR DEVELOPMENT

This invention was made with government support under grant R44CA217534 awarded by the National Institutes of Health. The government has certain rights in the invention.

FIELD OF THE DISCLOSURE

The current disclosure relates to compositions and methods for immunotherapy treatment. Therapeutic constructs are described based on co-delivery of mitotic kinase inhibitor(s) and immune checkpoint inhibitor(s). These therapeutic constructs have greater therapeutic index and/or trigger adaptive anti-cancer immunity better than the free drug counterparts for broad cancer treatment.

BACKGROUND OF THE DISCLOSURE

Immune checkpoint inhibitors, such as antibodies against PD-L1, PD-1, and CTLA-4 have shown promising outcomes in clinics, gaining fast track FDA approval for treating many cancer types. However, while patients who respond to immune checkpoint blockade may show robust and durable responses, only a minority of total patients respond, and even for patients with high PD-L1 expression, response rates remain under 50% (Reck et al., NEJM 375 (19):1823-1833, 2016). Furthermore, many initial responders will develop resistance and ultimately relapse (Jenkins et al., Brit J Canc. 118:9, 2018).

While in general immune checkpoint blockade has less severe and distinct toxicity from chemotherapy, autoimmune disorders caused by immunotherapy is a concern (Tocut et al., Autoimmunity Rev 17(6):610-616, 2018). Systemic distribution of these antibodies can cause aberrant and uncontrolled immune response, leading to immune-related adverse effects (irAEs) (Reynolds et al., J Clin Oncol. 36(16_suppl): 3096, 2018). While generally manageable, discontinuation of treatment due to irAEs have occurred and in some instances irAEs can be fatal.

To improve cancer treatment outcomes, studies have investigated the use chemotherapy in combination with immune checkpoint inhibitors. For instance, one clinical trial has investigated the combination of nab-paclitaxel (abraxane) with PD-L1 antibody (atezolizumab) given as free agents for metastatic TNBC (Schmid et al., N Engl J Med 379(22):2108-2021, 2018). For preclinical studies, nanoparticle for co-delivery of docetaxel and PD-L1 antibody (Xu et al., Inter J Nanomed. 14:17-32, 2018) or doxorubicin and PD-L1 antibody (Emami et al., Mol Pharm 16(3):1184-1199, 2019) have been reported. However, co-delivery of mitotic kinase inhibitor and an immune checkpoint inhibitor has never been reported as free agents or co-delivered on particles or with chemical linkers.

Mitotic kinase inhibitors have single-agent potency to kill cancer cells by inducing cell cycle arrest and apoptosis. Unlike chemotherapeutics which kill any fast dividing cells, mitotic kinase inhibitors are considered targeted therapy, and should be more specific to cancer cells than chemotherapeutics.

Nevertheless, major limitations of current mitotic kinase inhibitors such as PLK1 small molecule inhibitors include low solid tumor bioavailability and toxic side effects to other rapidly dividing cells, particularly to hematopoietic precursor cells (Gjertsen & Schoffski, Leukemia 29(1):11-19, 2015). PLK1 inhibitors need to have long half-lives in order to achieve sufficient tumor bioavailability. This results in longer exposure times with hematopoietic precursor cells in blood and bone marrow, which leads to dose-limiting toxicity of neutropenia (low neutrophils) and thrombocytopenia (low platelets) (de Braud et al., Annals of Oncol./EMSO 26(11):2341-2346, 2015; Schoffski et al., Euro J Canc. 48(2):179-186, 2012; Lin et al., Brit J Canc. 110(10):2434-2440, 2014; Frost et al., Curr Oncol. 19(1):e28-35, 2012). This highlights the need for targeted delivery of the mitotic kinase inhibitors to cancer cells over non-target cells.

Additionally, PLK1 inhibitors can also inhibit other PLK family members PLK2 and PLK3, which may further lead to toxic side effects (Raab et al., Nat. Comm. 2:395, 2011). Of all PLK1 inhibitors, Volasertib (Boehringer Ingelheim) has shown the most promise having reached phase Ill clinical trial but only for acute myeloid leukemia (blood cancer) (Gjertsen & Schoffski, Leukemia 29(1):11-19, 2015), but results in phase Ill trials were not promising perhaps due to insufficient dosages (e.g., limited by toxicity). Inhibition of PLK1 for cancer therapy remains a clinical challenge.

Further, previous studies have elucidated the extensive interplay of PLK1 with many genes that regulate cancer progression and immune evasion (Zitouni et al., Nat Rev Mol Cell Biol 15(7):433-452, 2014; Zhang et al., BMC Cancer 17(1):861, 2017; Liu et al., Translational Oncol. 10(1):22-23, 2017, e-pub 2016; Fu & Wen, Cancers 9(10), 2017), this highlights that monotherapy with PLK1 inhibitors alone may be ineffective. Mitotic kinase inhibitors alone are also quite toxic as shown in clinical trials of various PLK1 inhibitors.

SUMMARY OF THE DISCLOSURE

Described herein is development of new therapeutic constructs based on co-delivery of mitotic kinase inhibitor(s) (or mitotic inhibitor(s)) and checkpoint inhibitor(s). These therapeutic constructs have greater therapeutic index than the free drug counterparts and are useful for broad cancer treatment.

Strategies to improve the response, improve therapeutic efficacy, and manage toxicities of immune checkpoint blockade and mitotic kinase inhibitors are highly warranted for treating cancers. Single agent (namely, therapeutic constructs) delivery of immune checkpoint inhibitors and mitotic kinase inhibitors will co-localize therapeutic effects to achieve synergy, while reducing systemic toxicities of the drugs.

Mitotic inhibitors and mitotic kinase inhibitors have single agent potency to kill cancer cells by inducing cell cycle arrest and apoptosis.

A mechanism by which cancer cells avoid death by mitotic inhibition is to upregulate immune checkpoint to avoid immune-mediated cell killing and hence remain immunologically invisible (FIG. 1A). Thus, by combining mitotic inhibitors with immune checkpoint inhibitors, cells which survive mitotic inhibitors can be attacked by immune cells (i.e. cytotoxic CD8+ T cells) to generate an immune response (FIG. 1B).

Described herein are engineered particles (therapeutic constructs) for co-delivery of at least one mitotic inhibitor or mitotic kinase inhibitor and at least one immune checkpoint inhibitor. Data provided herein illustrate how delivery of a mitotic kinase inhibitor along with an immune checkpoint inhibitor on a therapeutic construct can improve efficacy and reduce toxicity (by reducing doses by 5-fold in the illustrative lung metastasis model).

The immune checkpoint inhibitors on the engineered particles not only enable T cells to attack the cancer cells, but also serve as a homing target agent to the surviving cancer cells.

Data also indicate that not only can the provided therapeutic construct kill cancer cells, but it can also trigger adaptive antitumor response that slow down the development of a distant tumor (e.g., metastasis).

The mitotic kinase inhibitors may be in the class of small molecule inhibitors, antibody-based drugs, or oligonucleotides (e.g., siRNA, miRNA, antisense oligonucleotide).

The therapeutic constructs can be administered locally or intratumorally for instance to readily accessible tumors such as melanoma, head and neck cancer, breast cancer, and lymphoma; or systemically for other cancers such as lung cancer, liver cancer, pancreatic cancer, prostate cancer, brain cancer, kidney cancer, blood cancer, gastric cancer, colon cancer, rare cancer, and metastatic cancer.

Engineered therapeutic constructs can have a diameter in the nanometers or micrometer range, and can be made of any materials (e.g., lipid, organic materials, inorganic materials, polymers, and hybrids or combinations thereof) capable of loading the therapeutic agents/adjuvant cargos, delivering them to the target sites (cancer cells, immune cells, extracellular matrices, etc.), and allowing them to have the desired functions.

Adjuvant can optionally be co-delivered on the same therapeutic construct to boost antitumor T cell repertoire to enhance the therapeutic effect. Mitotic kinase inhibitors will kill cancer cells leading to antigen release, adjuvants will simulate danger signals to activate pattern recognition receptors to stimulate immune cells, and immune checkpoint inhibitor will remove the brakes applied by the tumor cells on immune cells. In this way, the single agent therapeutic can overcome various strategies by which cancer cells evade the immune response to provide sustained cancer cell killing effects.

Optionally, example therapeutic constructs also contain one or more homing agents (antibodies, aptamers, ligands, peptides, etc.) that enable them to be preferentially delivered to and/or taken up by target cancer cells or various immune cell types (e.g., DCs, macrophages, monocytes, T cells).

The herein provided therapeutic constructs may be used alone or in combination with standard therapeutics, including, but not limited to, chemotherapy, surgery, targeted therapies, and radiation therapy.

Alternatively, other targeted therapeutics (e.g., small molecule inhibitors or antibodies targeting other oncoproteins, or medical radioactive isotopes can be loaded directly on/in the therapeutic constructs as a therapeutically active agent.

For local delivery, the therapeutic constructs optionally can be formulated into topical or microneedle formulations.

Provided herein are therapeutic constructs that include: a delivery system; at least one mitotic inhibitor or mitotic kinase inhibitor coupled to or contained within the delivery system; and at least one immune checkpoint inhibitor coupled to or contained within the delivery system. In examples of this embodiment of the therapeutic construct, the delivery system includes a liposome, a lipid-based particle, a polymeric particle, an inorganic or organic nanoparticle or microparticle, or a hybrid thereof. In particular embodiments of the provided therapeutic construct, nanoparticles with a hydrodynamic size of 5 nm to 999 nm (e.g., about 80 nm to about 200 nm, about 90 nm to about 130 nm; or less than 150 nm), as measured in an aqueous solution (such as PBS, Tris buffer, or water) are employed. In yet other examples, the therapeutic constructs are microparticles with a hydrodynamic size of 1 micron to 1000 micron. In some embodiments, the delivery system has a size of about 5 nm to about 200 nm, about 5 nm to about 90 nm, about 5 nm to about 20 nm, about 30 nm to about 100 nm, about 30 nm to about 80 nm, about 30 nm to about 60 nm, about 40 nm to about 80 nm, about 70 nm to about 90 nm, or about 5 nm, about 10 nm, about 20 nm, about 30 nm, about 40 nm, about 50 nm, about 60 nm, about 70 nm, about 80 nm, about 90 nm, or about 100 nm.

In some embodiments, the therapeutic construct further includes an adjuvant. In some embodiments, the therapeutic construct does not include a tumor-specific antigen.

Also provided herein are therapeutic constructs that include an immune checkpoint inhibitor, a mitotic kinase inhibitor, and a chemical linker linking the immune checkpoint inhibitor and the mitotic kinase inhibitors. In some embodiments, the immune checkpoint inhibitor is an oligonucleotide, a polynucleotide, a small molecule inhibitor, or an antibody. In some embodiments, the mitotic kinase inhibitor is an oligonucleotide, a polynucleotide, a small molecule inhibitor, or an antibody. In some embodiments, the therapeutic construct is an antibody-oligonucleotide conjugate, a small molecule-oligonucleotide conjugate, or a small molecule-small molecule conjugate. In some embodiments, the immune checkpoint inhibitor is an antibody (e.g., one that is against PD-L1, PD-1, TIM-3, LAG-3, or CTLA-4). In some embodiments, the mitotic kinase inhibitor is a small molecule inhibitor, such as an inhibitor of PLK1 (e.g., GSK461364, BI2536, Tak960, NMS-P937, volasertib), Chk 1 kinase (e.g., LY2603618, prexasertib, or AZD7762), a RHA helicase A (e.g. YK-4-279), cyclin-dependent kinase 1/2 (e.g., AZ703), Aurora kinase A (e.g., alisertib). In some embodiments, the mitotic kinase inhibitor is an oligonucleotide, such as a siRNA or an antisense oligonucleotide against the mitotic kinase gene (e.g., siRNA against PLK1, such as siPLK1).

Also provided are compositions that include at least one therapeutic construct as described herein. Optionally, such compositions further comprise at least one pharmaceutically acceptable carrier, excipient, or diluent.

Another embodiment is a method of treating cancer, which method includes administering to a subject (such as a human subject) with cancer an effective amount of a provided therapeutic construct, or a composition containing such a therapeutic construct, to reduce one or more symptoms of the cancer.

Also provided are methods of treating a cell exhibiting symptoms of cancer including contacting the cell with a therapeutically effective amount of a provided therapeutic.

Also provided are methods of treating a cell obtained from a subject exhibiting symptoms of cancer including contacting the cell with a therapeutically effective amount of a provided therapeutic construct, or a composition containing such a therapeutic construct.

Also provided are methods of treating a cell obtained from a subject exhibiting symptoms of cancer that include contacting a cell ex vivo with a therapeutically effective amount of a provided therapeutic construct, or a composition containing such a therapeutic construct.

In any of the cell-based embodiments, it is contemplated that the cell in some instances is a cancer cell. In other instances, the cell is not a cancer cell. In various embodiments, the cell is an immune cell. Optionally, in any of the cell-based embodiments, the cell may be from a human subject, or from another mammalian subject.

Yet another embodiment is a method of treating a subject diagnosed as having a hyperproliferative disease or condition, which method includes administering to the subject an effective amount of a composition including at least one of the provided therapeutic constructs.

Also provided are methods of enhancing effect of an anti-cancer therapy in a subject (such as a human subject) in need thereof, including administering to a subject in need thereof: an effective amount of a provided therapeutic construct, or a composition containing such a therapeutic construct; and at least one anti-cancer agent (e.g., a chemotherapeutic agent, targeted therapeutic agent, or an immune checkpoint inhibitor). Optionally, the therapeutic construct or composition and the anti-cancer therapy are administered sequentially or concurrently.

Yet another embodiment is a method of enhancing radiation therapy effect in a subject (such as a human subject) diagnosed as having a neoplasia, including administering to a subject in need thereof: an effective amount of a provided therapeutic construct, or a composition containing such a therapeutic construct; and at least one radiation therapy. Optionally, the therapeutic construct or composition and the radiation therapy are administered sequentially or concurrently.

As used herein, the term "enhancing," in the context of the therapeutic effects of an anti-cancer therapy, refers to an increase in the therapeutic effects of the anti-cancer therapy (e.g., treatment with an anti-cancer agent, radiation therapy, or checkpoint immunotherapy) above those normally obtained when the anti-cancer therapy is administered without the therapeutic constructs of the invention. "An increase in the therapeutic effects" is manifested when there is an acceleration and/or increase in intensity and/or extent of the therapeutic effects obtained with an anti-cancer therapy. It also includes extension of the longevity of therapeutic benefits. It can also manifest where a lower dosage of the anti-cancer therapy is required to obtain the same benefits and/or effects when it is co-administered with the therapeutic constructs provided by the present invention as when a higher dosage of the anti-cancer therapy is administered alone. The enhancing effect preferably, but not necessarily, results in treatment of acute symptoms for which the anti-cancer therapy alone is not effective or is less effective therapeutically. Enhancement is achieved when there is at least a 10% increase (e.g., at least 25%, at least 50%, at least 75%, or at least 100%) in the therapeutic effects when a therapeutic construct of the present invention is co-administered with an anti-cancer therapy compared with administration of the anti-cancer therapy alone.

BRIEF DESCRIPTION OF THE DRAWINGS

(FIG. 1A) Mitotic inhibition (e.g., by PLK1 inhibitor or siRNA) kills cancer and releases antigens, but also increases checkpoint (e.g., PD-L1) expression in the surviving cells, which inhibits anti-cancer immune response to the surviving cells. (FIG. 1B) Combining mitotic inhibitor and immune checkpoint inhibitor (e.g., on a therapeutic construct) leads to synergistic treatment of cancer.

(FIG. 2A) 48-hr PLK1 mRNA knockdown (HPRT used as house-keeping gene) and (FIG. 2B) 72-hr PLK1 protein reduction at 50 nM siRNA dose. (FIG. 2C) 4-day cell viability at 30 nM siRNA dose. (FIG. 2D) Cell cycle arrest increase in G2/M phase in A549 72 hr post treatment. Antibody (cetuximab) conjugated NP was used to deliver the siPLK1 (C-siPLK1-NP) or scrambled siRNA control (C-siSCR-NP) at 50 nM siRNA BI 2536 (a PLK1 inhibitor) was used as a drug benchmark at 10 nM. Data presented as mean±SD from independent duplicates (10,000 events per sample); ****$P<0.0001$ vs. untreat control. Unless specified otherwise, "NP" denotes mesoporous silica nanoparticles coated with cross-linked PEI and PEG, as described in Ngamcherdtrakul et al., Advanced Functional Materials, 25(18):2646-2659, 2015 and U.S. Patent Application Publication No. 2017/0173169.

(FIG. 3A) PLK1 and PD-L1 mRNA expression in A549 (human NSCLC) at 48 hr post treatment with PLK1 siRNA (siPLK1) or scrambled siRNA (siSCR) normalized to HPRT housekeeping gene. Data presented as mean±SD from triplicates; ****$P<0.0001$. (FIG. 3B) PD-L1 surface expression of A549 (FIG. 2B) and LLC-JSP (a mouse NSCLC, FIG. 3C) at 72 hr post treatments assessed by flow cytometry (10,000 events per sample). Mouse siPLK1 seq. GUGGGCGUGGUACCAUCUGUU (SEQ ID NO: 1); Human siPLK1 seq. UAUUCAUUCUUC-UUGAUCCGG (SEQ ID NO: 2).

(FIG. 5A) C57BL/6 mice were injected with 200K LLC-JSP cells in right flank. On day 8 post tumor inoculation, mice were grouped (n=7-8) and received i.p. treatments of control vehicles (PBS and HCl/saline), PLK1 inhibitor volasertib (20 mg/kg), mouse PD-L1 antibody (200 µg per mouse, BioXCell), or combination of PLK1 inhibitor and PD-L1 antibody. Treatments were administered every 5 days for 3 doses. (FIG. 5B) Tumor growth of mice. (FIG. 5C) Kaplan-Meier Survival curve. Data presented as mean±SEM; *$P<0.001$, **$P<0.0001$.

(FIG. 6A) Schematic of synthesis of iPLK1-NP. (FIG. 6B) Hydrodynamic size of NP (with no inhibitor) and iPLK1-NP measured with Zetasizer. (FIG. 6C) Viability of LLC-JSP cells treated with volasertib (in 1% DMSO/PBS), iPLK1-NP (in PBS), or 1% DMSO/PBS for 4 days. Data presented as mean±SD from 4 independent samples; ****$P<0.0001$. (FIG. 6D) PD-L1 surface expression of LLC-JSP cells treated with PBS or iPLK1-NP (42 µg/ml NP, 210 ng/ml volasertib) for 3 days.

(FIG. 7A) Schematic and (FIG. 7B) hydrodynamic size of p-iPLK1-NP containing 4 wt. % of PD-L1 antibody and 0.5 wt. % of PLK1 inhibitor. (FIG. 7C) 5-day cell viability of LLC-JSP cells treated with iPLK1-NP or p-iPLK1-NP. Data presented as mean±SD from 4 independent samples; ns—not significant. PD-L1 surface expression assessed by flow cytometry after LLC-JSP cells were incubated with various treatments as specified for (FIG. 7D) 2 hrs and (FIG. 7E) 2 days. Doses: free PD-L1 antibody (50 µg/ml), iPLK1-NP (NP containing 50 µg/ml volasertib), and p-iPLK1-NP (NP containing 50 µg/ml volasertib and 2 µg/ml PD-L1 antibody). Left of FIGS. 7D and 7E: representative histograms, right: median intensity (RFU). Data presented as mean±SD from independent duplicates (10,000 events per sample); *P<0.05, P<0.01, *P<0.001, ****P<0.0001. Unless specified otherwise, the percent loading is by weight of nanoparticle throughout the application.

(FIG. 8A) 100K LLC-JSP cells were injected in right flank and 40K cells were injected in left flank of C57BL/6 mice. On day 12 post tumor inoculation, mice received intratumoral treatments of saline, p-NP, iPLK1-NP, or p-iPLK1-NP to the right (local) tumor. 0.5 mg NP containing 4 wt. % of PD-L1 antibody and 0.5 wt. % of PLK1 inhibitor in 50 µl per dose for 3 doses total. (FIG. 8B) Local tumor growth. (FIG. 8C) Distant (untreated) tumor growth of individual mice. (FIG. 8D) Kaplan Meier Survival curve. (FIG. 8E) Mice were injected with tumors as described in (FIG. 8A) and received treatments of saline or p-iPLK1-NP. One day after last treatment, tumors were harvested to assess tumor infiltrating lymphocytes (TILs) with flow (50,000 events per sample). Data presented as mean±SEM; *P<0.05, P<0.01, *P<0.001, ****P<0.0001.

(FIG. 9A) C57BL/6 mice were injected with 200K LLC-JSP cells intravenously, which created tumors in the lungs. After 3 days, mice were randomly assigned systemic treatments of saline, free drugs (12.5 µg volasertib and 100 µg PD-L1 antibody), or p-iPLK1-NP (containing 2.5 µg volasertib and 20 µg PD-L1) for a total of 4 doses. (FIG. 9B) Kaplan-Meier Survival curve. *P<0.05, **P<0.01 (Log-rank Mantel-Cox test). (FIG. 9C) Mice weight change post first treatment.

(FIG. 11A) PD-L1 expression of 4T1 cells 4-day post treatment of p-iPLK1-NP. Cells (control and p-iPLK1-NP treated) were harvested and incubated with p-iPLK1-NP tagged with dye-siRNA for 1 hr. (FIG. 11B) Cellular uptake of p-iPLK1-NP. (FIG. 11C) Cell viability of murine cancer cells (LLC-JSP, 4T1, B16-F10) and murine bone marrow-derived dendritic cells (BMDC) treated with p-iPLK1-NP.

FIG. 12A. Western blot showing protein expression of PLK1, PI3Ka, phosphorylated STAT3 (Tyr705), phosphorylated AKT (Ser473), and β-Actin 3 days post treatment (50 nM siRNA) in A549 (left panel) and H460 (right panel) NSCLC cell lines. FIG. 12B shows that NP can also deliver siRNA against PD-L1 (siPDL1) resulting in effective knock down of PD-L1 protein expression (as measured by flow cytometry) in LLC-JSP cells. The cells were treated with NP containing 30 nM siRNA against PD-L1 (siPDL1) or 30 nM scrambled siRNA (siSCR) at 2 wt. % siRNA. At 72 hr post treatment, cells were harvested and assessed for PD-L1 protein expression by flow cytometry. RFU=Relative fluorescence units.

(FIG. 14A) Synthesis scheme of PD-L1-antibody alisertib conjugate (ADC). (FIG. 14B) Treatment effect of ADC versus free alisertib of equivalent dose on viability of LLC-JSP cells (2-days). Free alisertib was dissolved in DMSO before use. (FIG. 14C) Effect of PD-L1 on the viability of LLC-JSP cells.

REFERENCE TO SEQUENCE LISTING

Figure 1A:
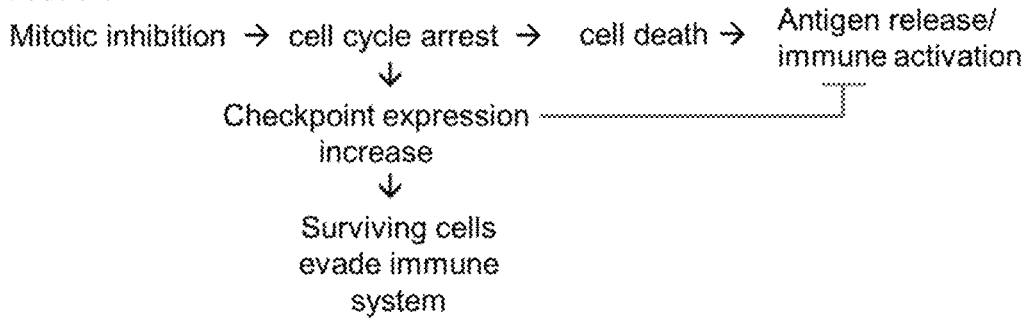
FIGS. 1A-1B. Central hypothesis for therapeutic constructs' activities.
Figure 1B:
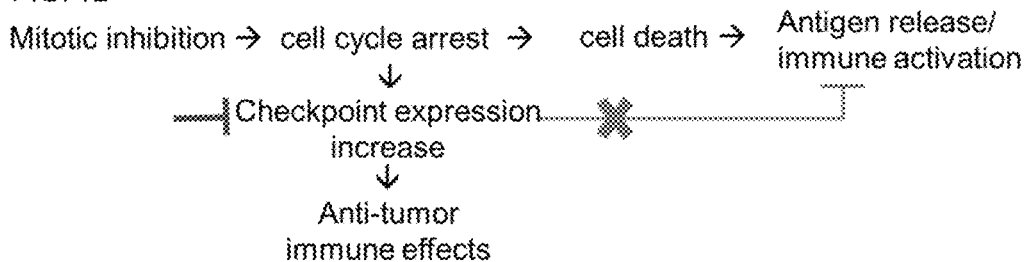

The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate. A computer readable text file, entitled "2CW2113.txt" created on or about Jul. 13, 2020, with a file size of 1 KB, contains the sequence listing for this application and is hereby incorporated by reference in its entirety.

```
SEQ ID NO: 1 is a Mouse siPLK1 sequence:
GUGGGCGUGGUACCAUCUGUU

SEQ ID NO: 2 is a Human siPLK1 sequence:
UAUUCAUUCUUCUUGAUCCGG
```

-continued

SEQ ID NO: 3 is a scrambled siSCR sequence:
UUAGUCGACAUGUAAACCA

DETAILED DESCRIPTION

The herein described therapeutic approach for cancer treatment utilizes engineered particles or chemical linkers for co-delivery of mitotic kinase inhibitors and immune checkpoint inhibitors to create therapeutic constructs that localize both classes of drugs in the same cells for cancer therapy.

Upon intratumoral or systemic administration of a provided therapeutic construct to cancer cells, the mitotic kinase inhibitors will put cancer to cell cycle arrest, leading to programmed cell death, and increased immune checkpoint expression (e.g., PD-L1) of the surviving cancer cells. Therefore, immune checkpoint inhibitors (e.g., antibodies against PD-L1) will enhance targeted delivery of the construct to the surviving cells as well as enable cytotoxic T cells to attack the cancer.

Since mitotic kinase inhibitors can upregulate PD-L1 receptors, this strategy can treat broad cancer types and is particular useful for cancer without obvious receptors for targeted delivery of otherwise toxic therapeutics such as mitotic kinase inhibitors.

Death of cancer cells also releases tumor antigens and together with checkpoint inhibition can trigger adaptive immunity to attack cancer or prevent cancer spread or relapse. Optionally, an adjuvant can be added to the therapeutic construct to increase the antitumor immune response.

The invention utilizes new discovery cancer biology and immunology, and engineered particles to create new drug candidates to increase efficacy while reduce toxicity compared to free drug counterparts.

In certain embodiments, the delivery vehicle includes a MSNP core (e.g., ~50 nm) for drug loading, coated with a bioreducible cross-linked cationic polymer, e.g., polyethylenimine (PEI) for oligo loading and endosomal escape; and a stabilizer, e.g., polyethylene glycol (PEG), which prevents nanoparticle aggregation, protects oligo cargos from degradation by blood enzymes (Ngamcherdtrakul et al., *Advanced Functional Materials*, 25(18):2646-2659, 2015), and shields the charge of PEI, enhancing safety. Oligo (siRNA and/or CpG) is loaded last on the construct with a few minutes (e.g., 5 minutes) mixing in PBS at room temperature; it electrostatically binds to PEI in an oligo sequence-independent manner and is protected under the PEG layer from enzymatic degradation (Ngamcherdtrakul et al., *Advanced Functional Materials*, 25(18):2646-2659, 2015). The resulting nanoparticle (NP) was highly optimized for siRNA delivery efficacy in terms of MSNP sizes, PEI and PEG molecular weights and compositions, PEI crosslinking conditions (to enhance buffering capacity and lower charge), oligo and (optionally) antibody loadings (Ngamcherdtrakul et al., *Advanced Functional Materials*, 25(18):2646-2659, 2015). This embodiment of the siRNA-NP has a rigid MSNP core size (by TEM) of 50 nm and hydrodynamic size (NP with polymer coatings) of 100 nm with a narrow size distribution. It consists of 13.5 wt. % PEI, 18.2 wt. % PEG, and can load 2-4 wt. % siRNA or up to 10 wt. % of CpG oligo. Drug (e.g., taxane) can be loaded in the MSNP core or on the polymers at 0.5-3 wt. %. All values in this paragraph are by weight of the nanoparticle. See also US Patent Publication 2017/0173169.

In certain embodiments, the immune checkpoint inhibitor is an oligonucleotide, a polynucleotide, a small molecule inhibitor, or an antibody. In some embodiments, the mitotic kinase inhibitor is an oligonucleotide, a polynucleotide, a small molecule inhibitor, or an antibody. In some embodiments, the therapeutic construct is, or an antibody-oligonucleotide conjugate (Wiener, J. et al. Scientific Reports, 10, 1457, 2020), a small molecule-oligonucleotide conjugate (Winkler J., Therapeutic delivery, 4(7), 791-809, 2013), or a small molecule-small molecule conjugate.

Provided herein are therapeutic constructs that include: a delivery system; at least one mitotic inhibitor or mitotic kinase inhibitor coupled to or contained within the delivery system; and at least one immune checkpoint inhibitor coupled to or contained within the delivery system. In examples of this embodiment of the therapeutic construct, the delivery system includes a liposome, a lipid-based particle, a polymeric particle, an inorganic or organic nanoparticle or microparticle, or a hybrid thereof. For instance, in various examples the delivery vehicle includes one or more of fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, calcium phosphate, dendrimers, microparticles, quantum dots, superparamagnetic nanoparticles, nanorods, cellulose nanoparticles, silicon, silica and polymer micro- and nano-spheres, silica-shells, biodegradable PLGA micro- and nano-spheres, gold nanoparticles, cerium oxide particles, zinc oxide particles, silver nanoparticles, carbon nanoparticles, iron nanoparticles, and/or modified micelles.

In examples of the provided therapeutic construct embodiments, the mitotic kinase inhibitor and/or immune checkpoint inhibitor includes an oligonucleotide (e.g., a siRNA or an antisense oligonucleotide), a polynucleotide, a small molecule inhibitor, or an antibody.

In examples of the therapeutic construct, the mitotic kinase inhibitor includes an inhibitor of at least one of a polo-like kinase (PLK), an Aurora kinase, cyclin-dependent kinase (CDK)1, CDK2, HASPIN, monopolar spindle 1 kinase (Mps1), or a NimA-related kinase (NEK). In various embodiments, the mitotic kinase inhibitor includes one or more of GSK461364, B12536, Tak960, NMS-P937, B16727 (volasertib), Chk 1 Kinase Inhibitor LY2603618, prexasertib, AZD7762, AU14022, YK-4-279, or AZ703.

In various embodiments, the mitotic inhibitor includes one or more of etoposide, vinorelbine, mitoxantrone, doxorubicin, estramustine, carboplatin, vinblastine, docetaxel, paclitaxel, and cabazitaxel.

In various embodiments, the immune checkpoint inhibitor includes a siRNA, inhibitor, or antibody against one or more of PD-L1, PD-1, TIM-3, LAG-3, or CTLA-4. By way of example, the therapeutic agent is an immune checkpoint inhibitor selected from an antibody against PD-L1, PD-1, or CTLA-4. In yet more examples, the immune checkpoint inhibitor includes at least one of: nivolumab, pembrolizumab, ipilimumab, tremelimumab, atezolizumab, avelumab, durvalumab, cemiplimab, pidilizumab, or spartalizumab (PDR001).

The therapeutic constructs provided herein may optionally further include an adjuvant. It is specifically contemplated that example adjuvants used with the provided therapeutic constructs exhibit immunostimulatory activity. By way of example, an adjuvant useful in embodiments of the provided therapeutic constructs includes one or more of a CpG oligonucleotide, a DNA TLR agonist containing a CpG sequence, a non-CpG DNA TLR agonist, an RNA TLR agonist, an aluminum salt, an anti-CD40 antibody, a fusion protein, a cytokine, a small molecule TLR agonist, an oil- or surfactant-based adjuvant, a lipopolysaccharide, a plant extract, or a derivative thereof. In specific examples, the adjuvant compound includes a CpG oligonucleotide, imiquimod, resiquimod, gardiquimod, poly IC, poly ICLC, dSLIM, or EnanDIM.

In some embodiments, the therapeutic construct does not include a tumor-specific antigen.

Also provided are compositions that include at least one therapeutic construct as described herein. Optionally, such compositions further comprise at least one pharmaceutically acceptable carrier, excipient, or diluent.

Another embodiment is a method of treating cancer, which method includes administering to a subject (such as a human subject) with cancer an effective amount of a provided therapeutic construct, or a composition containing such a therapeutic construct, to reduce one or more symptoms of the cancer.

Also provided are methods of treating a cell exhibiting symptoms of cancer including contacting the cell with a therapeutically effective amount of a provided therapeutic.

Also provided are methods of treating a cell obtained from a subject exhibiting symptoms of cancer including contacting the cell with a therapeutically effective amount of a provided therapeutic construct, or a composition containing such a therapeutic construct.

Also provided are methods that include contacting a cell ex vivo with a therapeutically effective amount of a provided therapeutic construct, or a composition containing such a therapeutic construct.

In any of the cell-based embodiments, it is contemplated that the cell in some instances is a cancer cell. In other instances, the cell is not a cancer cell. In various embodiments, the cell is an immune cell. Optionally, in any of the cell-based embodiments, the call may be from a human subject, or from another mammalian subject.

Yet another embodiment is a method of treating a subject diagnosed as having a hyperproliferative disease or condition, which method includes administering to the subject an effective amount of a composition including at least one of the provided therapeutic constructs. In various examples of this embodiment, the hyperproliferative disease includes one or more of cancer, precancer, or cancer metastasis. In examples of these methods, the hyperproliferative disease includes one or more of melanoma, lung cancer, breast cancer, pancreatic cancer, brain cancer, prostate cancer, head and neck cancer, kidney cancer, colorectal cancer, lymphoma, colon cancer, or liver cancer.

In any of the provided methods of treating a subject, it is contemplated that administration can be by a variety of methods. For instance, in examples of treatment methods, administering includes one or more of: injection to or at a tumor in the subject; infusion locally to or at a tumor in the subject; systemic injection in the subject; systemic infusion in the subject; or topical application to the subject. In other examples, administering includes microneedle application.

Also provided are methods of enhancing effect of an anti-cancer therapy in a subject (such as a human subject) in need thereof, including administering to a subject in need thereof: an effective amount of a provided therapeutic construct, or a composition containing such a therapeutic construct; and at least one anti-cancer agent (e.g., a chemotherapeutic agent, a targeted therapeutic agent, or an immune checkpoint inhibitors). Optionally, the therapeutic construct or composition and the anti-cancer therapy are administered sequentially or concurrently.

Yet another embodiment is a method of enhancing radiation therapy effect in a subject (such as a human subject) diagnosed as having a neoplasia, including administering to a subject in need thereof: an effective amount of a provided therapeutic construct, or a composition containing such a therapeutic construct; and at least one radiation therapy. Optionally, the therapeutic construct or composition and the radiation therapy are administered sequentially or concurrently.

Also provided herein is a kit including a therapeutic construct described herein and at least one anti-cancer agent. In some embodiments, the anti-cancer agent is a chemotherapeutic agent, a targeted therapeutic agent, or an immune check point inhibitor.

Aspects of the disclosure are now described with additional detail and options to support the teachings of the disclosure, as follows: (I) Therapeutic Constructs; (II) Mitotic Kinases and Inhibitors Thereof; (Ill) Immune Checkpoint Inhibitors; (IV) Optional Additional Component(s); (V) Delivery Systems; (VI) Antibodies; (VII) Pharmaceutical Compositions and Administration Formulations; (VIII) Exemplary Methods of Use; (IX) Kits; (X) Exemplary Embodiments; and (XI) Examples.

(I) THERAPEUTIC CONSTRUCTS

Described herein is a new class of therapeutics (generally, "therapeutic constructs") that include an engineered particle which co-delivers at least two active agents, which include at least one mitotic kinase inhibitor and at least one immune checkpoint inhibitor, to cancer cells. Also disclosed herein are therapeutic constructs that include an immune checkpoint inhibitor, a mitotic kinase inhibitor, and a chemical linker connecting the two (an antibody-drug conjugate), e.g., such as any of those described herein. The ratio of active agents (e.g., mitotic kinase inhibitor to immune checkpoint inhibitor or immune checkpoint inhibitor to mitotic kinase inhibitor) can be, e.g., about 1-20 (e.g., about 2-8, about 4-6, about 2, about 4, or about 6). The mitotic kinase inhibitor can be present at 0.01 wt. % to 99.9 wt. % of the therapeutic construct (e.g., 0.01 to 1 wt. %, 1 to 5 wt. %, 1 to 10 wt. %, 1 to 20 wt. %, 10 to 30 wt. %, 10 to 40 wt. %, 10 to 50 wt. %, 25 to 75 wt. %, 40 to 60 wt. %, 50 to 75 wt. %, 50 to 80 wt. %, 75 to 90 wt. %, 75 to 95 wt. %, or 75 to 99.9), and the immune checkpoint inhibitor can be present at 0.01 wt. % to 99.9 wt. % (e.g., 0.01 to 1 wt. %, 1 to 5 wt. %, 1 to 10 wt. %, 1 to 20 wt. %, 10 to 30 wt. %, 10 to 40 wt. %, 10 to 50 wt. %, 25 to 75 wt. %, 40 to 60 wt. %, 50 to 75 wt. %, 50 to 80 wt. %, 75 to 90 wt. %, 75 to 95 wt. %, or 75 to 99.9 wt. %). These therapeutic constructs reduce the doses required to achieve the efficacy by, e.g., about five-fold, allowing the drugs to be given together without reaching their dose-limiting toxicity. They create adaptive immunity that enhances tumor inhibition and development at local (treated) and distant (non-treated) sites (e.g., metastasis), and survival of the treated subject. Once treated with the therapeutic constructs, cancer undergoes programmed cell death, while the surviving cells overexpress immune checkpoint molecules such as PD-L1. This enables more targeted delivery of the constructs to the remaining cancers, that otherwise may not have significant expression of receptors for targeted delivery, in a feed-forward manner. The therapeutic constructs are also applicable to broad cancer types since mitotic kinases are found in all cancers, which would overexpress immune checkpoint molecules such as PD-L1 upon mitotic kinase inhibition.

In some examples, the chemical linker may include one or more a hydrazine; a disulfide; N-succinimidyl-4-(2-pyridyldithio)butanoate; N-succinimidyl-4-(2-pyridyldithio)-2-sulfo butanoate; perfluorophenyl 3-(pyridin-2-yldisulfanyl) propanoate; 2,5-dioxopyrrolidin-1-yl 3-methyl-3-(pyridin-2-yldisulfanyl)butanoate; Gly-Phe-Leu-Gly; Ala-Leu-Ala-Leu; Val-Cit; Phe-Lys; Val-Ala; Ala-Phe-Lys; Phe-Lys; (Gly)n, wherein n is 1-20; a β-glucuronide linker; maleimidocaproyl; N-(maleimidomethyl)cyclohexane-1-carboxylate; 4-(4-acetylphenoxy)butanoic acid; dibromomaleimide; para-aminobenzoic acid; 4-nitrophenol; acetic acid; formic acid; 4-maleimidobutyric acid N-succinimidyl ester; N-(4-maleimidobutyryloxy)succinimide; N-(6-maleimidocaproyloxy)succinimide; 3-maleimidopropionic acid N-succinimidyl ester; N-(3-maleimidopropionyloxy)succinimide; 5-maleimidovalericacid-NHS; linear, branched, or multi-arm polyethylene glycol having a molecular weight of 100-10000 Da; propargyl-N-hydroxysuccinimidyl ester; pyrophosphate; succimimidyl-4-azidobutyrate; 4-azidobenzoic acid N-hydroxysuccinimide ester; tert-butyl 1-(4-formylphenyl)-1-oxo-5,8,11-trioxa-2-azatridecan-13-oate; or a residue thereof. In some embodiments, the chemical linker includes N-(maleimidomethyl)cyclohexane-1-carboxylate or a residue thereof (e.g., sulfosuccinimidyl 4-(N-maleimidomethyl)cyclohexane-1-carboxylate). In some embodiments, the chemical linker includes a polyethyleneglycol (e.g. a linear polyethyleneglycol) having a molecular weight of 100-10000 Da or a residue thereof.

This strategy will have many key features; they are efficacious, safe due to lower doses needed (vs. free drug counterparts), durable because they train and harness body immune cells to attack cancer with memory effects, applicable to many types of cancer, and can be given both locally for easily accessible tumors and systemically for deeper tumors and metastatic tumors.

It will be understood that the amount of each component in a therapeutic construct (for instance, a mitotic inhibitor, a mitotic kinase inhibitor, an immune checkpoint inhibitor, the delivery vehicle, or any component of the delivery vehicle) may vary, depending in the embodiment. By way of example, any individual component may make up 0.001% to 80% by weight, 0.01% to 75% by weight, 0.5 to 50% by weight, 0.5 to 10% by weight, 0.5 to 5% by weight, 1 to 10% by weight, or 2 to 4% by weight, of the therapeutic construct.

(II) MITOTIC KINASES AND INHIBITORS THEREOF

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment, and cytokinesis (Dutertre et al. *Oncogene* 21: 6175, 2002; Berdnik et al. *Curr. Biol.* 12: 640, 2002). Overexpression and/or amplification of Aurora kinases have been linked to oncogenesis in several tumor types including those of colon and breast (Warner et al. *Mol. Cancer Ther.* 2: 589, 2003; Bischoff et al. *EMBO* 17: 3062, 1998; Sen et al. *Cancer Res.* 94: 1320, 2002). Moreover, Aurora kinase inhibition in tumor cells results in mitotic arrest and apoptosis, suggesting that these kinases are important targets for cancer therapy (Ditchfield, *J. Cell Biol.* 161: 267, 2003; Harrington et al. *Nat Med* 10(3): 262-267, 2004).

Mitotic Kinases:

In particular embodiments, mitotic kinases include kinases in the Aurora family of serine/threonine kinases essential for cell proliferation (Bischoff & Plowman, *Trends in Cell Biology* 9: 454-459, 1999; Giet & Prigent, *J Cell Science* 112: 3591-3601, 1999; Nigg, *Nat. Rev. Mol. Cell Biol.* 2: 21-32, 2001; Adams et al., *Trends in Cell Biology* 11: 49-54, 2001). Since its discovery in 1997 the mammalian Aurora kinase family has been closely linked to tumorigenesis. The most compelling evidence for this is that overexpression of Aurora-A transforms rodent fibroblasts (Bischoff et al., *EMBO J.* 17: 3052-3065, 1998). Inhibitors of the Aurora kinase family therefore have the potential to block growth of all tumor types.

The three known mammalian family members, Aurora-A ("1"), B ("2") and C ("3"), are highly homologous proteins responsible for chromosome segregation, mitotic spindle function and cytokinesis. They are highly conserved in the C-terminal region, where the kinase domain is located, and show sequence differences in the N-terminal domain (*Nat. Rev. Cancer*, 5: 42-49, 2005). Aurora expression is low or undetectable in resting cells, with expression and activity peaking during the G2 and mitotic phases in cycling cells. In mammalian cells proposed substrates for Aurora include histone H3, a protein involved in chromosome condensation, and CENP-A, myosin II regulatory light chain, protein phosphatase 1, TPX2, all of which are required for cell division.

Aurora B is expressed between the late G2-phase and telophase. It is located in the inner centromere region and in the spindle middle zone. It regulates the orientation of the chromosomes at the metaphase plate and corrects wrong kinetochore-microtubule interactions. It phosphorylates histone H3, which allows the histone to interact with the DNA. This is important for the following chromosome condensation. Aurora C shows high sequence homologies with Aurora B and has functions in the meiosis.

As used herein, the term "Aurora A kinase" refers to a serine/threonine kinase involved in mitotic progression. Aurora A kinase is also known as AIK, ARK1, AURA, BTAK, STK6, STK7, STK15, AURORA2, MGC34538, and AURKA. A variety of cellular proteins that play a role in cell division are substrates for phosphorylation by the Aurora A kinase enzyme, including, TPX-2, XIEg5 (in *Xenopus*), and D-TACC (in *Drosophila*). The Aurora A kinase enzyme is also itself a substrate for autophosphorylation, e.g., at Thr288. In some instances, the Aurora A kinase is a human Aurora A kinase.

In particular embodiments, mitotic kinases include Polo-like kinases ("PLKs"). PLKs, including polo-like kinase 1 ("PLK1"), polo-like kinase 2 ("PLK2"), polo-like kinase 3 ("PLK3") and polo-like kinase 4 ("PLK4"), are involved in the formation and changes in the mitotic spindle and in the activation of CDK/cyclin complexes during mitosis (Strebhardt & Ullrich, *Nature Reviews Cancer* 6(4): 321, 2006). Plks are overexpressed in tumors, and the overexpression is associated with a poor prognosis and lower overall survival. Therefore, inhibitors of PLKs have been developed as cancer drug therapies.

In particular embodiments, mitotic kinases include cyclin-dependent protein kinases (CDKs). CDKs are regulators of the timing and coordination of eukaryotic cell cycle events (Norbury & Nurse, *Annu. Rev. Biochem.* 61: 441-470, 1992; Sher, *Science* 274: 1672-1677, 1996). As such, CDKs, their regulators, and their substrates are the targets of genetic alterations in many human cancers (Kamb et al., *Science* 264: 436-440, 1994; Nobori et al., *Nature* 368: 753-756, 1994; Spruck et al., *Nature* 370: 183-184, 1994; Hunter & Pines, *Cell* 66: 1071-1074, 1991; Keyomarsi & Pardee, *Proc. Natl. Acad. Sci. U.S.A.* 90: 1112-1116, 1993; Wang, *Nature* 369: 669-671, 1994). Members of the cyclin dependent kinase family include Cdk2 and Cdk4. Both are active in the G1 phase of cell cycle and regulate entry into the G1/S phase transition. In one pathway, these kinases regulate the phosphorylation of the retinoblastoma protein. Substrate phosphorylation releases the E2F transcription factor which in turn regulates the expression of genes required for S phase entry. Inhibition of these kinases, therefore, blocks cell entry into the S phase and downstream proliferative events.

In particular embodiments, mitotic kinases include monopolar spindle 1 (MPS1) kinase. MPS1 kinase, also known as TTK, is a dual serine/threonine kinase that controls chromosome alignment and influences the stability of the kinetochore-microtubule interaction as a key regulator of the spindle assembly checkpoint (SAC). SAC is essential for proper chromosomal alignment and segregation. MPS1 is expressed only in proliferating cells and is activated upon phosphorylation during mitosis, where it is required for proper kinetochore recruitment of essential SAC proteins such as Mad1 (mitotic arrest deficient protein 1) and Mad2 (mitotic arrest deficient protein 2). MPS1 is also overexpressed in a wide range of human tumors and is necessary for tumor cell proliferation.

In particular embodiments, mitotic kinases include Nek ((never in mitosis gene a)-related kinase) 2. Nek2 is a serine/threonine kinase that localizes to the centrosome and regulates spindle pole organization and separation through phosphorylation of substrates including C-Nap1 (nucleosome assembly protein-1), rootletin, and Nlp (ninein-like protein). In addition to its centrosomal role, Nek2 has also been implicated in chromatin condensation and spindle checkpoint control. Nek2 expression and activity are tightly regulated in a cell cycle dependent manner. Expression levels are low in G1 and increased in S/G2. Nek2 is abnormally expressed in cancer cells.

In particular embodiments, mitotic kinases include Wee1 kinase. Wee1 kinase is a mitotic inhibitor and maintains G2-cell-cycle checkpoint arrest for pre-mitotic DNA repair. Wee1 is overexpressed in cancers such as advanced hepatocellular carcinoma, breast cancer, colon cancer, lung carcinoma, seminoma, and glioblastoma, and its expression correlated with patient survival in mantle cell lymphoma.

One of ordinary skill in the art will understand how to access representative sequences for mitotic kinases, which are readily available in public sequence databases. The following table provides sample sequence information:

| Gene Abbreviation | Full gene name | Representative GenBank Accession #s |
|---|---|---|
| PLK1 | Polo-like kinase 1 | NM_005030.5 |
| PLK2 | Polo-like kinase 2 | NM_001252226.1; NM_006622.3 |
| PLK3 | Polo-like kinase 3 | NM_004073.3; XR_246234.4 |
| PLK4 | Polo-like kinase 4 | NM_001190799.1; NM_001190801.1 NM_014264.4; XM_005262701.2 XM_017007662.1; XM_017007663.1 |
| CDK1 | Cyclin-dependent kinase 1 | NM_001170406.1; NM_001170407.1 NM_001320918.1; NM_001786.4 NM_033379.4; XM_005270303.3 |
| CDK2 | Cyclin-dependent kinase 2 | NM_001290230.1; NM_001798.4 NM_052827.3; XM_011537732.1 |
| CHK1 | Checkpoint kinase 1 | NM_001114121.2; NM_001114122.2 NM_001244846.1; NM_001274.5 NM_001330427.1; NM_001330428.1 XM_011542560.2; XM_011542562.2 XM_017017146.1; NR_045204.1 NR_045205.1 |
| CHK2 | Checkpoint kinase 2 | NM_001005735.1; NM_001257387.1 NM_001349956.1; NM_007194.3 NM_145862.2; XM_006724114.3 XM_006724116.2; XM_011529839.2 XM_011529840.2; XM_011529841.1 XM_011529842.2; XM_011529844.2 XM_011529845.2; XM_017028560.1 XM_017028561.1; XR_937805.2 XR_937806.2; XR_937807.2 |
| BUB1 | budding uninhibited by benzimidazole 1 | NM_001278616.1; NM_001278617.1 NM_004336.4; XR_923001.2 |
| BUBR1 | budding uninhibited by benzimidazole-related 1 | NM_001211.5 |
| MPS1 | Monopolar spindle 1 kinase | NM_001039396.1 |
| NEK2 | NIMA related kinase 2 | NM_001204182.1; NM_001204183.1 NM_002497.3; XM_005273147.1 |
| HASPIN | Histone H3 Associated Protein Kinase | NM_031965.2 |

Mitotic Kinase Inhibitors:

Examples of mitotic kinase inhibitors include inhibitors for PLK1 (e.g., GSK461364, B12536, Tak960, NMS-P937, B16727 or volasertib), PLK2, PLK3, PLK4, Aurora kinases 1/2 (e.g., alisertib), CDK1/2, CHK1/2 (e.g., AZD7762, prexasertib), BUB1, BUBR1, MPS1, NEK2, HASPIN (Schmit et al., *Mol Cancer Ther.* 6(7)1920-31, 2007). These mitotic kinases can be targeted with small molecule inhibitors, oligonucleotides (e.g., siRNA, miRNA, antisense oligonucleotides), and/or antibodies, all are contemplated in this application.

Non-specific Aurora A inhibitors include: MLN8054 (Millennium Pharmaceuticals, Cambridge, Mass.; Jones et al., *Proc Am Soc Clin Oncol Annu Meet* 25: 3577, 2007); MK-0457 (VX-680; Harrington et al., *Nat Med* 10(3): 262-267, 2004); SU6668 (Sugen; Lapenna & Giordano, *Nature Rev Drug Discovery* 8: 547-566, 2009, and supplementary information); and ZM447439, an inhibitor based on the quinazoline scaffold (Girdler et al., *J. Cell Sci.*, 119, 3664-3675, 2006).

In particular embodiments, selective inhibitors of Aurora A kinase include: compounds disclosed in, for example, US 2008/0045501, U.S. Pat. No. 7,572,784, WO 2005/111039, WO 2008/021038, U.S. Pat. No. 7,718,648, WO 2008/063525, US 2008/0167292, U.S. Pat. No. 8,026,246, WO 2010/134965, US 2010/0310651, WO 2011/014248, US 2011/0039826, and US 2011/0245234; sodium 4-{[9-chloro-7-(2-fluoro-6-methoxyphenyl)-5H-pyrimido[5,4-i] [2]benzazepin-2-yl]amino}-2-methoxybenzoate; KW-2449

(Kyowa Hakko), ENMD-2076 (ENMD-981693; EntreMed); and MK-5108 (Vertex/Merck).

Other Aurora kinase inhibitors include: Hesperadin (Hauf et al., *J Cell Biol* 161(2): 281-294, 2003), AZD1152 (quinazoline prodrug, active metabolite is AZD-1152-HQPA; AstraZeneca, Cambridge, UK; Schellens et al., *J Clin Oncol* 24:122s, 2006; Yang et al., *Blood* 110(6): 2034-2040, 2007), MLN8237 (Alisertib, selective, competitive, and reversible small-molecule inhibitor of Aurora A kinase; Millennium Pharmaceuticals, Cambridge, Mass.; Gorgun et al., *Blood* 115(25): 5202-5213, 2010; Friedberg et al., *J Clin Oncol* 32(1): 44-50, 2014); CYC-116 (Cyclapolin 1; Cyclacel Ltd., Cambridge, UK; Taylor & Peters, *Curr Opin Cell Biol* 20: 77-84, 2008); AS-703569 (R-763; Rigel Pharmaceuticals, San Francisco, Calif.); AT9283 (Astex; Howard et al., *J Med Chem* 52(2): 379-388, 2009); PHA-739358 (3-aminopyrazole derivative; Nerviano Medical Sciences; Carpinelli et al., *Mol Cancer Ther* 6(12): 3158-3168, 2007); PHA-680632 (Soncini et al., *Clin Cancer Res* 12(13): 4080-4089, 2006); SNS-314 (Sunesis Pharmaceuticals, San Francisco, Calif.; Lapenna & Giordano, *Nature Reviews Drug Discovery* 8: 547-566, 2009, and supplementary information); and PF-3814735 (Bhattacharya et al., *Am Assoc Canc Res* 68(9) Supplement LB-147, 2008). Reviewed in Gautschi et al., *Clin. Cancer Res.* 14(6): 1639-48, 2008. WO 01/21596 describes quinazoline derivatives to inhibit aurora-2 kinase. More than 30 small molecule Aurora kinase inhibitors are in different stages of preclinical and clinical development (Lapenna & Giordano *Nature Reviews Drug Discovery* 8: 547-566, 2009, and supplementary information; Kollareddy et al., *Invest New Drugs* 30(6): 2411-2432, 2012).

A cell cycle inhibitor, JNJ-7706621, shows potent inhibition of several cyclin-dependent kinases (CDKs) and Aurora kinases, and selectively blocks proliferation of tumor cells of various origins. At low concentrations, JNJ-7706621 slows the growth of cells and at high concentrations induces cytotoxicity. JNJ-7706621 treatment of cells has shown a delayed progression through G1 of the cell cycle and an arrest of the cell cycle at the G2-M phase (Emanuel et al., *Cancer Res.* 65: 9038-9046, 2005).

Inhibitors of CDKs are described in, for example, EP1244668, EP1507780, EP153976, EP1590341 EP1615926, WO 03/63764, U.S. Pat. Nos. 6,107,305, 6,413,974, WO 1999/02162, WO 2000/12486, WO 2000/39101, WO 2001/14375, WO 2002/10162, WO 2002/04429, WO 2002/096888, and WO 2003/7076437. A number of adenosine δ'-triphosphate (ATP) competitive small organic molecules as well as peptides have been reported in the literature as CDK inhibitors for the potential treatment of cancers.

Small molecular cyclin dependent kinase inhibitors are also described in: Glab et al., *FEBS Lett.* 353: 207-211, 1994; Kitagawa et al., *Oncogene* 8: 2425-2432, 1993; Losiewicz et al., *Biochem. Biophys. Res. Commun.* 201: 589-595, 1994; Carlson et al., *Cancer Res.* 56: 2973-2978, 1996; Kelland, *Expert Opin. Invest. Drugs* 9: 2903-2911, 2000; Senderowicz, *Invest. New Drugs* 17: 313-320, 1999; and Vassilev et al., *PNAS* 103(28): 10660-10665, 2006. In particular embodiments, CDK inhibitors can include: flavopiridol (Senderowicz *Invest New Drugs* 17(3): 313-320, 1999); olomoucine (Vesely et al., *Eur. J. Biochem.* 224: 771-786, 1994); roscovitine (Meijer et al., *Eur. J. Biochem.* 243: 527-536, 1997); CDKi-277 (Amgen, Thousand Oaks, Calif.; Payton et al., *Cancer Res.* 66: 4299-4308, 2006); RO-3306 (Vassilev et al., *PNAS* 103(28): 10660-10665, 2006); purvalanol A (Villerbu et al., *Int. J. Cancer* 97: 761-769, 2002); NU6140 (Pennati et al., *Mol. Cancer Ther.* 4: 1328-1337, 2005); s-CR8 (Bettayeb et al., *Oncogene* 27: 5797-5807, 2008); N-&-N1 (GP0210); Greenpharma S.A.S., Orleans, France; Bettayeb et al., *Mol. Cancer Ther.* 7: 2713-2724, 2008); AZ703 (AstraZeneca, Cambridge, UK; Byth et al., *Mol. Cancer Ther.* 5: 655-664, 2006); JNJ-7706621 (Johnson & Johnson, New Brunswick, N.J.; Emanuel et al., *Cancer Res.* 65: 9038-9046, 2005); RGB-286199 (GPC Biotech AG, Planegg, Germany; Wang et al., *Proc. Amer. Assoc. Cancer Res.* 46, Abstr. 4428, 2005); and SNS-032 (Sunesis Pharmaceuticals, San Francisco, Calif.; Choong et al., *Bioorg. Med. Chem. Lett.* 18: 5763-5765, 2008; Fan et al., *Bioorg. Med. Chem. Lett.* 18: 6236-6239, 2008).

Polo-like kinase inhibitors include: Scytonemin (Stevenson et al., *Inflamm Res* 51: 112-114, 2002); Wortmannin (Liu et al., *Chem Biol* 12: 99-107, 2005); ON-01910 (or ON 01910.Na; multitargeted intravenous cell cycle inhibitor; Onconova Therapeutics Inc., Newtown, Pa.; Gumireddy et al., *Cancer Cell* 7: 275-286, 2005); BI-2536 (an ATP-competitive inhibitor of PLK1; Boehringer Ingelheim, Ingelheim, Germany; Steegmaier et al., *Current Biology* 17: 316-322, 2007); BI 6727 (dihydropteridinone derivative inhibitor of PLK; Boehringer Ingelheim, Ingelheim, Germany; Rudolph et al., *Clin Cancer Res* 15(9): 3094-3102, 2009; GSK-61364 (or GSK-461364A; selective intravenous thiophene amide inhibitor of PLK1; Laquerre et al. A potent and selective Polo-like kinase 1 (Plk1) inhibitor (GSK461364) induces cell cycle arrest and growth inhibition of cancer cell. Presented at the 98th American Association for Cancer Research Annual Meeting, Los Angeles, Calif., Apr. 14-18, 2007); HMN-214 (oral stilbene derivative inhibitor of PLK1; prodrug of the active agent HMN-176; Nippon Shinyaku Co. Ltd, Kyoto, Japan; Garland et al., *Clin Can Res* 12:5182-5189, 2006); ZK-thiazolidinone (TAL; ATP-competitive inhibitor of PLK1; Bayer Schering Pharma AG, Berlin, Germany; Santamaria et al., *Mol Biol Cell* 18:4024-4036, 2007); NMS-1 (an orally available selective PLK1 inhibitor; Nerviano Medical Sciences, Milano, Italy; Beria et al. Antitumoral activity of pyrazoloquinazoline derivatives as potent oral Plk-1 specific inhibitors. Presented at the 20th European Organization for Research and Treatment of Cancer-National Cancer Institute-American Association for Cancer Research Symposium on Molecular Targets and Cancer Therapeutics, Geneva, Switzerland, Oct. 21-24, 2008); CYC-800 (a benzthiazole-3-oxide derivative selective PLK1 inhibitor; Cyclacel Ltd., Cambridge, UK; McInnes et al., *Curr Top Med Chem* 5:181-197, 2005); DAP-81 (a diaminopyrimidine derivative that targets PLKs; Rockefeller University, New York; Peters et al., *Nat Chem Biol* 2: 618-626, 2006); LC-445 (a specific non-ATP competitive allosteric inhibitor of PLK3; Avalon Pharmaceuticals, Germantown, Md.; Horrigan et al. A small molecule allosteric inhibitor of Polo-like kinase 3 induces apoptosis and disrupts the integrity of the mitotic spindle apparatus in cancer cells. Presented at the 20th European Organization for Research and Treatment of Cancer-National Cancer Institute-American Association for Cancer Research Symposium on Molecular Targets and Cancer Therapeutics, Geneva, Switzerland, Oct. 21-24, 2008); centrinone (LCR-263) and centrinone-B (LCR-323) (inhibitors of PLK4; Wong et al., *Science* 348(6239): 1155-1160, 2015). Plk inhibitors are described in Schoffski *The Oncologist* 14: 559-570, 2009.

Inhibitors of MPS1 kinase include NMS-P715 (a pyrazolo-quinazoline; Colombo et al., *Cancer Res* 70(24): 10255-10264, 2010); Mps-1-IN-1 and Mps1-IN-2 (Kwiatkowski et al., *Nat Chem Biol* 6(5): 359-368 2010; Mps-1-IN-3 (Bakhos et al., JNCI: *Journal of the National Cancer*

*Institute* 105(17): 1322-1331, 2013); and MPI-0479605 (Tardif et al., *Mol Cancer Ther* 10(12): 2267-2275, 2011).

In particular embodiments, a mitotic kinase inhibitor includes aminopyrazine inhibitors of Nek2 (Whelligan et al., *J Med Chem* 53:7682-7698, 2010).

Inhibitors of Wee1 kinase include PD0166285 (pyrido-pyrimidine derivative that is a nonselective inhibitor of WEE1); PD0407824 (pyrrolo-carbazole derivative that is a more selective inhibitor of WEE1); WEE1 inhibitor II (pyrrolo-carbazole derivative); and 4-(2-phenyl)-9-hydroxy-pyrrolo[3,4-c]-carbazole-1,3-(2H,6H)-dione (PHCD). De Witt Hamer et al. (2011) Clin Cancer Res; 17(13): 4200-4207; Palmer et al. (2006) J Med Chem 49: 4896-4911.

The terms "inhibitor of [a target protein]" or "[a target protein] inhibitor" are used to signify a compound that is capable of interacting with the target protein and inhibiting its activity, such as an enzymatic activity. By way of example, inhibiting a target kinase enzymatic activity means reducing the ability of that target kinase to phosphorylate a substrate peptide or protein. In various embodiments, such reduction of kinase activity is at least about 20%, at least about 30%, at least about 40%, at least about 50%, at least about 60%, at least about 70%, at least about 80%, or at least about 90%. In various embodiments, the concentration of kinase inhibitor (or another inhibitor) required to reduce kinase enzymatic activity of a target kinase (or the activity of another target) is less than about 1 µM, less than about 500 nM, less than about 100 nM, or less than about 50 nM. In embodiments, the concentration that is required to inhibit the enzymatic activity of a target (such as a target kinase) is lower than the concentration of the inhibitor that is required to inhibit the enzymatic activity of other kinase(s), or other proteins in the same family or sharing an activity. In various embodiments, the concentration of an inhibitor that is required to reduce the enzymatic activity of a target protein is at least about 2-fold, at least about 5-fold, at least about 10-fold, at least about 20-fold, at least about 50-fold, at least about 100-fold, at least about 500-fold, or at least about 1000-fold lower than the concentration of the inhibitor that is required to reduce enzymatic activity of other proteins, particularly other similar proteins (such as other kinases). Inhibitors can also induce the reduction of the target proteins or the mRNA encoding the target protein using oligonucleotides (e.g., siRNA, antisense) by at least about 20%, at least about 30%, at least about 40%, at least about 50%, at least about 60%, at least about 70%, at least about 80%, or at least about 90% of the original mRNA and/or protein level.

In particular embodiments, inhibition of a mitotic kinase, such as PLK1, can modulate the immune suppressive tumor microenvironment via reduction of, for example, phosphorylated STAT3, or other immune suppressive pathway, thereby benefiting antitumor immune response.

(III) IMMUNE CHECKPOINT INHIBITORS

Checkpoint inhibitor therapy is a recently developing form of cancer immunotherapy. The therapy targets immune checkpoints, key regulators of the immune system that stimulate or inhibit its actions, which tumors can use to protect from immune system attacks. Checkpoint therapy can block inhibitory checkpoints, restoring immune system function (Pardoll, *Nature Revs. Cancer* 12(4):252-264, 2012). The first anti-cancer drug targeting an immune checkpoint was ipilimumab, a CTLA-4 blocker approved in the United States in 2011 (Cameron et al., *Drugs* 71(8):1093-1104, 2011). See also Wieder et al., *J Allergy Clin Immunol.* 142(5): 1403-1414, 2018.

Immune checkpoint inhibitors indirectly treat cancer by treating the immune system. Inhibitors of immune checkpoints inhibit the normal immunosuppressive function of immune checkpoint molecules, for example, by down regulation of expression of the checkpoint molecules or by binding thereto and blocking normal receptor/ligand interactions. As the immune checkpoint molecules put brakes on an immune system response to an antigen, so an inhibitor of an immune checkpoint molecule reduces this immunosuppressive effect and enhances the immune response. Molecules that play a role in immune checkpoints include cytotoxic T-lymphocyte-associated antigen 4 (CTLA-4) and programmed death 1 T cell receptor (PD-1).

CTLA-4, PD-1, and their ligands are members of the CD28-B7 family of co-signaling molecules that play important roles throughout all stages of T-cell and other cell functions. The PD-1 receptor is expressed on the surface of activated T cells (and B cells) and, under normal circumstances, binds to its ligands (PD-L1 and PD-L2) that are expressed on the surface of antigen-presenting cells, such as dendritic cells or macrophages. This interaction sends a signal into the T cell and essentially switches the T cell off or inhibits the T cell. Cancer cells take advantage of this system by driving high levels of expression of PD-L1 on their surface. This allows cancer cells to gain control of the PD-1 pathway and switch off T cells expressing PD-1 that may enter the tumor microenvironment, thus suppressing the anticancer immune response. The immunotherapy ipilimumab, a monoclonal antibody that targets CTLA-4 on the surface of T cells, has been approved for the treatment of melanoma. Various new targeted immunotherapies aimed at the programmed death-1 (PD-1) T-cell receptor or its ligands (PD-L1 or PD-L2) may also prove to be effective. Additional immune checkpoint targets may also prove to be effective, such as T-cell Immunoglobulin domain and Mucin domain 3 (TIM-3), Lymphocyte Activation Gene-3 (LAG-3), various B7 ligands, BTLA, adenosine A2A receptor (A2AR), and others.

Currently approved immune checkpoint inhibitor targets include CTLA-4, PD-1, and PD-L1. PD-1 is the transmembrane programmed cell death 1 protein (also called PDCD1 and CD279), which interacts with PD-L1 (PD-1 ligand 1, or CD274). PD-L1 on the cell surface binds to PD-1 on an immune cell surface, which inhibits immune cell activity. A key PD-L1 function is regulation of T cell activities (Butte et al., *Immunity* 27(1); 111-122, 2007; Karwacz et al., *EMBO Mol. Med.* 3(10:581-592, 2011). It appears that cancer-mediated upregulation of PD-L1 on the cell surface may inhibit T cells that might otherwise attack cancer cells. Antibodies that bind to either PD-1 or PD-L1 and therefore block the interaction may allow the T-cells to attack the tumor (Syn et al., *The Lancet Oncology* 18(12):e731-e741, 2017).

In the immune system, the critical balance between rejection and self-tolerance is maintained by a finely tuned series of co-regulatory receptor-ligand interactions. Recent attention has focused on the programmed death (PD)-1/PD-1 ligand (PD-L1, B7-H1) pathway as a key mediator of tumor immune tolerance. Under physiologic conditions, the inhibitory PD-1 receptor is expressed on activated immune effector cells, including T, B and NK cells. Through interactions with its ligands PD-L1 and PD-L2, normally expressed on antigen presenting cells (APCs), immune effector activity in peripheral tissues during inflammatory processes is self-limited. This inhibitory system is fundamental to protecting healthy tissues and non-infected cells during clearance of viral and bacterial intracellular infections. However, many human cancers have been shown to express PD-1 ligands, thus inducing immune tolerance locally in the tumor microenvironment (TME) and facilitating tumor cell escape from immune attack. Two general mechanisms promoting expression of PD-L1 on tumor cells have been postulated. In some tumors, aberrant signaling pathways can constitutively up-regulate PD-L1 expression, a phenomenon termed "innate immune resistance"; in others, the expression of PD-L1 is an adaptive mechanism that occurs in response to inflammatory cytokines produced in the TME during an antitumor immune response ("adaptive immune resistance"). These mechanisms of PD-L1 expression are not mutually exclusive, i.e., constitutive PD-L1 expression on tumor cells may be further up-regulated by cytokines such as interferon-gamma (IFN-g).

PD-L1 expression by tumor cells prior to treatment correlates highly with response to anti-PD-1 monotherapy (for example, nivolumab (Bristol-Myers Squibb; OPDIVO™), pembrolizumab (Merck; KEYTRUDA®)) and anti-PD-L1 therapy (for example, MPDL3280A (Genentech/Roche)). Additional checkpoint inhibitors include: ipilimumab and tremelimumab (which target CTLA-4); atezolizumab (Genentech/Roche; Tecentriq), avelumab (Merck; Bavencio), and durvalumab (Medimmune/Strazeneca; Imfinzi) (which target PD-L1); and cemiplimab (REGN-2810), nivolumab, pembrolizumab, and pidilizumab (which target PD-1). Spartalizumab (PDR001; Novartis) is also under development as a PD-1 inhibitor.

Methods of PD-1 blockade treatment, including treatment of cancers, are well known in the art. See, for instance, WO 2016/201425, US 2019/0275705, Kvistborg et al. (*Science Transl Med.* 6(254):254ra128, 2014), Zou et al. (*Science Transl Med.* 8(328):328rv4, 2016), and Sakuishi et al. *J Exp Med.* 207(10):2187-2194, 2010).

PD-1 blocking agents include those used to treat cancer (i.e., to inhibit the growth or survival of tumor cells). Cancers whose growth may be inhibited using antibodies or anti-PD-1 agents or other check point inhibitors include cancers typically responsive to immunotherapy, but also cancers that have not hitherto been associated with immunotherapy. Examples of cancers for treatment include melanoma (e.g., metastatic malignant melanoma), renal cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. The herein described treatments are applicable to malignancies that demonstrate improved disease-free and overall survival in relation to the presence of tumor-infiltrating lymphocytes in biopsy or surgical material, e.g., melanoma, colorectal, liver, kidney, stomach/esophageal, breast, pancreas, and ovarian cancer. Such cancer subtypes are known to be susceptible to immune control by T lymphocytes. Additionally, the provided technology is useful for treating refractory or recurrent malignancies whose growth may be inhibited using the PD-1 or other check point blockade treatments. Particularly cancers include those characterized by elevated expression of PD-1 and/or its ligands PD-L1 and/or PD-L2 in tested tissue samples, including: ovarian, renal, colorectal, pancreatic, breast, liver, glioblastoma, non-small cell lung cancer, gastric, esophageal cancers and melanoma. Cancers also include those associated with persistent infection with viruses such as human immunodeficiency viruses, hepatitis viruses class A, B and C, Epstein Barr virus, human papilloma viruses that are known to be causally related to for instance Kaposi's sarcoma, liver cancer, nasopharyngeal cancer, lymphoma, cervical, vulval, anal, penile, and oral cancers.

The PD-1/PD-L1 pathway is a well-validated target for the development of antibody therapeutics for cancer treatment. Anti-PD-1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (*Nature* 439: 682-687, 2006) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

In particular embodiments, immune checkpoint molecules include CTLA-4, PD-1, PD-L1, PD-L2, LAG-3, TIM-3, Killer-cell Immunoglobulin-like Receptor (KIR), CD160, B7-H3 (CD276), BTLA (CD272), IDO (Indoleamine 2,3-dioxygenase), adenosine A2A receptor (A2AR), and C10ORF54.

The term "immune checkpoint protein" or "immune checkpoint molecule" refers to a molecule that is expressed by T cells and that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g., Pardoll, *Nature Rev Cancer* 12:252-264, 2012; Mellman et al., *Nature* 480: 480-489, 2011). Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because the tumor microenvironment has relatively high levels of adenosine, which lead to a negative immune feedback loop through the activation of A2AR. B7-H3, also called CD276, was originally understood to be a co-stimulatory molecule but is now regarded as co-inhibitory. B7-H4, also called VTCN1, is expressed by tumor cells and tumor-associated macrophages and plays a role in tumor escape. B and T Lymphocyte Attenuator (BTLA), also called CD272, is a ligand of HVEM (Herpesvirus Entry Mediator). Cell surface expression of BTLA is gradually downregulated during differentiation of human CD8+ T cells from the naive to effector cell phenotype; however, tumor-specific human CD8+ T cells express high levels of BTLA. CTLA-4, also called CD152, is overexpressed on regulatory T (Treg) cells and serves to control T cell proliferation. IDO is a tryptophan catabolic enzyme in the tryptophan to kynurenine metabolic pathway that regulates innate and adaptive immunity. IDO is known to suppress T and natural killer (NK) cells, generate and activate Tregs and myeloid-derived suppressor cells, and promote tumor angiogenesis. Another important molecule is TDO, tryptophan 2,3-dioxygenase, a key enzyme in the tryptophan to kynurenine metabolic pathway (Platten et al., *Front Immunol.* 5: 673, 2014). KIR is a receptor for MHC Class I molecules on NK cells. LAG-3 works to suppress an immune response by action on Tregs as well as direct effects on CD8+ T cells. PD-1, Programmed Death 1 (PD-1) receptor, has two ligands, PD-L1 and PD-L2. This checkpoint is the target of melanoma drug Keytruda® (pembrolizumab, Merck & Co., Kenilworth, N.J.), which gained FDA approval in September 2014. An advantage of targeting PD-1 is that it can restore immune function in the tumor microenvironment. TIM-3 is expressed on activated human CD4+ T cells and regulates Th1 and Th17 cytokines. TIM-3 acts as a negative regulator of Th1/Tc1 function by triggering cell death upon interaction with its ligand, galectin-9. V-domain Ig suppressor of T cell activation (VISTA) is primarily expressed on hematopoietic cells so that consistent expression of VISTA on leukocytes within tumors may allow VISTA blockade to be effective across a broad range of solid tumors.

The term "immune checkpoint inhibitor" refers to any compound inhibiting the function of an immune inhibitory checkpoint protein. Inhibition includes reduction of function and full blockade. In particular embodiments, immune checkpoint inhibitors are antibodies that specifically recognize an immune checkpoint protein. In particular embodiments, immune checkpoint inhibitors include peptides, antibodies, nucleic acid molecules, and small molecules. In particular embodiments, an immune checkpoint inhibitor is administered for enhancing the proliferation, migration, persistence and/or cytotoxic activity of CD8+ T cells in the subject and in particular the tumor-infiltrating CD8+ T cells of the subject.

Immune checkpoint inhibitors include agents that inhibit (directly or indirectly) at least one of CTLA-4, PD-1, PD-L1, and the like. Suitable anti-CTLA-4 therapy agents for use in the methods of the disclosure include anti-CTLA-4 antibodies, human anti-CTLA-4 antibodies, mouse anti-CTLA-4 antibodies, mammalian anti-CTLA-4 antibodies, humanized anti-CTLA-4 antibodies, monoclonal anti-CTLA-4 antibodies, polyclonal anti-CTLA-4 antibodies, chimeric anti-CTLA-4 antibodies, ipilimumab, tremelimumab, anti-CD28 antibodies, anti-CTLA-4 adnectins, anti-CTLA-4 domain antibodies, single chain anti-CTLA-4 fragments, heavy chain anti-CTLA-4 fragments, light chain anti-CTLA-4 fragments, inhibitors of CTLA-4 that agonize the co-stimulatory pathway, the antibodies disclosed in WO 2001/014424, the antibodies disclosed in WO 2004/035607, the antibodies disclosed in US 2005/0201994, and the antibodies disclosed in EP1212422B1. Additional anti-CTLA-4 antibodies are described in U.S. Pat. Nos. 5,811,097; 5,855, 887; 6,051,227; 6,984,720; WO 01/14424; WO 00/37504; US 2002/0039581; and US 2002/086014. Other anti-CTLA-4 antibodies that can be used in a method of the present disclosure include, for example, those disclosed in: WO 98/42752; U.S. Pat. Nos. 6,682,736; 6,207,156; Hurwitz et al., *Proc. Natl. Acad. Sci. USA,* 95(17): 10067-10071, 1998; Camacho et al., *J. Clin. Oncology,* 22(145): Abstract No. 2505, 2004 (antibody CP-675206); Mokyr et al., *Cancer Res* 58: 5301-5304, 1998; U.S. Pat. No. 5,977,318: U.S. Pat. Nos. 6,682,736; 7,109,003; and 7,132,281.

Suitable anti-PD-1 and anti-PD-L1 therapy agents for use in the methods of the disclosure include anti-PD-1 and anti-PD-L1 antibodies, human anti-PD-1 and anti-PD-L1 antibodies, mouse anti-PD-1 and anti-PD-L1 antibodies, mammalian anti-PD-1 and anti-PD-L1 antibodies, humanized anti-PD-1 and anti-PD-L1 antibodies, monoclonal anti-PD-1 and anti-PD-L1 antibodies, polyclonal anti-FD-1 and anti-PD-L1 antibodies, chimeric anti-PD-1 and anti-PD-L1 antibodies. In particular embodiments, anti-PD-1 therapy agents include nivolumab, pembrolizumab, pidilizumab, MEDI0680 (AstraZeneca, Cambridge, UK), and combinations thereof. In particular embodiments, anti-PD-L1 therapy agents include atezolizumab, BMS-936559 (Bristol-Myers Squibb, New York, N.Y.), durvalumab (MEDI4736), avelumab (MSB0010718C), and combinations thereof.

Suitable anti-PD-1 and anti-PD-L1 antibodies are described in Topalian et al. (*Cancer Cell* 27: 450-461, 2015).

In particular embodiments, immune checkpoint inhibitors can include a modified ligand or an antisense nucleic acid molecule such as siRNA designed to inhibit a particular immune checkpoint molecule. In particular embodiments, the siRNA prevents the translation of the immune checkpoint molecule, thus preventing the expression of the protein. Given that the genomic sequences of many immune checkpoint molecules are known, one of ordinary skill in the art would be able to use routine methods to design suitable inhibitory antisense nucleic acid molecules.

In certain embodiments, checkpoint inhibitors can be siRNA, small molecule inhibitors, or antibody against (specific for) an immune checkpoint molecule beneficial for cancer treatment. Such targets include PD-L1, PD-1, CTLA-4, LAG-3, TIM-3, B7-H3, VISTA, A2AR, and IDO (Khair et al., *Frontiers Immunology,* 10:453, 2019).

One of ordinary skill in the art will understand how to access representative sequences for such targets, which are readily available in public sequence databases. The following table provides sample sequence information:

| Gene Abbreviation | Full gene name | Representative GenBank Accession #s |
| --- | --- | --- |
| PD-L1 | CD274 molecule | NM_001267706.1; NM_001314029.1; NM_014143.3; NR_052005.1 |
| PD-1 | programmed cell death 1 | NM_005018.2; XM_006712573.2; XM_017004293.1 |
| CTLA-4 | cytotoxic T-lymphocyte associated protein 4 | NM_001037631.2; NM_005214.4 |
| LAG3 | Lymphocyte activating 3 | NM_002286.5; XM_011520956.1 |
| TIM-3 | T-cell immunoglobulin and mucin-domain containing-3 | NM_032782.4 |
| B7-H3 | CD276 (Cluster of Differentiation 276) | NM_001024736.1; NM_001329628.1; |
| VISTA | V-domain Ig suppressor of T cell activation | NM_001329629.1; NM_025240.2; |
| A2AR | adenosine A2a receptor | XM_005254700.4; XM_011522095.2; |
| IDO | indoleamine 2,3-dioxygenase | XM_011522096.2; XM_017022638.1 |

(IV) OPTIONAL ADDITIONAL COMPONENTS

In addition to the mitotic kinase inhibitor and the immune checkpoint inhibitor, the therapeutic constructs provided herein can optionally contain or be administered with one or more optional components. These optional components include adjuvant(s), therapeutic oligonucleotides, additional anti-cancer agent(s), and targeting moieties.

Adjuvants

The therapeutic constructs provided herein optionally may include at least one adjuvant component, contained within or otherwise associated with the delivery vehicle. The therapeutic construct embodiments are not limited to a particular type of adjuvant, though specific examples are provided herein.

Generally, adjuvants are any substance whose admixture into a vaccine composition increases or otherwise modifies the immune response to the (cancer) antigen. The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased antigen-specific T cell proliferation, death of target cells, or cytokine secretion. An adjuvant may also alter an immune response, for example, by changing a primarily humoral or Th2 response into a primarily cellular, or Th1 response.

Suitable adjuvants include, but are not limited to TLR-binding DNA substituents such as CpG oligonucleotides (e.g., ISS 1018; Amplivax; CpG ODN 7909, CpG ODN 1826, CpG ODN D19, CpG ODN 1585, CpG ODN 2216, CpG ODN 2336, ODN 1668, ODN 1826, ODN 2006, ODN 2007, ODN 2395, ODN M362, and SD-101), DNA TLR agonists that contain a CpG sequence (e.g., dSLIM), non-CpG DNA TLR agonists (e.g., ENANDIM®), and cationic peptide-conjugated CpG oligonucleotides (e.g., IC30, IC31); RNA TLR agonists (e.g., Poly I:C and Poly-ICLC); aluminum salts (e.g., aluminum hydroxide, aluminum phosphate, aluminum chloride, and aluminum potassium sulfate); anti-CD40 antibodies (e.g., CP-870,893); cytokines, such as granulocyte-macrophage colony-stimulating factor (GM-CSF); small molecule TLR agonists (e.g., imiquimod, resiquimod, gardiquimod, and 3M-052); fusion proteins (e.g., ImuFact IMP321, CyaA, and ONTAK); oil- or surfactant-based adjuvants such as MF59, MONTANIDE® IMS 1312, MONTANIDE® ISA 206, MONTANIDE® ISA 50V, and MONTANIDE® ISA-51; a plant extract such as QS21 STIMULON® (Aquila Biotech, Worcester, Mass., USA), which is derived from saponin; mycobacterial extracts and synthetic bacterial cell wall mimics, such as lipopolysaccharides (e.g., monophosphoryl lipid A, OM-174, OM-197-MP-EC, and Pam3Cys); xanthenone derivatives (e.g., vadimezan); mixtures thereof (e.g., AS-15); and other proprietary adjuvants such as Ribi's Detox, Quil, or Superfos. Several immunological adjuvants (e.g., MF59 specific for dendritic cells and their preparation have been described previously (Dupuis et al., *Cell Immunol.* 186(1): 18-27, 1998; Allison, *Dev Biol Stand.;* 92:3-11, 1998). Also cytokines may be used as adjuvants. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589) and acting as immunoadjuvants (e.g., IL-12) (Gabrilovich et al., *J Immunother Emphasis Tumor Immunol.* (6):414-418, 1996). Toll like receptors (TLRs) or agents that activate TLRs may also be used as adjuvants, and are important members of the family of pattern recognition receptors (PRRs) which recognize conserved motifs shared by many micro-organisms, termed "pathogen-associated molecular patterns" (PAMPS).

In some embodiments, the adjuvant includes a CpG oligonucleotide. CpG immunostimulatory oligonucleotides have also been reported to enhance the effects of adjuvants in a vaccine setting. Without being bound by any particularly mechanistic theory, CpG oligonucleotides act at least in part by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of $T_H1$ cells and strong cytotoxic T-lymphocyte (CTL) generation, even in the absence of CD4 T-cell help. The $T_H1$ bias induced by TLR9 stimulation is maintained even in the presence of vaccine adjuvants such as alum or incomplete Freund's adjuvant (IFA) that normally promote a $T_H2$ bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Krieg, *Nature Reviews, Drug Discovery*, 5:471-484, 2006). U.S. Pat. No. 6,406,705 describes the combined use of CpG oligonucleotides, non-nucleic acid adjuvants and an antigen to induce an antigen-specific immune response. A commercially available CpG TLR9 agonist is dSLIM (double Stem Loop Immunomodulator) by Mologen (Berlin, GERMANY). Other TLR binding molecules such as RNA binding TLR 7, TLR 8 and/or TLR 9 may also be used.

Xanthenone derivatives such as, for example, vadimezan or AsA404 (also known as 5,6-dimethylaxanthenone-4-acetic acid (DMXAA)), may also be used as adjuvants according to embodiments of the invention. Alternatively, such derivatives may also be administered in parallel to the vaccine of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al., *J Immunology*, 190:5216-5225, 2013; and Kim et al., *ACS Chem Biol*, 8:1396-1401, 2013). Other examples of useful adjuvants include, but are not limited to, chemically modified CpGs (e.g. CpR, Idera), Poly(I:C) (e.g. polyi:CI2U), non-CpG bacterial DNA or RNA as well as immunoactive small molecules and antibodies such as cyclophosphamide, sunitinib, bevacizumab, CELEBREX®, NCX-4016, sildenafil, tadalafil, vardenafil, sorafenib, XL-999, CP-547632, pazopanib, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, SARGRAMOSTIM®).

Poly-ICLC is a synthetically prepared double-stranded RNA consisting of polyI and polyC strands of average length of about 5000 nucleotides, which has been stabilized to thermal denaturation and hydrolysis by serum nucleases by the addition of poly-lysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2' 5'-OAS and the PI/eIF2a kinase, also known as the PKR (4-6), as well as RIG-I helicase and MDA5.

Examples of immunological adjuvants that can be associated with the therapeutic constructs include TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives thereof including, but not limited to, monophosphoryl lipid A (MPL), glycopyranosyl lipid A, PET-lipid A, and 3-O-desacyl-4'-monophosphoryl lipid A. In a specific embodiment, the immunological adjuvant is MPL. In another embodiment, the immunological adjuvant is LPS. TLR ligands can also include, but are not limited to, TLR3 ligands (e.g., polyinosinic-polycytidylic acid (poly(I:C)), TLR7 ligands (e.g., imiquimod and resiquimod), and TLR9 ligands.

As used herein, the term "TLR-binding DNA substituent" refers to a substituent or moiety capable of binding to a toll-like receptor ("TLR"), including at least one deoxyribonucleic acid. In embodiments, a TLR-binding DNA substituent is a nucleic acid. In embodiments, the TLR-binding DNA substituent includes at least one nucleic acid analog. In embodiments, the TLR-binding DNA substituent includes at least one nucleic acid analog having an alternate backbone (e.g. phosphodiester derivative (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, or O-methylphosphoroamidite), peptide nucleic acid backbone(s), LNA, or linkages). In embodiments, a TLR-binding DNA substituent includes DNA. In embodiments, all nucleotide sugars in a TLR-binding DNA substituent are deoxyribose (e.g., all nucleotides are DNA). In embodiments, a TLR-binding DNA substituent consists of DNA. In embodiments, a TLR-binding DNA substituent includes or is DNA having internucleotide linkages selected from phosphodiesters and phosphodiester derivatives (e.g. phosphoramidate, phosphorodiamidate, phosphorothioate, phosphorodithioate, phosphonocarboxylic acids, phosphonocarboxylates, phosphonoacetic acid, phosphonoformic acid, methyl phosphonate, boron phosphonate, O-methylphosphoroamidite, or combinations thereof). In embodiments, a TLR-binding DNA substituent consists of DNA having internucleotide linkages selected from phosphodiesters and phosphorothioates. In embodiments, a TLR-binding DNA substituent includes or is DNA having backbone linkages selected from phosphodiesters and phosphorodithioates. In embodiments, a TLR-binding DNA substituent includes or is DNA including phosphodiester backbone linkages. In embodiments, a TLR-binding DNA substituent includes or is DNA including phosphorothioate backbone linkages. In embodiments, a TLR-binding DNA substituent includes or is DNA including phosphorodithioate backbone linkages. In embodiments, a TLR-binding DNA substituent preferentially binds TLR9 over other TLR. In embodiments, a TLR-binding DNA substituent specifically binds TLR9. In embodiments, a TLR-binding DNA substituent specifically binds TLR3. In embodiments, a TLR-binding DNA substituent specifically binds TLR7. In embodiments, a TLR-binding DNA substituent specifically binds TLR8. In embodiments, a TLR-binding DNA substituent specifically binds a cellular sub-compartment (e.g. endosome) associated TLR (e.g. TLR3, TLR7, TLR8, or TLR9). In embodiments, a TLR-binding DNA substituent includes or is a G-rich oligonucleotide. In embodiments, a TLR-binding DNA substituent includes a CpG motif, wherein C and G are nucleotides and p is the phosphate connecting the C and G. In embodiments, the CpG motif is unmethylated. In embodiments, a TLR-binding DNA substituent is a Class A CpG oligodeoxynucleotide (ODN). In embodiments, a TLR-binding DNA substituent is a Class B CpG oligodeoxynucleotide (ODN). In embodiments, a TLR-binding DNA substituent is a Class C CpG oligodeoxynucleotide (ODN). In embodiments, a TLR-binding DNA substituent (e.g., TLR9-binding DNA substituent) consists of deoxyribonucleic acids with A, G, C, or T bases and phosphodiester linkages and/or phosphodiester derivative linkages (e.g., phosphorothioate linkage(s)).

The phrase "CpG motif" refers to a 5' C nucleotide connected to a 3' G nucleotide through a phosphodiester internucleotide linkage or a phosphodiester derivative internucleotide linkage. In embodiments, a CpG motif includes a phosphodiester internucleotide linkage. In embodiments, a CpG motif includes a phosphodiester derivative internucleotide linkage.

As used herein, the term "Class A CpG ODN" or "A-class CpG ODN" or "D-type CpG ODN" or "Class A CpG DNA sequence" is used in accordance with its common meaning in the biological and chemical sciences and refers to a CpG motif including oligodeoxynucleotide including one or more of poly-G sequence at the 5', 3', or both ends; an internal palindrome sequence including CpG motif; or one or more phosphodiester derivatives linking deoxynucleotides. In embodiments, a Class A CpG ODN includes poly-G sequence at the 5', 3', or both ends; an internal palindrome sequence including CpG motif; and one or more phosphodiester derivatives linking deoxynucleotides. In embodiments, the phosphodiester derivative is phosphorothioate. Examples of Class A CpG ODNs include ODN D19, ODN 1585, ODN 2216, and ODN 2336.

The terms "Class B CpG ODN" or "B-class CpG ODN" or "K-type CpG ODN" or "Class B CpG DNA sequence" are used in accordance with their common meaning in the biological and chemical sciences, and refer to a CpG motif including oligodeoxynucleotide including one or more of a 6mer motif including a CpG motif; phosphodiester derivatives linking all deoxynucleotides. In embodiments, a Class B CpG ODN includes one or more copies of a 6mer motif including a CpG motif and phosphodiester derivatives linking all deoxynucleotides. In embodiments, the phosphodiester derivative is phosphorothioate. In embodiments, a Class B CpG ODN includes one 6mer motif including a CpG motif. In embodiments, a Class B CpG ODN includes two copies of a 6mer motif including a CpG motif. In embodiments, a Class B CpG ODN includes three copies of a 6mer motif including a CpG motif. In embodiments, a Class B CpG ODN includes four copies of a 6mer motif including a CpG motif. Examples of Class B CpG ODNs include ODN 1668, ODN 1826, ODN 2006, and ODN 2007.

The terms "Class C CpG ODN" or "C-class CpG ODN" or "C-type CpG DNA sequence" are used in accordance with their common meaning in the biological and chemical sciences and refers to an oligodeoxynucleotide including a palindrome sequence including a CpG motif and phosphodiester derivatives (phosphorothioate) linking all deoxynucleotides. Examples of Class C CpG ODNs include ODN 2395 and ODN M362.

Therapeutic Oligonucleotides.

Optionally, the provided therapeutic constructs may contain one or more therapeutic oligonucleotides. Different types of therapeutic oligonucleotides can be used and non-exhaustively include siRNA, miRNA, antisense oligonucleotide, ribozyme, aptamer, DNA, mRNA, sgRNA (for CRISPR), and CRISPR-cas9 elements. In other words, any chain of nucleotides can be utilized as long as they can specifically modulate (interfere or boost) the action or synthesis of certain gene(s) and protein(s). Each particular oligonucleotide may have a single or multiple targets. Examples of gene/protein targets of interest to the invention include immune checkpoints (discussed elsewhere herein), transcription factors, phosphatases, kinases, etc. Specific targets include, but are not limited to, STAT3, TGF-β, CD47, NOXI-5, HSP47, XBP1, BCL2, BCL-XL, AKT1, AKT2, AKT3, MYC, HER2, HER3, AR, Survivin, GRB7, EPS8L1, RRM2, PKN3, EGFR, IRE1-alpha, VEGF-R1, RTP801, proNGF, Keratin K6A, LMP2, LMP7, MECL1, HIF1α, Furin, KSP, eiF-4E, p53, β-catenin, ApoB, PCSK9, SNALP, CD39, CD73, MIF, VEGF, PIGF, CXCR4, CCR2, PLK1, MTDH, Twist, Lcn2, IL-6, IL-10, p65, and mitotic kinases (e.g., PLK1, PLK2, PLK3, PLK4, CDK1, CDK2, CHK1, CHK2, BUB1, BUBR1, MPS1, NEK2, HASPIN, Aurora A) as previously mentioned. Therapeutic oligonucleotides can also contain two strands that target two genes (such as siRNA against BCL2 and AKT1, siRNA against AR and MYC). They can also contain immunostimulatory sequences/elements that can thus simultaneously boost the immune response and regulate expression of target genes. They can also be designed to target the aforementioned genes that have mutations.

In certain embodiments, the therapeutic constructs include as an active agent an oligonucleotide that mediates RNA interference. RNA interference is a highly conserved mechanism triggered by double-stranded RNA (dsRNA) and able to downregulate transcript of genes homologous to the dsRNA. The dsRNA is first processed by Dicer into short duplexes of 21-23 nucleotides, called short interfering RNAs (siRNAs). Incorporated in RNA-induced silencing complex (RISC), they are able to mediate gene silencing through cleavage of the target mRNA. "siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target and not directed to a mRNA poly A tail.

In some embodiments, siRNA encapsulated within or associated with therapeutic constructs are utilized in methods and systems involving RNA interference. Such embodiments are not limited to a particular size or type of siRNA molecule. The length of the region of the siRNA complementary to the target, for example, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer.

In certain embodiments, it is contemplated that the siRNA delivery approach using therapeutic constructs disclosed herein (e.g., through loading of the siRNA on a therapeutic constructs) can be used to inhibit production of any gene of interest. Specific targets include, but are not limited to, STAT3, TGF-β, CD47, NOXI-5, HSP47, XBP1, BCL2, BCL-XL, AKT1, AKT2, AKT3, MYC, HER2, HER3, AR, Survivin, GRB7, EPS8L1, RRM2, PKN3, EGFR, IRE1-alpha, VEGF-R1, RTP801, proNGF, Keratin K6A, LMP2, LMP7, MECL1, HIF1α, Furin, KSP, eiF-4E, p53, β-catenin, ApoB, PCSK9, SNALP, CD39, CD73, MIF, VEGF, PIGF, CXCR4, CCR2, PLK1, MTDH, Twist, Lcn2, IL-6, IL-10, p65, and mitotic kinases as previously mentioned among genes known as drivers in cancer and other diseases. Further, it is specifically contemplated that siRNA can be directed to a variant or mutated gene, rather than a wildtype gene.

One of ordinary skill in the art will understand how to access representative sequences for these targets, which are readily available in public sequence databases. The following table provides sample sequence information:

| Gene Abbreviation | Full gene name | Representative GenBank Accession #s |
|---|---|---|
| STAT3 | Signal transducer and activator of transcription 3 | NM_003150.3; NM_139276.2; NM_213662.1; XM_005257616.3; XM_005257617.3; XM_011525145.2; XM_011525146.2; XM_017024972.1; XM_017024973.1; XM_017024974.1; XM_017024975.1; XM_017024976.1 |
| TGF-β | transforming growth factor beta 1 | NM_000660.6; XM_011527242.1 |
| CD47 | CD47 molecule | NM_001777.3; NM_198793.2; XM_005247908.1; XM_005247909.1; XM_017007536.1; XR_001740374.1; XR_001740375.1; XR_241521.1; XR_241522.1; XR_924218.1; XR_924219.1; XR_924220.1 |
| NOX1 | NADPH oxidase 1 | NM_001271815.1; NM_007052.4; NM_013955.2; XM_017029407.1 |
| NOX2 | cytochrome b-245 beta chain | NM_000397.3 |
| NOX3 | NADPH oxidase 3 | NM_015718.2 |
| NOX4 | NADPH oxidase 4 | NM_001143836.2; NM_001143837.1; NM_001291926.1; NM_001291927.1; NM_001291929.1; NM_001300995.1; NM_016931.4; XM_006718849.3; XM_011542857.2; XM_017017841.1; XM_017017842.1; XM_017017843.1; XM_017017844.1; XM_017017845.1; NR_120406.1 |
| NOX5 | NADPH oxidase 5 | NM_001184779.1; NM_001184780.1; NM_024505.3; NR_033671.2; NR_033672.1 |
| HSP47 | serpin family H member 1 | NM_001207014.1; NM_001235.3; XM_011545327.1 |
| XBP1 | X-box binding protein 1 | NM_001079539.1; NM_005080.3 |

-continued

| Gene Abbreviation | Full gene name | Representative GenBank Accession #s |
|---|---|---|
| BCL2 | B-cell lymphoma 2, apoptosis regulator | NM_000633.2; NM_000657.2; XM_011526135.2; XM_017025917.1; XR_935248.2 |
| BCL-XL/S, BCL2L, BCLX, Bcl-X, PPP1R52 | B-cell lymphoma 2 like 1 | NM_001191.3; NM_001317919.1; NM_001317920.1; NM_001317921.1; NM_001322239.1; NM_001322240.1; NM_001322242.1; NM_138578.2; XM_011528964.2; XM_017027993.1; NR_134257.1; XR_001754364.1; XR_936599.2 |
| AKT1 | AKT serine/threonine kinase 1 | NM_001014431.1; NM_001014432.1; NM_005163.2; XM_005267401.1; XM_017021075.1; XM_017021076.1; XM_017021077.1; XM_017021078.1 |
| AKT2 | AKT serine/threonine kinase 2 | NM_001243027.2; NM_001243028.2; NM_001330511.1; NM_001626.5; XM_011526614.1; XM_011526615.1; XM_011526616.1; XM_011526618.1; XM_011526619.1; XM_011526620.1; XM_011526622.2; XM_017026470.1 |
| AKT3 | AKT serine/threonine kinase 3 | NM_001206729.1; NM_005465.4; NM_181690.2; XM_005272994.4; XM_005272995.2; XM_006711726.3; XM_011544012.2; XM_011544013.2; XM_011544014.2; XM_016999985.1 |
| MYC | MYC proto-oncogene, bHLH transcription factor | NM_002467.4 |
| HER2 | erb-b2 receptor tyrosine kinase 2 | NM_001005862.2; NM_001289936.1; NM_001289937.1; NM_001289938.1; NM_004448.3; NR_110535.1 |
| HER3 | erb-b2 receptor tyrosine kinase 3 | NM_001005915.1; NM_001982.3 |
| AR | androgen receptor | NM_000044.4; NM_001011645.3; NM_001348061.1; NM_001348063.1; NM_001348064.1 |
| Survivin (BIRC5) | baculoviral inhibitor of apoptosis repeat-containing 5 | NM_001012270.1; NM_001012271.1; NM_001168.2; XR_243654.4; XR_934452.2 |
| GRB7 | growth factor receptor bound protein 7 | NM_001030002.2; NM_001242442.1; NM_001242443.1; NM_001330207.1; NM_005310.3; XM_017024536.1; XM_017024538.1 |
| EPS8L1 | EPS8 like 1 | NM_017729.3; NM_133180.2; XM_005259020.1; XM_011527050.1; XM_011527051.2; XM_011527052.2 |
| RRM2 | ribonucleotide | NM_001034.3; |

-continued

| Gene Abbreviation | Full gene name | Representative GenBank Accession #s |
|---|---|---|
| | reductase regulatory subunit M2 | NM_001165931.1 |
| PKN3 | protein kinase N3 | NM_001317926.1; NM_013355.4; XM_005251946.3; XM_006717080.2; XM_017014649.1; XM_017014650.1 |
| EGFR | epidermal growth factor receptor | NM_001346897.1; NM_001346898.1; NM_001346899.1; NM_001346900.1; NM_001346941.1; NM_005228.4; NM_201282.1; NM_201283.1; NM_201284.1 |
| IRE1-alpha (ERN1) | endoplasmic reticulum to nucleus signaling 1 | NM_001433.3; XM_017024347.1; XM_017024348.1 |
| VEGF-R1 (FLT1) | fms related tyrosine kinase 1 | NM_001159920.1; NM_001160030.1; NM_001160031.1; NM_002019.4; XM_011535014.1; XM_017020485.1 |
| RTP801 (DDIT4) | DNA damage inducible transcript 4 | NM_019058.3 |
| Keratin K6A | keratin 6A | NM_005554.3 |
| LMP2 | proteasome subunit beta 9 | NM_002800.4 |
| LMP7 | proteasome subunit beta 8 | NM_004159.4; NM_148919.3 |
| MECL1 | proteasome subunit beta 10 | NM_002801.3 |
| HIF1α | hypoxia inducible factor 1 alpha subunit | NM_001243084.1; NM_001530.3; NM_181054.2 |
| Furin | furin, paired basic amino acid cleaving enzyme | NM_001289823.1; NM_001289824.1; NM_002569.3 |
| KSP | fibroblast growth factor binding protein 2 | NM_031950.3 |
| eiF-4E | eukaryotic translation initiation factor 4E | NM_001130678.2; NM_001130679.2; NM_001331017.1; NM_001968.4 |
| p53 | tumor protein p53 | NM_000546.5; NM_001126112.2; NM_001126113.2; NM_001126114.2; NM_001126115.1; NM_001126116.1; NM_001126117.1; NM_001126118.1; NM_001276695.1; NM_001276696.1; NM_001276697.1; NM_001276698.1; NM_001276699.1; NM_001276760.1; NM_001276761.1 |
| β-catenin | catenin beta 1 | NM_001098209.1; NM_001098210.1; NM_001330729.1; NM_001904.3; XM_005264886.2; XM_006712983.1; XM_006712984.1; XM_006712985.1; XM_017005738.1 |
| ApoB | apolipoprotein B | NM_000384.2 |
| PCSK9 | proprotein convertase subtilisin/kexin type 9 | NM_174936.3; NR_110451.1 |
| SNALP | synaptosome associated protein 25 | NM_001322902.1; NM_001322903.1; |

-continued

| Gene Abbreviation | Full gene name | Representative GenBank Accession #s |
|---|---|---|
| | | NM_001322904.1; NM_001322905.1; NM_001322906.1; NM_001322907.1; NM_001322908.1; NM_001322909.1; NM_001322910.1; NM_003081.4; NM_130811.3; XM_005260808.4; XM_017028021.1; XM_017028022.1; XM_017028023.1 |
| CD39 | ectonucleoside triphosphate di-phosphohydrolase 1 | NM_001098175.1; NM_001164178.1; NM_001164179.1; NM_001164181.1; NM_001164182.1; NM_001164183.1; NM_001312654.1; NM_001320916.1; NM_001776.5; XM_011540370.2; XM_011540371.2; XM_011540372.2; XM_011540373.2; XM_011540374.2; XM_011540376.2; XM_011540377.2; XM_017016958.1; XM_017016959.1; XM_017016960.1; XM_017016961.1; XM_017016962.1; XM_017016963.1; XM_017016964.1 |
| CD73 | 5'-nucleotidase ecto | NM_001204813.1; NM_002526.3 |
| MIF | macrophage migration inhibitory factor (glycosylation-inhibiting factor) | NM_002415.1 |
| VEGF | vascular endothelial growth factor A | NM_001025366.2; NM_001025367.2; NM_001025368.2; NM_001025369.2; NM_001025370.2; NM_001033756.2; NM_001171622.1; NM_001171623.1; NM_001171624.1; NM_001171625.1; NM_001171626.1; NM_001171627.1; NM_001171628.1; NM_001171629.1; NM_001171630.1; NM_001204384.1; NM_001204385.1; NM_001287044.1; NM_001317010.1; NM_003376.5; |
| PIGF | phosphatidylinositol glycan anchor biosynthesis class F | NM_002643.3; NM_173074.2; XM_005264369.2; XM_011532908.2 |
| CXCR4 | C-X-C motif chemokine receptor 4 | NM_001008540.2; NM_001348056.1; NM_001348059.1; NM_001348060.1; NM_003467.2 |
| CCR2 | C-C motif chemokine receptor 2 | NM_001123041.2; NM_001123396.1; XM_011534069.1 |
| PLK1 | polo like kinase 1 | NM_005030.5 |
| MTDH | metadherin | NM_178812.3; XM_005251099.3; XM_011517367.2; XM_011517368.2; XM_011517369.2; XM_011517370.2; XM_017013966.1; XM_017013967.1; XM_017013968.1 |

Such embodiments are not limited to a particular manner of assessing the delivery profile of the siRNA in vitro and/or in vivo. In some embodiments, labelling the siRNA molecules with an imaging agent (e.g., fluorescent dye FITC, RITC, Cy™ dyes, Dylight® dyes, Alexa Fluor® dyes, or lanthanide probes) or a radiotracer permits visualization of the biodistribution of siRNA molecules at the organ level and also the intracellular delivery profile. In some embodiments, RT-PCR and western blot are used to analyze the target protein at the mRNA level and protein level, respectively.

In certain embodiments, the present invention provides methods for inhibiting a target gene in a cell comprising introducing into the cell (associated with an therapeutic construct) an siRNA capable of inhibiting the target gene by RNA interference, wherein the siRNA comprises two RNA strands that are complementary to each other, wherein the siRNA is loaded onto a therapeutic construct. In some embodiments, the siRNA is modified with cholesterol at the 3' sense strand. In some embodiments, the cell is within a human being or an animal subject (e.g., horses, dogs, cats, or other domestic, farm, or other animals with cancer).

MicroRNAs (miRNAs) or miRNA mimics are short, non-coding RNAs that can target and substantially silence protein coding genes through 3'-UTR elements. Important roles for miRNAs in numerous biological processes have been established, but comprehensive analyses of miRNA function in complex diseases are lacking. miRNAs are initially transcribed as primary miRNAs (pri-miRNAs) that are then cleaved by the nuclear RNAses Drosha and Pasha to yield precursor-miRNAs (pre-miRNAs). These precursors are further processed by the cytoplasmic RNAse III dicer to form short double stranded miR-miR* duplexes, one strand of which (miR) is then integrated into the RNA Induced Silencing Complex (RISC) that includes the enzymes dicer and Argonaute (Ago). The mature miRNAs (~17-24nt) direct RISC to specific target sites located within the 3'UTR of target genes. Once bound to target sites, miRNAs represses translation through mRNA decay, translational inhibition and/or sequestration into processing bodies (P-bodies) (Eulalio et al., Cell, 132:9-14, 2008; Behm-Ansmant et al., Cold Spring Harb. Symp. Quant. Biol., 71:523-530, 2006; Chu and Rana, Plos. Biology., 4:e210, 2006). Recent estimates find that over 60% of protein coding genes carry 3'-UTR miRNA target sites (Friedman et al., Genome Res., 19:92-105, 2009). In this regard, miRNAs act as key regulators of processes as diverse as early development (Reinhart et al., Nature, 403:901-906, 2000), cell proliferation and cell death (Brennecke et al., Cell, 113(1): 25-36, 2003), apoptosis and fat metabolism (Xu et al., Curr. Biol., 13(9):790-795, 2003), and cell differentiation (Chen et al., Mol. Microbiol., 53843-856, 2004; Dostie et al., RNA-A Publication of the RNA Society, 9:180-186, 2003). In addition, studies of miRNA expression in chronic lymphocytic leukemia (Calin et al., Proc. Natl. Acad. Sci. USA, 105: 5166-5171, 2008), colonic adenocarcinoma (Michael et al.,

*Mol. Cancer Res.*, 1:882-891, 2003), Burkitt's lymphoma (Metzler et al., *Genes Chromosomes Cancer,* 39:167-169, 2004), cardiac disease (Zhao et al., *Cell,* 129:303-317, 2007) and viral infection (Pfeffer et al., *Science,* 304:734-736, 2004) suggest vital links between miRNA and numerous diseases.

miRNAs thus far observed have been approximately 21-22 nucleotides in length and they arise from longer precursors, which are transcribed from non-protein-encoding genes. Reviewed in Carrington and Ambros (*Science,* 301(5631):336-338, 2003). The precursors form structures that fold back on each other in self-complementary regions; they are then processed by the nuclease Dicer in animals (or DCL1 in plants). miRNA molecules interrupt translation through precise or imprecise base-pairing with their targets. In some embodiments, a miRNA may be used as a component of a provided therapeutic construct, therapeutically or administered to a subject, such as a human patient, to treat a disease such as, e.g., cancer; alternately, in some embodiments, a nucleic acid that is complementary to the miRNA may be therapeutically administered to a subject in vivo or used in vitro to generate the desired therapeutic miRNA (e.g., miRNA-142-3p, miRNA-142-3p, miRNA-124, or miRNA-138). In this way, the complementary nucleic acid may be used as a template to generate the desired therapeutic miRNA (e.g., miRNA-142-3p, miRNA-142-3p, miRNA-124, or miRNA-138).

Additional Anti-Cancer Agent(s).

The phrase "anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic agent. In some embodiments, an anti-cancer agent is a targeted therapeutic agent. In some embodiments, an anti-cancer agent is an immune checkpoint inhibitor. In some embodiments, an anti-cancer agent is an agent identified herein having utility in methods of treating cancer. In some embodiments, an anti-cancer agent is an agent approved by the FDA or similar regulatory agency of a country other than the USA, for treating cancer.

Examples of anti-cancer agents include, but are not limited to, MEK (e.g., MEK1, MEK2, or MEK1 and MEK2) inhibitors (e.g., XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766, PD184352, SB239063, BAY 43-9006); alkylating agents such as nitrogen mustards (e.g., mechloroethamine, cyclophosphamide, uramustine, chlorambucil, melphalan, ifosfamide), ethylenimine and methylmelamines (e.g., hexamethylmelamine and thiotepa), alkyl sulfonates (e.g., busulfan and hepsulfam), nitrosoureas (e.g., carmustine, lomusitne, semustine, and streptozocin), and triazenes (e.g., decarbazine); anti-metabolites such as folic acid analogs (e.g., methotrexate, leucovorin, raltitrexed, and pemetrexed), pyrimidine analogs (e.g., fluorouracil, floxouridine, cytarabine, capecitabine, and gemcitabine), and purine analogs (e.g., mercaptopurine, thioguanine, pentostatin, fludarabine, and 5-azathioprine); plant alkaloids (e.g., vincristine, vinblastine, vinorelbine, vindesine, podophyllotoxin, paclitaxel, docetaxel, and homoharringtonine); topoisomerase inhibitors such as camptothecin derivatives (e.g., irinotecan and topotecan), amsacrine, and epipodophyllotoxins (e.g., etoposide (VP16), etoposide phosphate, and teniposide); antibiotics such as anthracenediones (e.g., mitoxantrone), anthracyclines (e.g., doxorubicin, daunorubicin, epirubicin, and fluorodaunorunicin hydrochloride), *Streptomyces*-derived antibiotics or derivatives thereof (e.g., dactinomycin, bleomycin, mitomycin, geldanamycin, plicamycin, and 17-N-allylamino-17-demethoxygeldanamycin (17-AAG; tanespimycin), clofazimine, and beta lactam derivatives; platinum-based compounds (e.g., cisplatin, oxaliplatin, carboplatin); substituted urea (e.g., hydroxyurea); methyl hydrazine derivative (e.g., procarbazine), adrenocortical suppressant (e.g., mitotane and aminoglutethimide); angiogenesis-inhibiting enzymes (e.g., L-asparaginase and arginine deiminase); PI3K inhibitors (e.g., wortmannin and LY294002); mTOR inhibitors (e.g., sertraline); DNA methyltransferase inhibitors (e.g., 5-aza-2'-deoxycytidine); antisense oligonucleotides; apoptosis gene modulators; apoptosis regulators (e.g., deoxyadenosine and triptolide); BCR/ABL antagonists; bFGF inhibitor; casein kinase inhibitors (ICOS); gallium nitrate; gelatinase inhibitors; glutathione inhibitors (e.g., etanidazole); immunostimulant peptides; insulin-like growth factor-1 receptor inhibitor; leukemia inhibiting factor; matrilysin inhibitors; matrix metalloproteinase inhibitors; MIF inhibitor; mismatched double stranded RNA; mycobacterial cell wall extract; nitric oxide modulators; phosphatase inhibitors; plasminogen activator inhibitor; proteasome inhibitors (e.g., bortezomib); protein A-based immune modulator; protein kinase C inhibitors; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors/modulators (e.g., itraconazole); single chain antigen-binding protein; stem cell inhibitor; stem-cell division inhibitors; stromelysin inhibitors; synthetic glycosaminoglycans; telomerase inhibitors; thyroid stimulating hormones; translation inhibitors; urokinase receptor antagonists; gonadotropin-releasing hormone agonists (GnRH) such as goserelin and leuprolide (leuprorelin); steroids such as adrenocorticosteroids (e.g., prednisone and dexamethasone); progestins (e.g., hydroxyprogesterone caproate, megestrol acetate, medroxyprogesterone acetate); antiprogestogens (e.g., mifepristone); estrogens (e.g., diethylstilbestrol and ethinyl estradiol); antiestrogens such as aromatase inhibitors (e.g., exemestane, fadrozole, letrozole, pentrozole, and anastrozole), selective estrogen receptor modulators (e.g., tamoxifen, tamoxifen methiodide, panomifene, and clomifene analogues); androgens (e.g., testosterone propionate and fluoxymesterone); antiandrogen (e.g., flutamide, finasteride, and bicalutamide); immunostimulants such as levamisole, interleukins (e.g., interleukin-2) and interferons/interferon agonists (e.g., alpha-interferon); monoclonal antibodies such as anti-CD20 (e.g., rituximab), anti-HER2 (e.g., trastuzumab), anti-CD52, anti-CD25 (e.g., daclizumab), anti-HLA-DR, and anti-VEGF monoclonal antibodies); immunotoxins (e.g., anti-CD33 monoclonal antibody-calicheamicin conjugate, anti-CD22 monoclonal antibody-*Pseudomonas* exotoxin conjugate, etc.); radioimmunotherapeutic agents (e.g., anti-CD20 monoclonal antibody conjugated to $^{111}$In, $^{90}$Y, or $^{131}$I, etc.); statins (e.g., cerivastatin and pitavastatin); 5-T1B receptor agonists (e.g., 5-nonyloxytryptamine); BRAF kinase inhibitors (e.g., vemurafenib and dabrafenib); tyrosine kinase inhibitors such as inhibitors of one or more of EGFR, HER2, KDR, FLT4, EphB4, and Src (e.g., gefitinib (Iressa™), erlotinib (Tarceva™), cetuximab (Erbitux™), lapatinib (Tykerb™), panitumumab (Vectibix™) vandetanib (Caprelsa™), afatinib/BIBW2992, CI-1033/canertinib, neratinib/HKI-272, CP-724714, TAK-285, AST-1306, ARRY334543, AG-1478, dacomitinib/PF299804, OSI-420/desmethyl erlotinib, AZD8931, ARRY-380, AEE788, pelitinib/EKB-569, CUDC-101, WZ8040, WZ4002, WZ3146, AG-490, XL647, P0153035, BMS-599626, sorafenib, imatinib (Gleevec®), sunitinib, and dasatinib; immune-checkpoint inhibitors (e.g., anti-CTLA-4, anti-PD1/L1 antibodies); PLK1 inhibitors (GSK461364, B12536, Tak960, NMS-P937, B16727), mitotic kinase inhibitors, or the like, or mixtures thereof (e.g., leuprolide+estrogen+progesterone).

Additionally, the therapeutic constructs described herein can be co-administered with conventional immunotherapeutic agents including, but not limited to, immunostimulants (e.g., Bacille Calmette-Guerin (BCG), levamisole, interleukin-2, alpha-interferon, etc.), therapeutic monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-Pseudomonas exotoxin conjugate, etc.), immune-checkpoint inhibitors (e.g., anti-CTLA-4, anti-PD-1, anti-PD-L1 antibodies), and radioimmunotherapy (e.g., anti-CD20 monoclonal antibody conjugated to $^{111}$In, $^{90}$Y, or $^{131}$I, etc.). These immunotherapeutic agents can also be loaded directly onto the therapeutic constructs to enhance their therapeutic effect, reduce toxicity, and reduce administration time.

In a further embodiment, the therapeutic constructs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Pm, $^{111}$Ag, $^{111}$In $^{117m}$Sn, $^{149}$Pm, $^{153}$Sm, $^{166}$Ho, $^{177}$Lu, $^{186}$Re, $^{188}$Re, $^{211}$At and $^{212}$Bi. These radiotherapeutic agents can also be loaded directly onto the therapeutic constructs to enhance the therapeutic effect, reduce toxicity, and reduce administration time.

Targeting Moieties

One or more targeting moieties (a.k.a., targeting molecules) can be loaded into, attached to the surface of, and/or enclosed within the delivery vehicle. In embodiments, the targeting moiety is displayed on the exterior surface of the delivery vehicle. Such targeting moieties may be particularly beneficial for systemic delivery.

Exemplary target molecules include proteins, peptides, ligands, nucleic acids, lipids, saccharides, or polysaccharides that bind to one or more targets associated with an organ, tissue, cell, or extracellular matrix, or specific type of tumor or infected cell. The degree of specificity with which the delivery vehicles are targeted can be modulated through the selection of a targeting molecule with the appropriate affinity and specificity. For example, antibodies are very specific. These can be polyclonal, monoclonal, fragments, recombinant, or single chain, many of which are commercially available or readily obtained using standard techniques. T-cell specific molecules, antigens, and tumor targeting molecules can be bound to the surface of the therapeutic constructs. The targeting molecules may be conjugated to the terminus of one or more PEG chains present on the surface of the particle.

In some embodiments, the targeting moiety is an antibody or antigen binding fragment (e.g., single chain variable fragments) thereof that specifically recognizes a cell or tumor marker that is present exclusively or in elevated amounts on a target cell, such as a malignant cell (e.g., a tumor antigen). Suitable targeting molecules that can be used to direct therapeutic constructs to cells and tissues of interest, as well as methods of conjugating target molecules to nanoparticles, are known in the art. See, for example, Ruoslahti et al. (*Nat. Rev. Cancer*, 2:83-90, 2002). In certain cases, therapeutic agents can be toxic to both cancer and immune cells, resulting in suboptimal efficacy. Thus, in certain embodiments, therapeutic constructs can be conjugated with a targeting moiety to enrich the delivery of at least one mitotic kinase inhibitor and at least one immune checkpoint inhibitor to only cancer cells. Examples nonexclusively include antibodies against HER2, EGFR, PD-L1, etc. that are overexpressed on cancer cells. In some embodiments, therapeutic constructs can be conjugated with a targeting moiety to enrich the delivery of at least one mitotic kinase inhibitor and at least one immune checkpoint inhibitor to only immune cells.

Targeting molecules can also include neuropilins and endothelial targeting molecules, integrins, selectins, adhesion molecules, bone targeting molecules such as zoledronic acid and alendronic acid (e.g., to target cancer metastasized to bone), stroma, and fibroblast targeting molecules.

In some embodiments, the targeting moiety targets the therapeutic construct to antigen-presenting cells (APCs), and particularly to a subclass of APCs known as dendritic cells. Dendritic cells express a number of cell surface receptors that can mediate endocytosis. In some embodiments, therapeutic construct enhances the activity of DC to process tumor antigen. Targeted delivery to DC may be performed. Targeting exogenous antigens to internalizing surface molecules on systemically-distributed antigen presenting cells facilitates uptake of the particle and can overcomes a major rate-limiting step in the therapy.

Dendritic cell targeting molecules include monoclonal or polyclonal antibodies or fragments thereof that recognize and bind to epitopes displayed on the surface of dendritic cells. Dendritic cell targeting molecules also include ligands which bind to a cell surface receptor on dendritic cells. One such receptor, the lectin DEC-205, has been used in vitro and in mice to boost both humoral (antibody-based) and cellular (CD8 T cell) responses by 2-4 orders of magnitude (Hawiger et al., *J. Exp. Med.*, 194(6):769-79, 2001; Bonifaz et al., *J. Exp. Med.*, 196(12):1627-38 2002; Bonifaz et al., *J. Exp. Med.*, 199(6):815-24, 2004). In these reports, antigens were fused to an anti-DEC205 heavy chain and a recombinant antibody molecule was used for immunization.

A variety of other endocytic receptors, including a mannose-specific lectin (mannose receptor) and IgG Fc receptors, have also been targeted in this way with similar enhancement of antigen presentation efficiency. Other suitable receptors which may be targeted include, but are not limited to, DC-SIGN, 33D1, SIGLEC-H, DCIR, CD11c, heat shock protein receptors and scavenger receptors. Targeting moieties for these receptors can be attached to the therapeutic constructs for their preferential uptake into immune cells that express these receptors. Example is mannose attached on the therapeutic constructs for targeted delivery to macrophages and DCs that have high levels of mannose receptors.

Other receptors which may be targeted include the toll-like receptors (TLRs). TLRs recognize and bind to pathogen-associated molecular patterns (PAMPs). PAMPs target the TLR on the surface of the dendritic cell and signals internally, thereby potentially increasing DC antigen uptake, maturation and T-cell stimulatory capacity. PAMPs conjugated to the particle surface or co-encapsulated include unmethylated CpG DNA (bacterial), double-stranded RNA (viral), lipopolysaccharide (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

Targeting molecules can be covalently bound to delivery vehicles using a variety of methods known in the art. In preferred embodiments the targeting moiety is attached to the delivery vehicle by PEGylation or a biotin-avidin bridge.

CD40 Agonist.

In a particular embodiment, the targeting moiety targets CD40. The moiety can be a CD40 agonist. The cell surface molecule CD40 is a member of the tumor necrosis factor receptor superfamily and is broadly expressed by immune, hematopoietic, vascular, epithelial, and other cells, including a wide range of tumor cells. As a potential target for cancer therapy, CD40 may mediate tumor regression through both an indirect effect of immune activation and a direct cytotoxic effect on the tumor, resulting in a "two-for-one" mechanism of action of CD40 agonists. CD40 agonists are known in the art and reviewed in Vonderheide (*Clin Cancer Res,* 13(4): 1083-1088, 2007). Exemplary agonists include recombinant CD40L (recombinant human trimer), CD-870, 893 (fully human IgG2 mAb), SGN-40 (humanized IgG1), and HCD 122 (fully human IgG1 mAb). Soluble agonistic CD40 antibodies have been shown to substitute for T-cell help provided by CD4+ lymphocytes in murine models of T cell-mediated immunity (Khalil et al., *Update Cancer Ther.,* 2:61-65, 2007).

Integrin Ligand.

In another embodiment, the targeting moiety is a ligand for an integrin. Studies show that integrins are overexpressed on the surface of tumor cells and can thus serve as a marker that distinguishes between tumor cells and normal cells. Certain integrins also activate TGF-β through an extracellular pathway. After latent TGF-β is released from a tumor cell, it binds with integrin on the surface of the tumor cell, leading to the activation of the latent TGF-β. Increased TGF-β concentrations in the tumor microenvironment support immune suppression and recruit regulatory T cells to the tumor environment.

RGD peptide can serve a dual function: it is not only a typical integrin-targeting ligand (Ruoslahti et al., *Annu. Rev. Cell Dev. Biol.,* 12:697-715, 1996) but also serves as an immune danger signal, activating APCs (Altincicek et al., *Biol Chem.,* 390, 1303-11, 2009). Therefore, in a preferred embodiment, RGD peptide is loaded into, attached to the surface of, and/or enclosed within the delivery vehicle.

T Cell Receptor that Recognizes the p53 Antigen.

In a particular embodiment, the targeting moiety is a T cell receptor (TCR) that recognizes the p53 antigen within the context of human MHC. T cell receptor recombinant proteins derived from bacterial, eukaryotic or yeast cells including T cell receptors composed of the alpha, beta chains or gamma/delta chains (α/β TCR or γ/Δ, TCRs).

IL-15/IL-15Rα.

In another embodiment, the targeting moiety is an IL-15/IL-15Ra complex. Interleukin-15 (IL-15) is a cytokine that shares certain receptor subunits with IL-2 and thus has some overlapping mechanisms of action. IL-15 is expressed by dendritic cells and provides a critical signal for the proliferation and priming of natural killer (NK) cells. Accordingly, IL-15/IL-15Rα complex can be used to target nanoparticulate compositions to, for example, natural killer (NK) cells.

(V) DELIVERY SYSTEMS

Embodiments of the herein-provided therapeutic constructs are agnostic as to the delivery system employed for co-delivery of at least one mitotic kinase inhibitor and at least one immune checkpoint inhibitor. Thus, in various embodiments, the delivery system can use or be based on any type of known or to-be-developed particulate delivery vehicle. These include nanoparticles, fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, calcium phosphate particles, aluminum salt particles, carbon nanotube peapods, carbon nanohorns, carbon nanohorn peapods, liposomes, lipid-based nanoparticles, lipoplex, polymeric nanoparticles, polyplex, nanoshells, dendrimers, microparticles, quantum dots, superparamagnetic nanoparticles, nanorods, cellulose nanoparticles, glass and polymer micro- and nano-spheres, biodegradable PLGA micro- and nano-spheres, gold nanoparticles, silver nanoparticles, carbon nanoparticles, iron nanoparticles, porous and non-porous silica nanoparticles, and modified micelles. Hybrid particles that consist of several classes of materials can also be used. Particles in nanometer and micron sizes can be used. Therapeutic agents, adjuvants, and any additional compounds can be included with the delivery agent by any suitable means, e.g., loaded into, attached to the surface of, coupled to, enclosed within, or contained within the delivery system. Such agents may be encapsulated, covalently bound, or non-covalently bound (e.g., by electrostatic, hydrophobic, van der Waals, or compound-specific interaction (such nucleic acid base pairing, ligand-receptor, antibody-antigen, biotin-avidin, etc.))

In some embodiments, the delivery system includes a mesoporous silica nanoparticle (MSNP), such as those described in U.S. Patent Publication No. US2017/0172923 and No. 2017/0173169, the MSNPs of which are hereby incorporated by reference.

In some embodiments, the mean particle size of the mesoporous nanoparticle (or a different nanoparticle) is about 5 nm to about 200 nm, about 5 nm to about 90 nm, about 5 nm to about 20 nm, about 30 nm to about 100 nm, about 30 nm to about 80 nm, about 30 nm to about 60 nm, about 40 nm to about 80 nm, about 70 nm to about 90 nm, or about 5 nm, about 10 nm, about 20 nm, about 30 nm, about 40 nm, about 50 nm, about 60 nm, about 70 nm, about 80 nm, about 90 nm, or about 100 nm. In some embodiments, the mesoporous silica nanoparticle is coated with cationic polymers or other compounds. The cationic polymer may bind to the surface of the nanoparticle using any appropriate means. In some embodiments, the cationic polymer binds to the nanoparticle via electrostatic interaction. The cationic polymer may be any polymer with a positive charge, such as, but not limited to, PEI, polyamidoamine, poly(allylamine), poly(diallyldimethylammonium chloride), chitosan, poly(N-isopropyl acrylamide-co-acrylamide), poly (N-isopropyl acrylamide-co-acrylic acid), poly(L-lysine), diethylaminoethyl-dextran, poly-(N-ethyl-vinylpyridinium bromide), poly(dimethylamino)ethyl methacrylate), or poly (ethylene glycol)-co-poly(trimethylaminoethylmethacrylate chloride). Other cationic polymers will be apparent to those of skill in the art, and may be found, for example, in Polymer Handbook, 4th Edition, Edited by: Brandrup, E. H. Immergut, and E. A. Grukle; John Wiley & Sons, 2003).

The cationic polymers may be linear or branched. In some embodiments, the cationic polymers may range in size from about 500 Da to 25 kDa and may be branched or linear. For example, branched PEI with an average size of 1.8 kDa to 10 kDa may be loaded onto the nanoparticle core. The ratio of cationic polymer to nanoparticle may be varied depending on the desired result. The cationic polymer may be present at 1 to 50 wt. % of the nanoconstruct, e.g., 5 to 40 wt. %, 10 to 30 wt. %, 20 to 30 wt. %, 5 to 15 wt. %, 5 to 20 wt. %, 5 to 25 wt. %, 5 to 30 wt. %, 10 to 20 wt. %, 10 to 25 wt. %, or 25 to 40 wt. %, e.g., about 5, 10, 15, 20, 25, 30, or 35 wt. %. In some embodiments, the cationic polymer is present at 10 to 20 wt. %.

In some embodiments, the cationic polymer is cross-linked, e.g., with a cleavable disulfide bond, pre- or post-coating on the nanoparticle. In some embodiments, the attached cationic polymer is crosslinked after binding to the nanoparticles, e.g., MSNP, using, for example, DSP (dithiobis[succinimidyl propionate]), DTSSP (3,3'-dithiobis (sulfosuccinimidyl propionate), and DTBP (dimethyl 3,3'-dithiobispropionimidate). The crosslinking may occur in the absence or presence of free cationic polymer in solution. In other embodiments, the cationic polymer is not crosslinked.

A stabilizer may be conjugated to the MSNP (or a different nanoparticle) and/or the cationic polymer, e.g., by any appropriate means. In some embodiments, a stabilizer is conjugated to an amine or other reactive group of a cross-linked cationic polymer coated on the nanoparticle (e.g., a MSNP). Exemplary stabilizers include, but are not limited to, PEG, dextran, polysialic acid, hyaluronic acid, polyvinyl pyrrolidone, polyvinyl alcohol, and polyacrylamide, or a combination thereof.

A stabilizer may have multiple chemically reactive groups, e.g., for attachment to the nanoparticle, cationic polymer, and/or other component. For example, a reactive stabilizer, e.g., a PEG derivative, may have two electrophilic moieties, such as maleimide-PEG-N-hydroxysuccinimidyl ester (Mal-PEG-NHS), which contains both a Michael acceptor and an activated ester. The stabilizer, e.g., PEG, used in conjunction with the compositions and methods of the invention generally has a molecular weight ranging between 500 Da-40 kDa, e.g., 2-10 kDa. The stabilizer may be present at 1 to 50 wt. % of the nanoconstruct, e.g., 5 to 30 wt. %, 10 to 20 wt. %, 10 to 25 wt. %, 5 to 15 wt. %, 5 to 20 wt. %, 5 to 25 wt. %, or 1 to 10 wt. %, e.g., about 5, 10, 15, 20, 25, 35, 40 or 45 wt. %.

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean hydrodynamic particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% of the distribution lies within 15% of the median particle size, more preferably within 10% of the median particle size, most preferably within 5% of the median particle size.

"Nanoparticle", as used herein, generally refers to a particle having a diameter from about 5 nm up to, but not including, about 1 micron, preferably from 20 nm to about 1 micron. The particles can have any shape. Nanoparticles having a spherical shape are generally referred to as "nanospheres". The present invention is not limited to specific types or kinds of nanoparticles for complexing with at least one mitotic kinase inhibitor and at least one immune checkpoint inhibitor configured for treating or preventing cancer and related hyperproliferative disorders.

Examples of nanoparticles include fullerenes (a.k.a. $C_{60}$, $C_{70}$, $C_{76}$, $C_{80}$, $C_{84}$), endohedral metallofullerenes (EMI's), which contain additional atoms, ions, or clusters inside their fullerene cage), trimetallic nitride templated endohedral metallofullerenes (TNT EMEs, high-symmetry four-atom molecular cluster endohedrals, which are formed in a trimetallic nitride template within the carbon cage), single-walled and multi-walled carbon nanotubes, branched and dendritic carbon nanotubes, gold nanorods, silver nanorods, single-walled and multi-walled boron/nitrate nanotubes, carbon nanotube peapods (nanotubes with internal metallo-fullerenes and/or other internal chemical structures), carbon nanohorns, carbon nanohorn peapods, lipid particles liposomes, lipoplex, polymeric nanoparticles, polyplex, nanoshells, dendrimers, quantum dots, superparamagnetic nanoparticles, nanorods, and cellulose nanoparticles. Other exemplary nanoparticles include glass and polymer micro- and nano-spheres, biodegradable PLGA micro- and nano-spheres, gold, silver, platinum, carbon, and iron nanoparticles.

In some embodiments, the nanoparticle is a modified micelle. In these embodiments, the modified micelle comprises polyol polymers modified to contain a hydrophobic polymer block. The term "hydrophobic polymer block" as used in the present disclosure indicates a segment of the polymer that on its own would be hydrophobic. The term "micelle" as used herein refers to an aggregate of molecules dispersed in a liquid. A typical micelle in aqueous solution forms an aggregate with the hydrophilic "head" regions in contact with surrounding solvent, sequestering the hydrophobic single tail regions in the micelle center. In some embodiments the head region may be, for example, a surface region of the polyol polymer while the tail region may be, for example, the hydrophobic polymer block region of the polyol polymer.

The invention further encompasses use of particles on the micrometer scale in addition to the nanometer scale. Where microparticles are used, it is preferred that they are relatively small, on the order of 1-50 micrometers. For ease of discussion, the use herein of "nanoparticles" encompasses true nanoparticles (sizes of from about 1 nm to about 1000 nm), microparticles (e.g., from about 1 micrometer to about 50 micrometers), or both.

Examples of nanoparticles include, by way of example and without limitation, paramagnetic nanoparticles, superparamagnetic nanoparticles, metal nanoparticles, fullerene-like materials, inorganic nanotubes, dendrimers, dendrimers with covalently attached metal chelates, nanofibers, nanohorns, nano-onions, nanorods, nanoropes, and quantum dots. In some embodiments, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles. Hybrid particles that consist of several classes of materials can also be used.

Therapeutic construct-containing compositions including at least one mitotic kinase inhibitor and at least one immune checkpoint inhibitor each loaded into, attached to the surface of, and/or enclosed within a delivery vehicle, are disclosed. The nanoparticulate compositions offer a number of advantages over delivering the active agent or agents to the target cells in solution. For example, the nanoparticulate compositions present a localized concentration of the one or more active agents on or in a nanoparticle leading to increased avidity when the nanoparticle encounters the target cells.

The nanoparticulate compositions can also serve as a depot of active agent with tunable release kinetics that can extend over several days to prolong effective systemic half-life and efficacy of the agent or agents.

Typically, two or more active agents (including at least one mitotic kinase inhibitor and at least one immune checkpoint inhibitor) are loaded into, attached to the surface of, and/or enclosed within a delivery vehicle. The relative concentrations of each of the two or more active agents and their location on or within the delivery vehicle can be manipulated during manufacture of the compositions to adapt a preferred dosage and presentation that will be received by the target cell. Loading of two or more active agents into or onto the same delivery vehicle allows the two or more active agents to be presented to the target cell or same tumor microenvironment simultaneously or in an otherwise predetermined order to the target cell.

The delivery vehicles can be, for example, nanolipogels, polymeric particles, silica particles, liposomes, or multilamellar vesicles. In the certain embodiments, the particulate delivery vehicles are nanoscale compositions, for example, 10 nm up to, but not including, about 1 micron. However, it will be appreciated that in some embodiments, and for some uses, the particles can be smaller, or larger (e.g., microparticles, etc.). Although example therapeutic constructs disclosed herein may be referred to nanoparticulate compositions, it will be appreciated that in some embodiments and for some uses the particulate compositions can be somewhat larger than nanoparticles. For example, particulate compositions can also be between about 1 micron to about 1000 microns. Such compositions can be referred to as microparticulate compositions.

In embodiments for treating cancer it is desirable that the particle be of a size suitable to access the tumor microenvironment. In particular embodiments, the particle is of a size suitable to access the tumor microenvironment and/or the tumor cells by enhanced permeability and retention (EPR) effect. EPR refers to the property by which certain sizes of molecules (e.g., the particulate compositions discussed herein) tend to accumulate in tumor tissue much more than they do in normal tissues. Therefore, in compositions for treatment of cancer, the delivery vehicle is preferably in the range of about 25 nm to about 500 nm inclusive, more preferably in the range of about 30 nm to about 300 nm inclusive.

Nanolipogels.

Nanolipogels are core-shell nano-particulates that combine the advantages of both liposomes and polymer-based particles for sustained delivery of active agents. In some of these embodiments and applications nanolipogels can exhibit, increased loading efficiency, increased sustained release, and improved therapeutic efficacy for combinations of macromolecules and molecules compared to conventional nanoparticle compositions.

Typically, the outer shell of the nanolipogel protects cargo and, provides biocompatibility as well as a surface for functionalization with targeting molecule(s). The outer shell encapsulates components so they are not exposed until desired, for example, in response to environmental conditions or stimuli, creating monodisperse, reproducible particle populations, and mediating internalization into desired cell types. The inner core, which can be a dendrimer or other polymer, has separate and additive functionalities to the outer shell. For example, the inner shell allows for secondary deposition of drug, vaccine, or imaging agent; increases loading of components with different physiochemical properties into the particle; allows for tunable release of contents from particles; increases cytosolic availability of DNA/RNA, drug, and/or protein by disrupting endosomes, all leading to enhanced drug effects, antigen presentation, and transfection/silencing Nanolipogels have a polymer matrix core containing one or more host molecules. The polymeric matrix is preferably a hydrogel, such as a crosslinked block copolymer containing one or more poly(alkylene oxide) segments, such as polyethylene glycol, and one or more aliphatic polyester segments, such as polylactic acid. One or more cargo molecules is dispersed within or covalently bound to the polymeric matrix. The hydrogel core is surrounded by a liposomal shell.

Nanolipogels can be constructed to incorporate a variety of active agents that can subsequently be released in a controlled fashion. Active agents can be dispersed within the hydrogel matrix, dispersed within the liposomal shell, covalently attached to the liposomal shell, and combinations thereof. Active agents can be selectively incorporated at each of these locales within the nanolipogel. Furthermore, the release rate of active agents from each of these locales can be independently tuned. Because each of these locales possesses distinct properties, including size and hydrophobicity/hydrophilicity, the chemical entities independently incorporated at each of these locales can differ dramatically with respect to size and composition. For example, nanolipogels can be loaded with one or more compounds dispersed within the polymeric matrix as well as at least one mitotic kinase inhibitor and at least one immune checkpoint inhibitor. Nanolipogels can be loaded provide simultaneous sustained release of agents that differ widely in chemical composition and molecular weight.

Nanolipogels are typically spherical in shape, with average particle sizes ranging between about 50 nm and about 1000 nm, more preferably between about 75 nm and about 300 nm, most preferably between about 90 nm and about 200 nm. In certain embodiments, the nanolipogels possess an average particle size between about 100 nm and about 140 nm. Particles may be non-spherical.

Depending upon the nature of the lipids present in the liposomal shell of the nanolipogels, nanolipogels having a positive, negative, or near neutral surface charge may be prepared. In certain embodiments, the nanolipogels possess a near neutral surface charge. In certain embodiments, the nanolipogels possess a ζ-potential of between about 10 mV and about −10 mV, more preferably between about 5 mV and about −5 mV, more preferably between about 3 mV and about −3 mV, most preferably between about 2 mV and about −2 mV.

Hydrophobic active agents, such as proteins, may be covalently connected to the surface of the nanolipogel, whereas hydrophilic active agents may be covalently connected to the surface of the nanolipogel or dispersed within the liposomal shell. In certain embodiments, the liposomal shell includes one or more PEGylated lipids. In these cases, one or more active agents may be conjugated to the terminus of one or more PEG chains present on the surface of the liposomal shell.

In another embodiment, the lipid is modified to include an avidin moiety, enabling a biotinylated targeting moiety, detectable label, or other active agent to be coupled thereto, if so desired.

In particular embodiments, one or more active agents are covalently connected to the surface of the nanolipogel via a linking group that is cleaved in response to an external Core.

The nanolipogel core is formed from a polymeric matrix. The matrix can include one or more host molecules as discussed in more detail below. The nanolipogel core may further include one or more active agents. The active agents may be complexed to a host molecule, dispersed with polymeric matrix, or combinations thereof.

The polymeric matrix of the nanolipogels may be formed from one or more polymers or copolymers. By varying the composition and morphology of the polymeric matrix, one can achieve a variety of controlled release characteristics, permitting the delivery of moderate constant doses of one or more active agents over prolonged periods of time.

The polymeric matrix may be formed from non-biodegradable or biodegradable polymers; however, preferably, the polymeric matrix is biodegradable. The polymeric matrix can be selected to degrade over a time period ranging from one day to one year, more preferably from seven days to 26 weeks, more preferably from seven days to 20 weeks, most preferably from seven days to 16 weeks. Biodegradable cross-linkers may be used to increase molecular weight of polymers, which are clearable from the body as small fragments after degradation of the cross-linkers.

In general, synthetic polymers are preferred, although natural polymers may be used. Representative polymers include poly(hydroxy acids) such as poly(lactic acid), poly(glycolic acid), poly(lactic acid-co-glycolic acids), polyhydroxyalkanoates such as poly3-hydroxybutyrate or poly4-hydroxybutyrate; polycaprolactones; poly(orthoesters); polyanhydrides; poly(phosphazenes); poly(lactide-co-caprolactones); poly(glycolide-co-caprolactones); polycarbonates such as tyrosine polycarbonates; polyamides (including synthetic and natural polyamides), polypeptides, and poly(amino acids); polyesteramides; other biocompatible polyesters; poly(dioxanones); poly(alkylene alkylates); hydrophilic polyethers; polyurethanes; polyetheresters; polyacetals; polycyanoacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), polyvinyl alcohols, polyvinylpyrrolidone; poly(alkylene oxides) such as polyethylene glycol (PEG); derivatized celluloses such as alkyl celluloses (e.g., methyl cellulose), hydroxyalkyl celluloses (e.g., hydroxypropyl cellulose), cellulose ethers, cellulose esters, nitrocelluloses, polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), as well as derivatives, copolymers, and blends thereof.

As used herein, "derivatives" include polymers having substitutions, additions of chemical groups and other modifications to the polymeric backbones described above routinely made by those skilled in the art. Natural polymers, including proteins such as albumin, collagen, gelatin, prolamines, such as zein, and polysaccharides such as alginate and pectin, may also be incorporated into the polymeric matrix. While a variety of polymers may be used to form the polymeric matrix, generally, the resulting polymeric matrix will be a hydrogel. In certain cases, when the polymeric matrix contains a natural polymer, the natural polymer is a biopolymer which degrades by hydrolysis, such as a polyhydroxyalkanoate.

The polymeric matrix may optionally contain one or more crosslinkable polymers. Preferably, the crosslinkable polymers contain one or more photo-polymerizable groups, allowing for the crosslinking of the polymeric matrix following nanolipogel formation. Examples of suitable photo-polymerizable groups include vinyl groups, acrylate groups, methacrylate groups, and acrylamide groups. Photo-polymerizable groups, when present, may be incorporated within the backbone of the crosslinkable polymers, within one or more of the sidechains of the crosslinkable polymers, at one or more of the ends of the crosslinkable polymers, or combinations thereof.

The polymeric matrix may be formed from polymers having a variety of molecular weights, so as to form nanolipogels having properties, including drug release rates, optimal for specific applications. Generally, the polymers which make up the polymeric matrix possess average molecular weights ranging between about 500 Da and 50 kDa. In cases where the polymeric matrix is formed from non-crosslinkable polymers, the polymers typically possess average molecular weights ranging between about 1 kDa and about 50 kDa, more preferably between about 1 kDa and about 70 kDa, most preferably between about 5 kDa and about 50 kDa. In cases where the polymeric matrix is formed from crosslinkable polymers, the polymers typically possess lower average molecular weights ranging between about 500 Da and about 25 kDa, more preferably between about 1 kDa and about 10 kDa, most preferably between about 3 kDa and about 6 kDa. In particular embodiments the polymeric matrix is formed from a crosslinkable polymer having an average molecular weight of about 5 kDa.

In some embodiments, the polymeric matrix is formed from a poly(alkylene oxide) polymer or a block copolymer containing one or more poly(alkylene oxide) segments. The poly(alkylene oxide) polymer or poly(alkylene oxide) polymer segments may contain between 8 and 500 repeat units, more preferably between 40 and 300 repeat units, most preferably between 50 and 150 repeat units. Suitable poly(alkylene oxides) include polyethylene glycol (also referred to as polyethylene oxide or PEG), polypropylene 1,2-glycol, poly(propylene oxide), polypropylene 1,3-glycol, and copolymers thereof.

In some embodiments, the polymeric matrix is formed from an aliphatic polyester or a block copolymer containing one or more aliphatic polyester segments. Preferably the polyester or polyester segments are poly(lactic acid) (PLA), poly(glycolic acid) PGA, or poly(lactide-co-glycolide) (PLGA).

In some embodiments, the polymeric matrix is formed from a block copolymer containing one or more poly(alkylene oxide) segments, one or more aliphatic polyester segments, and optionally one or more photo-polymerizable groups. In these cases, the one or more poly(alkylene oxide) segments imbue the polymer with the necessary hydrophilicity, such that the resultant polymer matrix forms a suitable hydrogel, while the polyester segments provide a polymeric matrix with tunable hydrophobicity/hydrophilicity and/or the desired in vivo degradation characteristics.

The degradation rate of the polyester segments, and often the corresponding drug release rate, can be varied from days (in the case of pure PGA) to months (in the case of pure PLA), and may be readily manipulated by varying the ratio of PLA to PGA in the polyester segments. In addition, the poly(alkylene oxides), such as PEG, and aliphatic polyesters, such as PGA, PLA, and PLGA have been established as safe for use in humans; these materials have been used in human clinical applications, including drug delivery systems, for more than 30 years.

In certain embodiments, the polymeric matrix is formed from a tri-block copolymer containing a central poly(alkylene oxide) segment, adjoining aliphatic polyester segments attached to either end of the central poly(alkylene oxide) segment, and one or more photo-polymerizable groups. Preferably, the central poly(alkylene oxide) segment is PEG, and aliphatic polyesters segments are PGA, PLA, or PLGA.

Generally, the average molecular weight of the central poly(alkylene oxide) segment is greater than the average molecular weight of the adjoining polyester segments. In certain embodiments, the average molecular weight of the central poly(alkylene oxide) segment is at least three times greater than the average molecular weight of one of the adjoining polyester segments, more preferably at least five times greater than the average molecular weight of one of the adjoining polyester segments, most preferably at least ten times greater than the average molecular weight of one of the adjoining polyester segments.

In some cases, the central poly(alkylene oxide) segment possesses an average molecular weight ranging between about 500 Da and about 10,000 Da, more preferably between about 1,000 Da and about 7,000 Da, most preferably between about 2,500 Da and about 5,000 Da. In particular embodiments, average molecular weight of the central poly(alkylene oxide) segment is about 4,000 Da. Typically, each adjoining polyester segment possesses an average molecular weight ranging between about 100 Da and about 3,500 Da, more preferably between about 100 Da and about 1,000 Da, most preferably between about 100 Da and about 500 Da.

Examples of natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of non-biodegradable polymers include ethylene vinyl acetate, poly(meth)acrylic acid, polyamides, copolymers and mixtures thereof.

The matrix can also be made of gel-type polymers, such as alginate, produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

Perhaps the most widely used are the aliphatic polyesters, specifically the hydrophobic poly(lactic acid) (PLA), more hydrophilic poly(glycolic acid) PGA and their copolymers, poly(lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its homopolymers PGA and PLA have been established for safe use in humans; these materials have a history of over 30 years in various human clinical applications including drug delivery systems. PLGA nanoparticles can be formulated in a variety of ways that improve drug pharmacokinetics and biodistribution to target tissue by either passive or active targeting. The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly(lactic acid) (PLA), more hydrophilic poly (glycolic acid) PGA and their copolymers, poly(lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Shell Components.

Nanolipogels include a liposomal shell composed of one or more concentric lipid monolayers or lipid bilayers. The shell can further include one or more active agents, targeting molecules, or combinations thereof.

Nanolipogels include a liposomal shell composed of one or more concentric lipid monolayers or lipid bilayers. The composition of the liposomal shell may be varied to influence the release rate of one or more active agents in vivo. The lipids may also be covalently crosslinked, if desired, to alter in vivo drug release.

The lipid shell can be formed from a single lipid bilayer (unilamellar) or several concentric lipid bilayers (multilamellar). The lipid shell may be formed from a single lipid; however, in preferred embodiments, the lipid shell is formed from a combination of more than one lipid. The lipids can be neutral, anionic, or cationic at physiologic pH.

Suitable neutral and anionic lipids include sterols and lipids such as cholesterol, phospholipids, lysolipids, lysophospholipids, and sphingolipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids, such as sphingomyelin; sphingoglycolipids (also known as 1-ceramidyl glucosides), such as ceramide galactopyranoside, gangliosides and cerebrosides; fatty acids, sterols containing a carboxylic acid group such as cholesterol or derivatives thereof; and 1,2-diacyl-sn-glycero-3-phosphoethanolamines, including 1,2-dioleoyl-sn-Glycero-3-phosphoethanolamine or 1,2-dioleolylglyceryl phosphatidylethanolamine (DOPE), 1,2-dihexadecylphosphoethanolamine (DHPE), 1,2-distearoylphosphatidylcholine (DSPC), 1,2-dipalmitoylphosphatidylcholine (DPPC), and 1,2-dimyristoylphosphatidylcholine (DMPC). Also suitable are natural (e.g., tissue derived L-.alpha.-phosphatidyl:

egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of these lipids.

Suitable cationic lipids include N-[1-(2,3-dioleoyloxy)propyl]-N,N,N-trimethyl ammonium salts, also referred to as TAP lipids, for example as a methylsulfate salt. Suitable TAP lipids include, but are not limited to, DOTAP (dioleoyl-), DMTAP (dimyristoyl-), DPTAP (dipalmitoyl-), and DSTAP (distearoyl-). Other suitable cationic lipids include dimethyldioctadecyl ammonium bromide (DDAB), 1,2-diacyloxy-3-trimethylammonium propanes, N-[1-(2,3-dioloyloxy)propyl]-N,N-dimethyl amine (DODAP), 1,2-diacyloxy-3-dimethylammonium propanes, N-[1-(2,3-dioleyloxy)propyl]-N,N,N-trimethylammonium chloride (DOTMA), 1,2-dialkyloxy-3-dimethylammonium propanes, dioctadecylamidoglycylspermine (DOGS), 3-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanam-inium trifluoro-acetate (DOSPA), .beta.-alanyl cholesterol, cetyltrimethylammonium bromide (CTAB), diCu-amidine, N-tert-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide, 1-[2-(acyloxy)ethyl]2-alkyl(alkenyl)-3-(2-hydroxyethyl)-imidazolinium chloride derivatives, such as 1-[2-(9 (Z)-octadecenoyloxy)ethyl]-2-(8(Z)-heptadecenyl-3-(2-hydroxyethyl)-imidazolinium chloride (DOTIM) and 1-[2-(hexadecanoyloxy)ethyl]-2-pentadecyl-3-(2-hydroxyethyl) imidazolinium chloride (DPTIM), and 2,3-dialkyloxypropyl quaternary ammonium derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Other suitable lipids include PEGylated derivatives of the neutral, anionic, and cationic lipids described above. Incorporation of one or more PEGylated lipid derivatives into the lipid shell can result in a nanolipogel which displays polyethylene glycol chains on its surface. The resulting nanolipogels may possess increased stability and circulation time in vivo as compared to nanolipogels lacking PEG chains on their surfaces. Examples of suitable PEGylated lipids include distearoylphosphatidylethanlamine-polyethylene glycol (DSPE-PEG), including DSPE PEG (2000 MW) and DSPE PEG (5000 MW), dipalmitoyl-glycero-succinate polyethylene glycol (DPGS-PEG), stearyl-polyethylene glycol and cholesteryl-polyethylene glycol.

In certain embodiments, the lipid shell is formed from a combination of more than one lipid. In certain embodiments the lipid shell is formed from a mixture of at least three lipids. In particular embodiments, the lipid shell is formed from a mixture of phosphatidyl choline (PC), 1,2-distearoyl-sn-glycero-3-phosphoethanolamine-N-[amino(polyethylene glycol)-2000] (DSPE-PEG), and cholesterol.

In some embodiments, the lipid shell is formed from a mixture of one or more PEGylated phospholipids and one or more additional lipids or sterols. In certain instances, the molar ratio of the one or more PEGylated lipids to the one or more additional lipids or sterols ranges from about 1:1 to about 1:6, more preferably from about 1:2 to about 1:6, most preferably from about 1:3 to about 1:5. In particular embodiments, the molar ratio of the one or more PEGylated lipids to the one or more additional lipids or sterols is about 1:4.

In some embodiments, the lipid shell is formed from a mixture of one or more phospholipids and one or more additional lipids or sterols. In certain instances, the molar ratio of the one or more phospholipids to the one or more additional lipids or sterols ranges from about 1:1 to about 6:1, more preferably from about 2:1 to about 6:1, most preferably from about 3:1 to about 5:1. In particular embodiments, the molar ratio of the one or more phospholipids to the one or more additional lipids or sterols is about 4:1.

In preferred embodiments, the lipid shell is formed from a mixture of a phospholipid, such as phosphatidyl choline (PC), a PEGylated phospholipid, such as 1,2-distearoyl-sn-glycero-3-phosphoethanolamine-N-[amino(polyethylene glycol)-2000] (DSPE-PEG), and cholesterol. In particular embodiments, the lipid shell is formed from a mixture of phosphatidyl choline, 1,2-distearoyl-sn-glycero-3-phosphoethanolamine-N-[amino(polyethylene glycol)-2000] (DSPE-PEG), and cholesterol in a 3:1:1 molar ratio.

Polymeric Particles.

The delivery vehicle can also be a polymeric particle, for example a micro- or a nanoparticle. The particles can be biodegradable or non-biodegradable. Exemplary polymers that can be used to manufacture polymeric particles are discussed above with respect to the polymeric matrix component of nanolipogels.

Examples of preferred biodegradable polymers include polymers of hydroxy acids such as lactic acid and glycolic acid, and copolymers with PEG, polyanhydrides, poly(ortho)esters, polyurethanes, poly(butyric acid), poly(valeric acid), poly(lactide-co-caprolactone), blends and copolymers thereof. In preferred embodiments, the particles are composed of one or more polyesters.

For example, particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(.epsilon.-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. Alginate polymers may also be used.

In some embodiments, the particles are composed of PLGA. PLGA is a safe, FDA approved polymer. PLGA particles are advantageous because they can protect the active agent (i.e., the encapsulant), promote prolonged release, and are amenable to the addition of targeting moieties.

The particles can contain one or more polymer conjugates containing end-to-end linkages between the polymer and a targeting moiety, detectable label, or other active agent. For example, a modified polymer can be a PLGA-PEG-phosphonate. In another example, the particle is modified to include an avidin moiety and a biotinylated targeting moiety, detectable label, or other active agent can be coupled thereto.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the particles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of non-biodegradable polymers include ethylene vinyl acetate, poly(meth)acrylic acid, polyamides, copolymers and mixtures thereof.

Nanolipogels.

A nanolipogel is a nanoparticle that combines the advantages of both liposomes and polymer-based particles for sustained delivery of nucleic acids, proteins and/or small molecules. The nanolipogel can be in the form of spheres, discs, rods or other geometries with different aspect ratios. The nanosphere can be larger, i.e., microparticles. The nanolipogel is typically formed of synthetic or natural polymers capable of encapsulating agents by remote loading and tunable in properties so as to facilitate different rates of release. Release rates are modulated by varying the polymer to lipid ratio from 0.05 to 5.0, more preferably from 0.5 to 1.5.

Nanolipogels are designed to be loaded with agents either prior to, during or after formation and subsequently function as controlled-release vehicles for the agents. The nanolipogel can be loaded with more than one agent such that controlled release of the multiplicity of agents is subsequently achieved.

The nanolipogel is loaded with at least one mitotic kinase inhibitor and at least one immune checkpoint inhibitor during formation and/or following formation by the process of rehydration of the nanolipogel in the presence of the agents. For example, the nanolipogel is loaded with a molecule that serves as a mitotic kinase inhibitor and the nanolipogel thereafter incorporates one or more immune checkpoint inhibitor after formation (or vice versa), for the co-delivery and release of both inhibitors together.

Polymeric Nanoparticles

Emulsion Method.

In some embodiments, the polymeric nanoparticle is prepared using an emulsion solvent evaporation method. For example, a polymeric material is dissolved in a water immiscible organic solvent and mixed with a drug solution or a combination of drug solutions. The water immiscible organic solvent can be, but is not limited to, one or more of the following: chloroform, dichloromethane, and acyl acetate. The drug can be dissolved in, but is not limited to, one or more of the following: acetone, ethanol, methanol, isopropyl alcohol, acetonitrile and dimethyl sulfoxide (DMSO). An aqueous solution is then added into the resulting mixture solution to yield emulsion solution by emulsification. The emulsification technique can be, but is not limited to, probe sonication or homogenization through a homogenizer. The peptides or fluorophores or drugs may be associated with the surface of, encapsulated within, surrounded by, and/or distributed throughout, the polymeric matrix of the particle.

Nanoprecipitation Method.

In another embodiment, the polymeric nanoparticles are prepared using nanoprecipitation methods or microfluidic devices. A polymeric material is mixed with a drug or drug combinations in a water miscible organic solvent. The resulting mixture solution is then added to an aqueous solution to yield a nanoparticle solution.

Exemplary Methods of Preparation.

Particles can be fabricated from different polymers using a variety of methods that and can be selected based on criteria including the polymeric composition of the particle, the agent(s) being loaded into or associated with the particle according to method that are known in the art. Exemplary methods are provided below.

Solvent Evaporation.

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer. Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

Hot Melt Microencapsulation.

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting particles are washed by decantation with petroleum ether to give a free-flowing powder. Particles with sizes between 0.5 to 1000 microns are obtained with this method. The external surfaces of spheres prepared with this technique are usually smooth and dense. This procedure is used to prepare particles made of polyesters and polyanhydrides. However, this method is limited to polymers with molecular weights between 1,000-50,000.

Solvent Removal.

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

Spray-Drying.

In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=−24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

Hydrogel Particles.

Particles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The particles are left to incubate in the bath for twenty to thirty minutes in order to allow sufficient time for gelation to occur. Particle size is controlled by using various size extruders or varying either the nitrogen gas or polymer solution flow rates. Chitosan particles can be prepared by dissolving the polymer in acidic solution and crosslinking it with tripolyphosphate. Carboxymethyl cellulose (CMC) particles can be prepared by dissolving the polymer in acid solution and precipitating the particle with lead ions. In the case of negatively charged polymers (e.g., alginate, CMC), positively charged ligands (e.g., polylysine, polyethyleneimine) of different molecular weights can be ionically attached.

Other Delivery Vehicles

In some embodiments, the delivery vehicles are liposomes or lipid nanoparticles. Liposomes are typically spherical vesicles composed of a lamellar phase lipid bilayer. The liposomes can be, for example, multilamellar vesicles (MLV), small unilamellar liposome vesicles (SUV), large unilamellar vesicles (LUV), or cochleate vesicles. Liposomes, micelles, and other lipid-based delivery vehicles useful for preparation of the disclosed nanoparticulate compositions are known in the art. See, for example, Torchilin et al. (*Adv Drug Delivery Rev,* 58(14):1532-55, 2006). It is anticipated that a wide variety of liposomes and exosomes may be used with the present invention. Liposomes may comprise N-[1-(2,3-Dioleoyloxy)propyl]-N,N,N-trimethyl-ammonium methyl-sulfate (DOTAP) or Lipofectamine™ In some embodiments, a delivery system involving chitosan may be used as described, e.g., in Lu et al. (*Cancer Cell,* 18:185-197, 2010). In some embodiments, a nanovector may be used to deliver a miRNA to a subject; nanovectors are described, e.g., in Pramanik et al. (*Mol Cancer Ther,* 10:1470-1480, 2011).

The delivery vehicle can also be silica particles. Suitable silica particles useful for preparation of the disclosed nanoparticulate compositions are also known in the art. See, for example, Barbe et al. (*Adv Materials,* 16(21):1959-1966, 2004), Ngamcherdtrakul et al. (*Adv Func Materials,* 25: 2646-2659, 2015) and Argyo et al. (*Chem. Mater.,* 26(1): 435-451, 2014). For example, in some embodiments, a silicone nanoparticle (e.g., as described in Bharali et al. *PNAS,* 102(32): 11539-11544, 2005) may be used to deliver at least one mitotic kinase inhibitor and at least one immune checkpoint inhibitor to a cell. Solubility of silica or silicon in the body provides the ability for time-release of the agents that the particles carry. In addition, biodegradable polymers or bioreducible crosslinking agents can be used to modify the silica or silicon particles to provide the time-release ability.

(VI) ANTIBODIES

At least some of the agents herein (such as agents used to induce immune checkpoint blockade) are antibodies. An antibody is a type of binding agent, which is a molecule that can bind a target ligand, for instance on the surface of a cell or in a biological sample. The term antibody includes both whole antibodies and functional (that is, maintaining significant and specific target binding) fragments thereof. The terms "antibody" and "immunoglobulin" are used interchangeably herein and are well understood by those in the field. Those terms refer to a protein including one or more polypeptides that specifically binds an antigen. One form of antibody includes the basic structural unit of an antibody. This form is a tetramer and includes two pairs of antibody chains, each pair having one light and one heavy chain. In each pair, the light and heavy chain variable regions are together responsible for binding to the antigen recognized by that antibody, and the constant regions are responsible for the antibody effector functions.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of 25 kDa or 214 amino acids) include a variable region of 110 amino acids at the NH2-terminus and a kappa or lambda constant region at the COOH-terminus. Full-length immunoglobulin "heavy chains" (of 50 kDa or 446 amino acids), similarly include a variable region (of 116 amino acids) and one of the aforementioned heavy chain constant regions, e.g., gamma (of 330 amino acids).

Particular embodiments of antibodies and immunoglobulins include antibodies or immunoglobulins of any isotype, fragments of antibodies which retain specific binding to antigen, including, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, a fluorescent molecule, or a stable elemental isotope and the like. The antibodies may be further conjugated to other moieties, such as members of specific binding pairs, e.g., biotin (member of a biotin-avidin specific binding pair), and the like. Also encompassed by the term are Fab', Fv, F(ab')$_2$, and other antibody fragments that retain specific binding to their cognate antigen, and monoclonal antibodies.

Antibodies may exist in a variety of other forms including, for example, bi-functional (i.e. bi-specific) hybrid antibodies (e.g., Lanzavecchia et al., *Eur. J. Immunol.* 17: 105, 1987) and in single chains (e.g., Huston et al., *Proc. Natl. Acad. Sci. U.S.A.* 85: 5879-5883, 1988; and Bird et al., *Science* 242: 423-426, 1988). See, generally, Hood et al. (1984) "Immunology", N.Y., 2nd ed., and Hunkapiller & Hood (*Nature* 323: 15-16, 1986).

An immunoglobulin light or heavy chain variable region consists of a "framework" region (FR) interrupted by three hypervariable regions, also called "complementarity determining regions" or "CDRs". The extent of the framework region and CDRs has been precisely defined (see, "Sequences of Proteins of Immunological Interest" E. Kabat et al. (1991) US Department of Health and Human Services). In particular embodiments, the numbering of an antibody amino acid sequence can conform to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as γ1 and γ3.

(VII) PHARMACEUTICAL COMPOSITIONS AND ADMINISTRATION FORMULATIONS

Provided herein are compositions for use in treating cancer, precancer, and other proliferative disease. The compositions include at least two active components/agents, one of which is a therapeutically active agent that inhibits at least one mitotic kinase inhibitor; and another of which is an immune checkpoint inhibitor. As described herein, the active agents may be delivered in/associated with a delivery vehicle (a construct, an engineered construct), such as a liposome, an organic or inorganic (nano- or micro-) particle, and so forth. As described herein, the active agents may be co-delivered with a chemical linker connecting the agents (e.g., an antibody-drug conjugate, an antibody-oligonucleotide conjugate, a small molecule-oligonucleotide conjugate, or a small molecule-small molecule conjugate).

The compositions can be provided to the cells either directly, such as by contacting it with the cell, or indirectly, such as through the action of any biological process. For example, the compositions can be formulated in a physiologically acceptable carrier or vehicle, and injected into a tissue or fluid surrounding the cell. The compositions can cross the cell membrane by simple diffusion, endocytosis, or by any active or passive transport mechanism.

When formulated in a pharmaceutical composition, a therapeutic compound (such as delivery system coupled with at least one mitotic kinase inhibitor and at least one immune checkpoint inhibitor) can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human or veterinary subject.

The term "pharmaceutically acceptable derivative" as used herein means any pharmaceutically acceptable salt, solvate or prodrug, e.g. ester, of the desired active agent, which upon administration to the recipient is capable of providing (directly or indirectly) the desired active agent, or an active metabolite or residue thereof. Such derivatives are recognizable to those skilled in the art, without undue experimentation. Nevertheless, reference is made to the teaching of Burgers Medicinal Chemistry and Drug Discovery, 5th Edition, Vol 1: Principles and Practice. Pharmaceutically acceptable derivatives include salts, solvates, esters, carbamates, and phosphate esters.

While it is possible to use a composition for therapy as is, it may be preferable to administer it in a pharmaceutical formulation, e.g., in admixture with a suitable pharmaceutical excipient, diluent or carrier selected with regard to the intended route of administration and standard pharmaceutical practice. Accordingly, in one aspect, pharmaceutical composition or formulation includes at least one active composition, or a pharmaceutically acceptable derivative thereof, in association with a pharmaceutically acceptable excipient, diluent and/or carrier. The excipient, diluent and/or carrier is "acceptable" in the sense of being compatible with the other ingredient(s) of the formulation and not significantly deleterious to the recipient thereof.

Any composition formulation disclosed herein can advantageously include any other pharmaceutically acceptable carriers which include those that do not produce significantly adverse, allergic, or other untoward reactions that outweigh the benefit of administration, whether for research, prophylactic and/or therapeutic treatments. Exemplary pharmaceutically acceptable excipients, diluents, and carriers for therapeutic use are well known in the pharmaceutical art, and are described, for example, in Remington: The Science and Practice of Pharmacy. Lippincott Williams & Wilkins (A. R., Gennaro edit. 2005), and in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies. The pharmaceutical excipient(s), diluent(s), and carrier(s) can be selected with regard to the intended route of administration and standard pharmaceutical practice.

Such pharmaceutical formulations may be presented for use in a conventional manner with the aid of one or more suitable excipients, diluents, and carriers. Pharmaceutically acceptable excipients assist or make possible the formation of a dosage form for a bioactive material and include diluents, binding agents, lubricants, glidants, disintegrants, coloring agents, and other ingredients. Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used. An excipient is pharmaceutically acceptable if, in addition to performing its desired function, it is non-toxic, well tolerated upon ingestion, and does not interfere with absorption of bioactive materials.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol, or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers, or polysaccharides.

A "therapeutically effective amount" or "therapeutically effective dose" means the amount of a compound that, when administered to a subject for treating a state, disorder or condition, is sufficient to effect such state, disorder, or condition. The "therapeutically effective amount" will vary depending on the compound, the disease and its severity and the age, weight, physical condition and responsiveness of the mammal to be treated. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). In certain cases, "therapeutically effective amount" is used to mean an amount or dose sufficient to modulate, e.g., increase or decrease a desired activity e.g., by 10%, by 50%, or by 90%. Generally, a therapeutically effective amount is sufficient to cause an improvement in a clinically significant condition in the host following a therapeutic regimen involving one or more therapeutic agents. The concentration or amount of the active ingredient depends on the desired dosage and administration regimen, as discussed herein.

The actual dose amount administered to a particular subject can be determined by a physician, veterinarian, or researcher taking into account parameters such as physical, physiological and psychological factors including target, body weight, stage of cancer, the type of cancer, previous or concurrent therapeutic interventions, idiopathy of the subject, and route of administration.

Amounts effective for this use will depend on the severity of the disease and its location, particularly when a metastatic site is implicated, and the weight and general state of the patient being treated. Generally dosages range from 0.01 mg/kg to 100 mg/kg host body weight of therapeutic construct per day, with dosages of from 0.1 mg/kg to 10 mg/kg per day being more commonly used, and for instance dosages of 3-7 mg/kg. Maintenance dosages over a prolonged period of time may be adjusted as necessary. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The selected dosage may be influenced by the desired therapeutic effect, the route of administration, the duration of the treatment desired, and the specific therapeutic complex being employed. Generally, therapeutic construct can be administered in a range of about 0.001 mg/kg to 100 mg/kg per administration (e.g., daily; or 2, 3, 4, 5 or more times weekly; or 2, 3, 4, 5 or more times a month, etc., as discussed in more detail below). The route of administration can be a consideration in determining dosage as well. For example, in a particular embodiment, a therapeutic construct is administered in a range of 0.01 mg/kg to 100 mg/kg (e.g., daily; or 2, 3, 4, 5 or more times weekly; or 2, 3, 4, 5 or more times a month, etc.) by intravenous or interpretational routes, or in a range of 0.0001 mg/kg to 1 mg/kg (e.g., daily; or 2, 3, 4, 5 or more times weekly; or 2, 3, 4, 5 or more times a month, etc.) for a subcutaneous route (e.g., local injection into or adjacent to a tumor or into the TME). More exemplary dosages are discussed below.

Suitable dosages may range from 0.01 mg/kg to 100 mg/kg of body weight per day, week, or month. Exemplary doses can include 0.05 mg/kg to 10.0 mg/kg of the active compounds (therapeutic constructs) disclosed herein. The total daily dose can be 0.05 mg/kg to 30.0 mg/kg of an agent administered to a subject one to three times a day, including administration of total daily doses of 0.05-3.0, 0.1-3.0, 0.5-3.0, 1.0-3.0, 1.5-3.0, 2.0-3.0, 2.5-3.0, and 0.5-3.0 mg/kg/day of administration forms of a drug using 60-minute oral, intravenous or other dosing. In one particular example, doses can be administered QD or BID to a subject with, e.g., total daily doses of 1.5 mg/kg, 3.0 mg/kg, 4.0 mg/kg, 5.0 mg/kg, or 7.5 mg/kg of a composition with up to 92-98% wt/v of the compounds disclosed herein.

Additional useful doses can often range from 0.1 to 5 µg/kg or from 0.5 to 1 µg/kg. In other examples, a dose can include 1 µg/kg, 10 µg/kg, 20 µg/kg, 40 µg/kg, 80 µg/kg, 200 µg/kg, 0.1 to 5 mg/kg or from 0.5 to 1 mg/kg. In other examples, a dose can include 1 mg/kg, 10 mg/kg, 20 mg/kg, 40 mg/kg, 80 mg/kg, 200 mg/kg, 400 mg/kg, 450 mg/kg, or more.

Therapeutic materials of the present disclosure may be employed in serious disease states, that is, life-threatening or potentially life threatening situations. In such cases, it is possible and may be felt desirable by the treating physician to administer substantial excesses of these compositions.

As will be appreciated by those of skill in the art, specific dosages will be influenced by the pharmacokinetics of the active compound. For administration, therapeutically effective amounts (also referred to herein as doses) can be initially estimated based on results from in vitro assays and/or animal model studies. Such information can be used to more accurately determine useful doses in subjects of interest. Useful pre-clinical tests include pharmacodynamic analyses, toxicity analyses, and so forth.

Therapeutically effective amounts can be achieved by administering single or multiple doses during the course of a treatment regimen (e.g., hourly, every 2 hours, every 3 hours, every 4 hours, every 6 hours, every 9 hours, every 12 hours, every 18 hours, daily, every other day, every 3 days, every 4 days, every 5 days, every 6 days, weekly, every 2 weeks, every 3 weeks, or monthly).

The effective amounts of compounds containing active agents include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve local (e.g., intratumoral) or circulating levels that have been found to be effective in animals.

Compositions can be administered with one or more anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

In particular embodiments that include treating or preventing a cancer (including for instance a cancer metastasis), the compositions disclosed herein can be used in conjunction with other cancer treatments, such as chemotherapy, targeted therapy, radiation therapy, and/or immunotherapy. The compositions described herein can be administered simultaneously with or sequentially with another treatment within a selected time window, such as within 10 minutes, 1 hour, 3 hour, 10 hour, 15 hour, 24 hour, or 48 hour time windows or when the complementary treatment is within a clinically-relevant therapeutic window.

Pharmaceutical compositions can be for administration by parenteral (intramuscular, intraperitoneal, intravenous (IV) or subcutaneous injection), by instillation, or in a depo, formulated in dosage forms appropriate for each route of administration.

In some embodiments, the compositions are administered systemically, for example, by intravenous or intraperitoneal administration, in an amount effective for delivery of the compositions to targeted cells. Other routes include instillation or mucosal.

In certain embodiments, the compositions are administered locally, for example, by injection directly into a site to be treated. In some embodiments, the compositions are injected or otherwise administered directly to one or more tumors or diseased tissues. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps or incorporating the compositions into polymeric implants which can effect a sustained release of the compositions to the immediate area of the implant.

By way of example, in certain embodiments the therapeutic constructs are given locally, for instance to readily accessible tumors such as melanoma, head and neck cancer, breast cancer, and lymphoma; or systemically for other cancers such as lung cancer, liver cancer, pancreatic cancer, prostate cancer, and metastatic cancers.

Thus, the therapeutic compositions described herein can be administered (on their own or as part of a combination therapy) by a variety of routes, including any convenient way for use in human or veterinary medicine. A therapeutically effective amount of the desired active agent(s) can be formulated in a pharmaceutical composition to be introduced parenterally, transmucosally (e.g., orally, nasally, or rectally), or transdermally. In some embodiments, administration is parenteral, for instance, via intravenous injection, or intra-arteriole, intramuscular, intradermal, subcutaneous, intraperitoneal, intraventricular, and intracranial administration. The administered may be as a bolus or by continuous infusion over a period of time, by intramuscular, intraperitoneal, intracerobrospinal, subcutaneous, intra-articular, intrasynovial, intrathecal, oral, topical, or inhalation routes. In certain embodiments, for instance those involved in treatment of inflammatory conditions that impact joints, the pharmaceutical composition may be administered directly to the synovium, synovial fluid or joint capsule by injection preferably with a syringe. Administration may be local or systemic; the choice may be influenced by the condition being treated, as well as the active agent(s) and compositions being administered.

For injection, compositions can be made as aqueous solutions, such as in buffers such as Hanks' solution, Ringers solution, or physiological saline. The solutions can contain formulatory agents such as suspending, stabilizing and/or dispersing agents. Alternatively, the composition can be in lyophilized and/or powder form for constitution with a suitable vehicle, e.g., sterile pyrogen-free water, before use.

Compositions including a therapeutic construct may be administered in an aqueous solution, by parenteral injection. The injectable formulation can be in the form of a suspension or emulsion, and optionally includes pharmaceutically acceptable diluents, preservatives, solubilizers, emulsifiers, adjuvants and/or carriers. Such injectable compositions can include diluents such as sterile water, buffered saline of various buffer content (e.g., Tris-HCl, acetate, phosphate), pH and ionic strength; and optionally, additives such as detergents and solubilizing agents (e.g., TWEEN™ 20, TWEEN™ 80 also referred to as polysorbate 20 or 80), anti-oxidants (e.g., ascorbic acid, sodium metabisulfite), and preservatives (e.g., Thimerosal, benzyl alcohol). Examples of non-aqueous solvents or vehicles are propylene glycol, polyethylene glycol, vegetable oils, such as olive oil and corn oil, gelatin, and injectable organic esters such as ethyl oleate. The formulations for injection may be lyophilized and resuspended, for instance immediately before use. The injectable formulation may be sterilized by, for example, filtration through a bacterial retaining filter, by incorporating sterilizing agents into the compositions, by irradiating the compositions, or by heating the compositions.

In other embodiments, therapeutic construct-including compositions are applied topically or by instillation. Topical administration can include application to the lungs, nasal, oral (sublingual, buccal), vaginal, or rectal mucosa. These methods of administration can be made effective by formulating the shell or coating of the delivery vehicle with mucosal transport element(s). Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers. Chemical enhancers and physical methods including electroporation and microneedles can work in conjunction with this method.

A microneedle (MN) is a micron-sized needle with a height of 10-2000 µm and a width of 10-50 µm, which can penetrate through the epidermis layer to dermal tissue directly with minimal or no pain (Hao et al., *J Biomed Nanotechnol*, 13(12):1581-1597, 2017). Several types of microneedles can be used. In some embodiments, metal-based or plastic microneedle rollers can be used to physically disrupt skin surface to enhance penetration of the applied topical agents (therapeutic construct in this case). In some embodiments, degradable and dissolvable microneedles can contain therapeutic constructs. Upon administration to skin, microneedles can dissolve and release the construct deep in layers of skin. In some embodiments, non-degradable microneedles may be coated with therapeutic constructs, such that they deliver the coated construct deep in skin layers. Microneedles can be fabricated from many classes of materials, including but not limited to, polymer, saccharides, polysaccharides, peptide, protein, metals, inorganic compound, and so forth (Ye et al., *Adv Drug Deliv Rev*, 127: 106-118, 2018). All materials and fabrication methods known in the art for microneedle technology is applicable to enhance delivery of this therapeutic construct.

Any device that facilitates systemic or localized delivery of therapeutics is also applicable to the herein provided therapeutic constructs. For example, hepatic arterial infusion (HAI) pump, which is an implanted chemotherapy device that delivers high concentrations of cytotoxic agents directly to liver metastases with minimal systemic toxicities (Cohen et al., *The Oncologist*, 8(6): 553-566, 2003), can also be utilized to deliver the herein described therapeutic constructs. In some embodiments, convection enhanced delivery (CED), which involves the placement of a small diameter infusion catheter to deliver therapeutics to brain tumors (Mehta, A. et al. *Neurotherapeutics: the journal of the American Society for Experimental Neuro Therapeutics*, 14(2), 358-371, 2017), can also be utilized to deliver the herein described therapeutic constructs.

(VIII) EXEMPLARY METHODS OF USE

With the provision herein of therapeutic constructs that include at least one mitotic kinase inhibitor and at least one immune checkpoint inhibitor, there are now enabled methods of treating and/or preventing hyperproliferative diseases, disorders, or conditions, including cancer, symptoms of cancer, cancer progression (including from precancer to cancer), and cancer metastasis. Specific examples of hyperproliferative diseases, disorders, or conditions include cancer. In some embodiments, the cancer may suppress the immune system of the subject or individual with the cancer. In some embodiments, the therapeutic constructs as provided herein can suppress or reverse cancer-mediated immune suppression and allow for immune recognition and clearance of the malignancy.

As used herein, the term "treatment" or "treating" refers to any improvement of the cancer that occurs in a treated subject compared to an untreated subject. Such an improvement can be a prevention of a worsening or progression of the cancer (e.g., improved progression-free survival). Moreover, such an improvement may also be a reduction or cure of the cancer or its accompanying symptoms (e.g., reduction in tumor volume, partial remission, complete remission (e.g., for 6 months, 1 year, 2 years, 3 years, 4 years, or 5 years or more), prevention of cancer recurrence or relapse, reduction of metastasis, or reduction of number of tumors or lesions). It will be understood that a treatment may not be successful for 100% of the subjects to be treated. The term, however, requires that the treatment is successful as determined by people skilled in the art (e.g., oncologists, physicians). As used herein, the term "preventing" refers to avoiding the onset of cancer as used herein or its accompanying syndromes. It will be understood that prevention refers to avoiding the onset of cancer within a certain time window in the future. Said time window shall, preferably, start upon administration of a compound in the sense of the invention and lasts for at least 1 month, at least 6 months, at least 9 months, at least 1 year, at least 2 years, at least 5 years, at least 10 years or even for the remaining physiological life span of a subject. It will be understood that a prevention may not be successful for 100% of the subjects to be treated. The term, however, requires that the prevention is successful as determined by one skilled in the art (e.g., oncologists, physicians). Prevention may also be in the context of a recurrence of cancer after remission, e.g., as measured by a reduction in probability for recurrence in a population.

The disclosed compositions can be used to treat benign or malignant cancers, and tumors thereof. The treatment can directly target and kill cancer cells, indirectly target the cancer cells by increasing an immune response against the cancer cells; or a combination thereof.

In a mature animal, a balance usually is maintained between cell renewal and cell death in most organs and tissues. The various types of mature cells in the body have a given life span; as these cells die, new cells are generated by the proliferation and differentiation of various types of stem cells. Under normal circumstances, the production of new cells is so regulated that the numbers of any particular type of cell remain constant. Occasionally, though, cells arise that are no longer responsive to normal growth-control mechanisms. These cells give rise to clones of cells that can expand to a considerable size, producing a tumor or neoplasm. A tumor that is not capable of indefinite growth and does not invade the healthy surrounding tissue extensively is benign. A tumor that continues to grow and becomes progressively invasive is malignant. The term cancer refers specifically to a malignant tumor. In addition to uncontrolled growth, malignant tumors exhibit metastasis. In this process, small clusters of cancerous cells dislodge from a tumor, invade the blood or lymphatic vessels, and are carried to other tissues, where they continue to proliferate. In this way a primary tumor at one site can give rise to a secondary tumor at another site.

The disclosed compositions can delay or inhibit the growth of a tumor in a subject, reduce the growth or size of the tumor or eliminate it altogether, inhibit or reduce metastasis of the tumor, and/or inhibit or reduce symptoms associated with tumor development or growth. For example, in some embodiments, the compositions reduce tumor burden in the subject or slow or prevent tumor growth over time.

Malignant tumors may be classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The types of cancer that can be treated with the provided compositions and methods include, but are not limited to, vascular cancers such as multiple myeloma, as well as solid cancers, including adenocarcinomas and sarcomas, of bone, bladder, brain, breast, cervix, colon, rectum, esophagus, kidney, liver, lung, nasopharynx, pancreas, prostate, skin, stomach, and uterus. In some embodiments, the disclosed compositions are used to treat multiple cancer types concurrently. The compositions can also be used to treat metastases or tumors at multiple locations.

Administration is not limited to the treatment of an existing tumor but can also be used to prevent or lower the risk of developing such diseases in an individual, i.e., for prophylactic use and to reduce spread of cancer, for instance through metastasis. Potential candidates for prophylactic vaccination include individuals with a high risk of developing cancer, i.e., with a personal or familial history of certain types of cancer.

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, Herceptin® resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g. head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. The term "precancer", as used herein, refers to a condition or growth that precedes or develops into a cancer. The term "cancer metastasis", as used herein, refers to the spread of cancer cells or a tumor from one organ or part of the body to another organ or part of the body.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

(IX) KITS

Active component(s), including particularly at least one described therapeutic construct (including a delivery vehicle containing or associated with at least one mitotic kinase inhibitor and at least one immune checkpoint inhibitor), can be provided as kits. Kits can include one or more containers including (containing) one or more or more compounds or complexes (e.g., anti-cancer agents) as described herein, optionally along with one or more additional agents for use in therapy. For instance, some kits will include an amount of at least one additional anti-cancer composition, or an amount of at least one additional anti-inflammatory agent, or both.

Any active component in a kit may be provided in premeasured dosages, though this is not required; and it is anticipated that certain kits will include more than one dose.

Kits can also include a notice in the form prescribed by a governmental agency regulating the manufacture, use, or sale of pharmaceuticals or biological products, which notice reflects approval by the agency of manufacture, use, or sale for human administration. The notice may state that the provided active ingredients can be administered to a subject. The kits can include further instructions for using the kit, for example, instructions regarding administration; proper disposal of related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website. In particular embodiments, kits can also include some or all of the necessary medical supplies needed to use the kit effectively, such as applicators, ampules, sponges, sterile adhesive strips, CHLORAPREP®, gloves, and the like. Variations in contents of any of the kits described herein can be made. The instructions of the kit will direct use of the active ingredient(s) included in that kit to effectuate a clinical and/or therapeutic use described herein.

Suitable methods, materials, and examples used in the practice and/or testing of embodiments of the disclosed invention are described herein. Such methods and materials are illustrative only and are not intended to be limiting. Other methods, materials, and examples similar or equivalent to those described herein can be used.

The Exemplary Embodiments and Example(s) below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(X) EXEMPLARY EMBODIMENTS

1. A therapeutic construct including: a delivery system; at least one mitotic kinase inhibitor, e.g., coupled to or contained within the delivery system; and at least one immune checkpoint inhibitor, e.g., coupled to or contained within the delivery system.

2. The therapeutic construct of embodiment 1, wherein the delivery system includes a liposome, a lipid-based particle, a polymeric particle, an inorganic or organic nanoparticle or microparticle, or a hybrid thereof.

3. The therapeutic construct of embodiment 2, wherein the delivery vehicle includes one or more of fullerenes, endohedral metallofullerenes, trimetallic nitride templated endohedral metallofullerenes, single-walled and multi-walled carbon nanotubes, branched and dendritic carbon nanotubes, gold nanorods, silver nanorods, single-walled and multi-walled boron/nitrate nanotubes, carbon nanotube peapods, carbon nanohorns, carbon nanohorn peapods, liposomes, nanoshells, dendrimers, microparticles, quantum dots, superparamagnetic nanoparticles, calcium phosphate particles, aluminum salt particles, nanorods, cellulose nanoparticles, silicon, silica and polymer micro- and nano-spheres, silica-shells, biodegradable PLGA micro- and nano-spheres, gold nanoparticles, cerium oxide particles, zinc oxide particles, silver nanoparticles, carbon nanoparticles, iron nanoparticles, and/or modified micelles.

4. The therapeutic construct of any one of embodiments 1-3, wherein the delivery vehicle comprises a mesoporous silica nanoparticle.

5. The therapeutic construct of embodiment 4, wherein the mesoporous silica nanoparticle has a size of about 5-200 nm.

6. The therapeutic construct of embodiments 4 or 5, wherein the mesoporous silica nanoparticle is coated with cross-linked polyethyleneimine and polyethylene glycol.

7. The therapeutic construct of any one of embodiments 1-6, wherein the mitotic kinase inhibitor and/or immune checkpoint inhibitor includes an oligonucleotide, a polynucleotide, a small molecule inhibitor, or an antibody.

8. The therapeutic construct of any one of embodiments 1-7, wherein the at least one mitotic kinase inhibitor is an inhibitor of a polo-like kinase (PLK), an Aurora kinase, cyclin-dependent kinase (CDK)1, CDK2, HASPIN, monopolar spindle 1 kinase (Mps1), or a NimA-related kinase (NEK).

9. The therapeutic construct of any one of embodiments 1-8, wherein the mitotic kinase inhibitor includes one or more of GSK461364, BI2536, Tak960, NMS-P937, volasertib, Chk 1 Kinase Inhibitor LY2603618, AU14022, YK-4-279, AZ703, alisertib, prexasertib, or AZD7762.

10. The therapeutic construct of any one of embodiments 1-9, wherein the mitotic kinase inhibitor is volasertib.

11. The therapeutic construct of any one of embodiments 1-10, wherein the immune checkpoint inhibitor includes a siRNA, inhibitor, or antibody against one or more of PD-L1, PD-1, TIM-3, LAG-3, or CTLA-4.

12. The therapeutic construct of any one of embodiments 1-11, wherein the at least one immune checkpoint inhibitor selected from an antibody against PD-L1, PD-1, or CTLA-4.

13. The therapeutic construct of any one of embodiments 1-12, wherein the at least one immune checkpoint inhibitor is an antibody against PD-L1.

14. The therapeutic construct of embodiment 13, wherein the immune checkpoint inhibitor includes at least one of: nivolumab, pembrolizumab, MPDL3280A, ipilimumab, tremelimumab, atezolizumab, avelumab, durvalumab, cemiplimab, pidilizumab, or spartalizumab.

15. The therapeutic construct of any of the previous embodiments, further including an adjuvant.

16. The therapeutic construct of embodiment 15, wherein the adjuvant includes one or more of a CpG oligonucleotide, a DNA TLR agonist containing a CpG sequence, a non-CpG DNA TLR agonist, an RNA TLR agonist, an aluminum salt, an anti-CD40 antibody, a fusion protein, a cytokine, a small molecule TLR agonist, an oil- or surfactant-based adjuvant, a lipopolysaccharide, a plant extract, or a derivative thereof.

17. The therapeutic construct of embodiment 15 or 16, wherein the adjuvant includes a CpG oligonucleotide, imiquimod, resiquimod, gardiquimod, poly I:C, poly ICLC, dSLIM, or EnanDIM.

18. The therapeutic construct of embodiment 17, wherein the adjuvant comprises a CpG oligonucleotide.

19. The therapeutic construct of any one of embodiments 1-18, having a hydrodynamic size of 5-999 nm.

20. The therapeutic construct of any one of embodiments 1-18, having a hydrodynamic size of 1-1000 microns.

21. A therapeutic construct including: an immune checkpoint inhibitor; a mitotic kinase inhibitor; and a chemical linker linking the immune checkpoint inhibitor and the mitotic kinase inhibitor.

22. The therapeutic construct of embodiment 21, wherein the mitotic kinase inhibitor is an oligonucleotide, a polynucleotide, a small molecule inhibitor, or an antibody.

23. The therapeutic construct of embodiment 21 or 22, wherein the immune checkpoint inhibitor is an oligonucleotide, a polynucleotide, a small molecule inhibitor, or an antibody.

24. The therapeutic construct of any one of embodiments 21-23, wherein the immune checkpoint inhibitor is an antibody.

25. The therapeutic construct of any one of embodiments 21-24, wherein the immune checkpoint inhibitor is an antibody against PD-L1, PD-1, TIM-3, LAG-3, or CTLA-4.

26. The therapeutic construct of any one of embodiments 2125, wherein the immune checkpoint inhibitor is an antibody against PD-L1, PD-1, or CTLA-4.

27. The therapeutic construct of any one of embodiments 21-26, wherein the immune checkpoint inhibitor is an antibody against PD-L1.

28. The therapeutic construct of any one of embodiments 21-27, wherein the mitotic kinase inhibitor is selected from GSK461364, BI2536, Tak960, NMS-P937, volasertib, Chk 1 Kinase Inhibitor LY2603618, AU14022, YK-4-279, AZ703, alisertib, prexasertib, or AZD7762

29. The therapeutic construct of any one of embodiments 21-28, wherein the mitotic kinase inhibitor is alisertib.

30. The therapeutic construct of any one of embodiments 21-29, wherein the chemical linker comprises one or more of the a hydrazine; a disulfide; N-succinimidyl-4-(2-pyridyldithio)butanoate; N-succinimidyl-4-(2-pyridyldithio)-2-sulfo butanoate; perfluorophenyl 3-(pyridin-2-yldisulfanyl) propanoate; 2,5-dioxopyrrolidin-1-yl 3-methyl-3-(pyridin-2-yldisulfanyl)butanoate; Gly-Phe-Leu-Gly; Ala-Leu-Ala-Leu; Val-Cit; Phe-Lys; Val-Ala; Ala-Phe-Lys; Phe-Lys; (Gly)n, wherein n is 1-20; a β-glucuronide linker; maleimidocaproyl; N-(maleimidomethyl)cyclohexane-1-carboxylate; 4-(4-acetylphenoxy)butanoic acid; dibromomaleimide; para-aminobenzoic acid; 4-nitrophenol; acetic acid; formic acid; 4-maleimidobutyric acid N-succinimidyl ester; N-(4-maleimidobutyryloxy)succinimide; N-(6-maleimidocaproyloxy)succinimide; 3-maleimidopropionic acid N-succinimidyl ester; N-(3-maleimidopropionyloxy)succinimide; 5-maleimidovalericacid-NHS; linear, branched, or multiarm polyethylene glycol having a molecular weight of 100-10000 Da; propargyl-N-hydroxysuccinimidyl ester; pyrophosphate; succinimidyl-4-azidobutyrate; 4-azidobenzoic acid N-hydroxysuccinimide ester; ted-butyl 1-(4-formylphenyl)-1-oxo-5,8,11-trioxa-2-azatridecan-13-oate; or a residue thereof.

31. The therapeutic construct of any one of embodiments 21-30, wherein the chemical linker comprises N-(maleimidomethyl)cyclohexane-1-carboxylate linker or a residue thereof.

32. The therapeutic construct of any one of embodiments 21-31, wherein the chemical linker comprises sulfosuccinimidyl 4-(N-maleimidomethyl)cyclohexane-1-carboxylate.

33. The therapeutic construct of any one of embodiments 21-32, wherein the chemical linker comprises a linear polyethyleneglycol having a molecular weight of 100-10000 Da, or a residue thereof.

34. The therapeutic construct of any one of claims 21-33, wherein the ratio of mitotic kinase inhibitor to immune checkpoint inhibitor is about 1-20.

35. The therapeutic construct of embodiment 34, wherein the ratio of mitotic kinase inhibitor to immune checkpoint inhibitor is about 2-8.

36. The therapeutic construct of embodiment 34 or 35, wherein the ratio of mitotic kinase inhibitor to immune checkpoint inhibitor is about 4-6.

37. The therapeutic construct of any one of embodiments 21-33, wherein the ratio of immune checkpoint inhibitor to mitotic kinase inhibitor is about 1-20.

38. The therapeutic construct of embodiment 37, wherein the ratio of immune checkpoint inhibitor to mitotic kinase inhibitor is about 2-8.

39. The therapeutic construct of embodiment 37 or 38, wherein the ratio of immune checkpoint inhibitor to mitotic kinase inhibitor is about 4-6.

40. A composition comprising the therapeutic construct of any one of embodiments 1-39 and a pharmaceutically acceptable carrier, excipient, or diluent.

41. A method of treating cancer comprising administering to a subject with cancer an effective amount of the therapeutic construct of any one of embodiments 1-39, or the composition of embodiment 40.

42. The method of embodiment 41, wherein the subject is a human.

43. A method of treating a cell exhibiting symptoms of cancer comprising contacting the cell with a therapeutically effective amount of the therapeutic construct of any one of embodiments 1-39, or a composition of embodiment 40.

44. A method of treating a cell obtained from a subject exhibiting symptoms of cancer, comprising contacting the cell with a therapeutically effective amount of the therapeutic construct of any one of embodiments 1-39, or the composition of embodiment 40.

45. A method of treating a cell obtained from a subject exhibiting symptoms of cancer, comprising contacting cell ex vivo with a therapeutically effective amount of the therapeutic construct of any one of embodiments 1-39, or the composition of embodiment 40.

46. The method of embodiment 44 or 45, wherein the cell is a cancer cell.

47. The method of embodiment 44 or 45, wherein the cell is not a cancer cell.

48. The method of embodiment 47, wherein the cell is an immune cell.

49. The method of any one of embodiments 43-48, further comprising administering at least one treated cell back to a subject.

50. A method of treating a subject diagnosed as having a hyperproliferative disease or condition, comprising administering to the subject an effective amount of the composition of embodiment 40.

51. The method of embodiment 50, wherein the hyperproliferative disease comprises one or more of cancer, precancer, or cancer metastasis.

52. The method of embodiment 51 or 52, wherein the hyperproliferative disease comprises one or more of melanoma, lung cancer, breast cancer, pancreatic cancer, brain cancer, prostate cancer, head and neck cancer, kidney cancer, colorectal cancer, lymphoma, colon cancer, or liver cancer.

53. The method of any one of embodiments 50-52, wherein the administering comprises one or more of: injection to or at a tumor in the subject; infusion locally to or at a tumor in the subject; systemic injection in the subject; systemic infusion in the subject; inhalation by the subject; oral administration to the subject; or topical application to the subject.

54. The method of any one of embodiments 50-53, wherein the administering comprises microneedle application.

55. A method of enhancing an effect of an anti-cancer therapy in a subject in need thereof, comprising administering to a subject in need thereof an effective amount of the therapeutic construct of any one of embodiments 1-39 or the composition of embodiment 40, and at least one anti-cancer agent.

56. The method of embodiment 55, wherein the anti-cancer agent is a chemotherapeutic agent, a targeted therapeutic agent, or an immune checkpoint inhibitor.

57. The method of embodiment 55 or 56, wherein the therapeutic construct or composition and the anti-cancer agent are administered sequentially or concurrently.

58. A method of enhancing, increasing, or improving a radiation therapy effect in a subject diagnosed as having a neoplasia, comprising administering to a subject in need thereof an effective amount of the therapeutic construct of any one of embodiments 1-39 or the composition of claim 40, and at least one radiation therapy.

59. The method of embodiment 58, wherein the therapeutic construct or composition and the radiation therapy are administered sequentially or concurrently.

60. The method of any one of embodiments 49-59, wherein the subject is human.

61. A kit including the immunotherapeutic construct of any one of embodiments 1-39 and at least one anti-cancer agent.

62. The kit of embodiment 61, wherein the anti-cancer agent is a chemotherapeutic agent, a targeted therapeutic agent, or an immune checkpoint inhibitor.

(XI) EXAMPLES

Example 1: Combination of PLK1 Inhibition and PD-L1 Blockade for Treatment of Cancer Polo-like kinase 1 (PLK1) is a critical mitotic kinase that is overexpressed in various cancers and provokes oncogenic properties (Liu et al., *Translational Oncology*, 10(1): 22-32, 2017, e-pub 2016). Previous studies have illustrated the potential of PLK1 inhibition as a therapeutic strategy and several PLK1 small molecule inhibitors have reached clinical trials (Gutteridge et al., *Molecular Cancer Therapeutics*, 15(7): 1427-35, 2016). However, PLK1 inhibitors as a monotherapy have not advanced beyond clinical trials due to poor efficacy and dose-limiting toxicities (de Braud et al., *Annals of Oncology: Official Journal of ESMO*, 26(11): 2341-6, 2015; Schoffski et al., *European J Cancer*, 48(2): 179-86, 2012; Lin et al., *British J Cancer*, 110(10): 2434-40, 2014; Frost et al., *Current Oncology*, 19(1): e28-35, 2012). The most advanced PLK1 inhibitor, volasertib (B16727), reached phase Ill clinical trial for acute myeloid leukemia (blood cancer) (Gjertsen et al., *Leukemia*, 29(1): 11-9, 2015), but eventually failed to meet primary endpoint of objective response (Ingelheim, Results of Phase III study of volasertib for the treatment of acute myeloid leukemia presented at European Hematology Association Annual Meeting. Ridgefield, Conn., 2016). For lung cancer, volasertib was terminated as a monotherapy early in a phase 11 clinical trial due to lack of response at the given dose limiting toxicity (300 mg once every 3 weeks) (Ellis et al., *Clinical Lung Cancer*, 16(6): 457-65, 2015). These results suggest that alternative therapeutic strategies are needed to elicit the full potential of inhibiting PLK1.

The recent emergence of immune checkpoint blockade targeting the PD-L1/PD-1 axis have provided promising results for NSCLC patients. PD-L1 expression on tumor cells inhibits tumor directed cytotoxic CD8+ T cell activity by binding to PD-1 receptor of the T cells and suppressing their function (Ohaegbulam et al., *Trends in Molecular Medicine*, 21(1): 24-33, 2015; Shrimali et al., *Immunotherapy*, 7(7): 777-92, 2015; Zou et al., *Science Translational Medicine*, 8(328): 328rv4-rv4, 2016). Recently, checkpoint inhibitors for PD-1 and PD-L1 (e.g., pembrolizumab, nivolumab, atezolizumab, and durvalumab) received FDA approval for treatment of NSCLC, either as first line (pembrolizumab) or second line therapy (Gettinger, Immunotherapy of advanced non-small cell lung cancer with immune checkpoint inhibition. (Uptodate.com, 2018). However, while patients who respond may show robust and durable responses, only a minority of total patients respond, and many initial responders eventually relapse (Reck et al., *New England Journal of Medicine*, 375(19): 1823-33, 2016; Malhotra et al., *Translational Lung Cancer Research*, 6(2): 196-211, 2017; Moya-Horno et al., *Therapeutic Advances in*

*Medical Oncology*, 10: 1758834017745012, 2018). Furthermore, systemic distribution of antibodies against immune checkpoints can cause aberrant and uncontrolled immune responses, leading to immune-related adverse effects (irAEs) that damage normal tissues (Reynolds et al., *Journal of Clinical Oncology*, 36(15_suppl): 3096, 2018). These toxicities can result in discontinuation of treatment and in some instances irAEs can be fatal. Thus, strategies to improve the response and therapeutic efficacy of immune checkpoint blockade are of great interest (Kanwal et al., *Cureus*, 10(9): e3254-e, 2018).

Figure 2A:
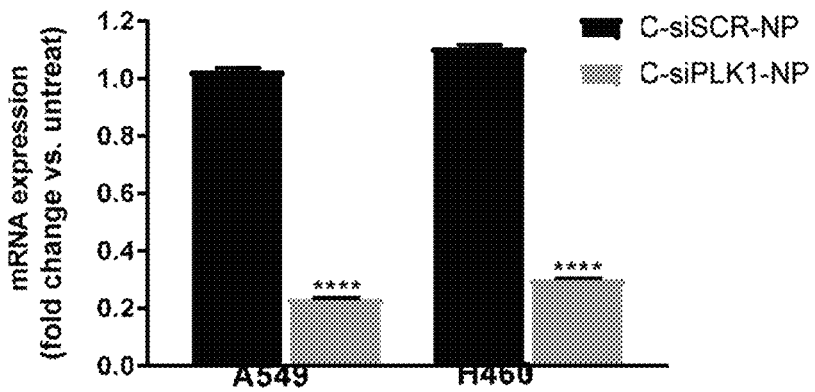
FIGS. 2A-2D. Effects of siRNA against mitotic regulator PLK1 (siPLK1) on non-small-cell lung carcinoma (NSCLC) cell lines (A549 and H460).
Figure 2B:
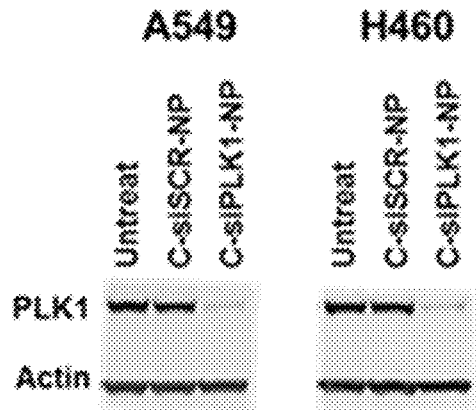
Figure 2C:
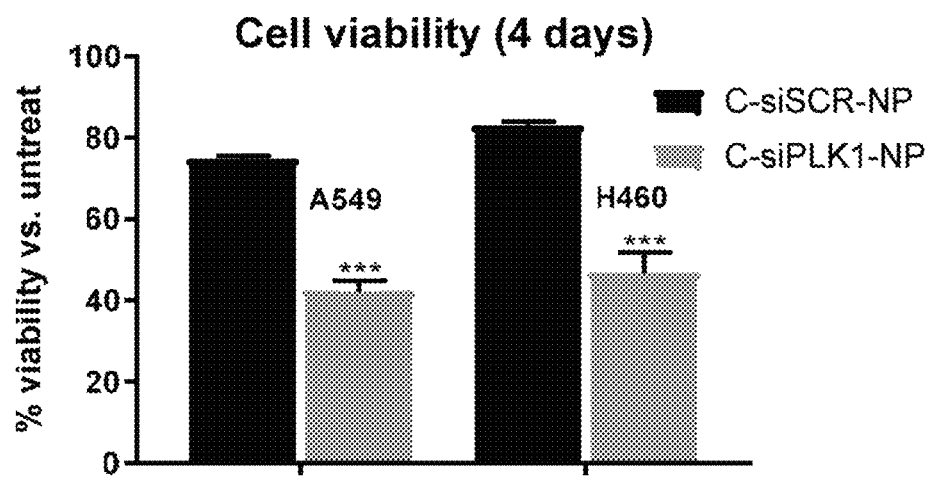

A recent study showed that PD-L1 protein abundance fluctuated during cell cycle progression in multiple human cancer cell lines, peaking in M and early G1 phase (Zhang et al., *Nature*, 553(7686): 91-5, 2018). Accordingly, increased PD-L1 protein abundance was observed in multiple mouse tumor-derived cell lines arrested in M phase by nocodazole or taxol (Zhang et al., *Nature*, 553(7686): 91-5, 2018). Reduction of PLK1 induced a strong mitotic arrest that can be sustained for several days post treatment (FIGS. 2A-2C, and Morry et al., *Mol Cancer Ther.* 2017, 16(4): 763-772). Collectively, these observations led us to hypothesize that combining PD-L1 antibodies with mitotic kinase inhibitors, such as PLK1 inhibitors, can increase cancer cell killing owing to the apoptotic effect of the PLK1 inhibitors and the anti-tumor immune effect that would be provoked by PD-L1 checkpoint blockade.

Herein, there is described development a PLK1 inhibitor loaded mesoporous silica nanoparticle platform (MSNP) conjugated to PD-L1 antibody to synergize combination effects of targeting both PLK1 and PD-L1. By utilizing the nanoparticle construct or antibody drug conjugate (ADC) to co-deliver these agents, we can effectively co-localize therapeutic effects to the tumor and reduce toxic concerns associated with systemic treatment of the drugs. The construct also triggers adaptive immunity against cancer. Our study highlights a rationale combination strategy to augment existing therapies without increasing toxicity by utilizing MSNP platform as a delivery carrier.

MATERIALS AND METHODS

Cell Lines and Reagents:

A549 NSCLC were purchased from ATCC (CCL-185) and maintained in RPMI media with 10% fetal bovine serum (FBS). Lewis Lung Carcinoma (LLC) metastatic variant, LLC-JSP cells, and fluorescent labeled LLC-JSP cells were gift from Dr. Don Gibbons lab (MD Anderson Cancer Center), and were cultured in RPMI+10% FBS. Antibodies used: Human PD-L1 antibody (eBioscience), mouse PD-L1 (PE, BD Biosciences), mouse CD3 (APC, eBioscience), mouse CD8a (Pacific Blue, Invitrogen), mouse CD4 (BV711, BD biosciences), mouse PD-1 (PE/Cy7, BioLegend). Alexa Fluor 488 secondary antibody was purchased from Life Technologies. In vivo grade mouse PD-L1 antibody was purchased from BioXcell (BE0101), and volasertib was purchased from Selleckchem. SiRNA sequences: PLK1 (antisense 5'-UAUUCAUUCUUCUUGAUCCGG-3'; SEQ ID NO: 2); scrambled SCR (antisense 5'-UUAGUCGACAUGUAAACCA-3' SEQ ID NO: 3) were purchased from Dharmacon.

Nanoparticle Synthesis and Characterization:

Bare MSNPs were synthesized as we have previously reported (Ngamcherdtrakul et al., *Advanced Functional Materials*, 25(18): 2646-59, 2015, and U.S. Patent Publication No. 2017/0173169). For PLK1 inhibitor loading, volasertib was dissolved in DMSO and diluted in ethanol solution and mixed with MSNPs in ethanol for overnight shaking at room temperature (350 RPM). The next day, nanoparticles were coated with PEI (Alfa Aesar) and mal-PEG-NHS (Jenkem) following our previous studies (Ngamcherdtrakul et al., *Advanced Functional Materials*, 25(18): 2646-59, 2015; Ngamcherdtrakul et al., *Int J Nanomedicine*, 13: 4015-27, 2018). For PD-L1 antibody conjugation, in vivo grade mouse PD-L1 antibody (BioXcell) was buffer exchanged to PBS pH 8 (Zeba spin column, Thermo Fisher) and thiolated using Traut's reagent (Thermo Fisher) following manufacturer's protocol. Thiolated antibody was added to NP at 20 wt. % and shaken overnight at 4° C. (300 RPM). Nanoparticles were washed with PBS pH 7.2 before characterization. Nanoparticle size was 90 nm, determined using Malvern Zetasizer. Antibody loading was 4 wt. %, determined by protein quantification of NP supernatant with BCA assay. To quantify PLK1 inhibitor loading, nanoparticles were shaken in DMSO solution to release the drug and supernatant was collected. Absorbance of supernatant was measured with Tecan plate reader to determine loading extent to be 0.5 wt. %. The p-iPLK1-NP is nanoparticle loaded with both PLK1 inhibitor and PD-L1 antibody, p-NP is nanoparticle loaded with PD-L1 antibody, and iPLK1-NP is nanoparticle loaded with PLK1 inhibitor.

Flow Cytometry:

Cells (100K cells/well) were plated in 6 well plates overnight and treated with indicated treatments the next day. Following treatments, cells were collected and aliquoted to 1 million cells per sample before washing in FACs buffer and staining. Primary and secondary antibodies were stained for 30 mins and 1 hour, respectively, under rocking on ice. After staining, cells were washed in FACs buffer before flow analysis with Guava easyCyte (Millipore Sigma) flow cytometer (10,000 events per sample). For tumors, tumors were harvested, minced, and incubated with 1 mg/ml DNAse for 30 minutes before smashing through 70 um filter to obtain single cell suspension. RBC lysis buffer was incubated with cells for 5 minutes, and washed with PBS. 1 million cells per sample were blocked with Fc-shield before staining with dye conjugated antibodies for 30 minutes (in FACs buffer). Cells were then washed with FACs buffer and analyzed with Guava (50,000 events per sample).

Western Blot.

Cells were seeded in 6 well plates overnight and treated with indicated treatments. Cell culture medium was changed one day after treatment. Three days post treatment, cells were lysed in RIPA buffer (50-100 μl per well). Lysate was sonicated and centrifuged (15,000 RPM for 15 minutes) and supernatant was collected. Amount of total protein was quantified using BCA. 30 μg of proteins (per sample) were mixed with 4× Novex NUPAGE® LDS sample buffer and beta-mercaptoethanol (10% final concentration). Samples were denatured for 5 min at 95° C. and loaded onto gel (NUPAGE®) for electrophoresis. Proteins were then transferred onto PVDF-FL membrane and blocked with LICOR blocking buffer. Membranes were incubated with primary antibodies overnight (PLK1, phospho-STAT3 (Tyr705), β-ACTIN) at 4° C. Next day, membranes were rinsed with TBS-T and IRDYE® conjugated secondary antibodies (LI-COR®) were added for 1 hour under rocking at room temperature. Membranes were scanned on a LI-COR® Odyssey® CLx imaging system.

Cell Viability after Treatments:

Cells (1500/well) were plated in white flat bottom 96 well plate overnight. The following day, cells were treated with indicated treatments and media was changed 24 hr post treatment. 3-5 day post treatment, cell viability was assessed using Cell Titer Glo assay (Promega) following manufacturer's instructions. Luminescence was read with Tecan plate reader.

RT-qPCR to assess PLK1 gene knock down:

RNA was isolated with GeneJet RNA purification kit (Thermo Fisher Scientific) following manufacturer's instructions. One-Step qRT-PCR was performed using EXPRESS One-Step Superscript™ qRT-PCR Kit (Invitrogen). Cycling conditions: 50° C. for 2 min, 95° C. for 10 min, 40 cycles of 95° C. for 15 s, and 60° C. for 1 min. TAQMAN gene expression primers Human HPRT mRNA (Hs99999909_m1), Human PLK1 mRNA (Hs00983225_g1), and Human PD-L1 (Hs00204257_m1) were used. Data was analyzed using $2^{-\Delta\Delta C(t)}$ Method.

Syngenic Tumor Models and Treatments:

For single tumor flank model, LLC-JSP murine lung cancer cells (200K) were inoculated in right flank of C57BL/6 female mice (6 weeks) (Charles River NCI colony). At 8 days post tumor inoculation, mice received intraperitoneal (i.p.) treatments of volasertib (20 mg/kg) and/or PD-L1 antibody (mouse PD-L1 from BioXcell); 10 mg/kg) every 5 days for 3 doses total. Tumors were measured with Vernier Caliper and volume calculated by $V=0.5 \times length \times width^2$. For bilateral tumors, C57BL/6 were inoculated with 100K and 40K LLC-JSP cells in right and left flank, respectively. At 12 days post inoculation, the aforementioned treatments were administered intratumorally to the right tumor every 3 days for 3 doses total. For both single flank and bilateral flank tumor models, mice were sacrificed when total tumor burden exceeded 2000 mm$^3$. For metastatic lung tumor model, LLC-JSP (200K) were injected intravenously (i.v.) to 6 week old C57BL/6 mice. At 3 days post cancer cell injection, mice were randomly grouped and treated with i.v. saline, p-iPLK1-NP (25 mg/kg NP), or i.p. PD-L1 antibody (5 mg/kg) and volasertib (1.25 mg/kg) every 3 days for a total of 4 doses. All studies were reviewed and approved by Institutional Animal Care and Use Committee (IACUC) at Oregon Health and Science University (OHSU).

Statistical Analysis:

GraphPad Prism 8.0 (GraphPad Software Inc.) was used for all statistical analysis. Comparison between two groups was performed with Student's t test. Tumor growth was analyzed using two-way repeated measures ANOVA with Tukey's correction for multiple comparisons. Kaplan Meier survival curve was analyzed using the log-rank (Mantel-Cox) method. Significance was set at p<0.05. In vitro data are expressed as mean±SD; in vivo data are expressed as mean±SEM.

RESULTS

Figure 2D:
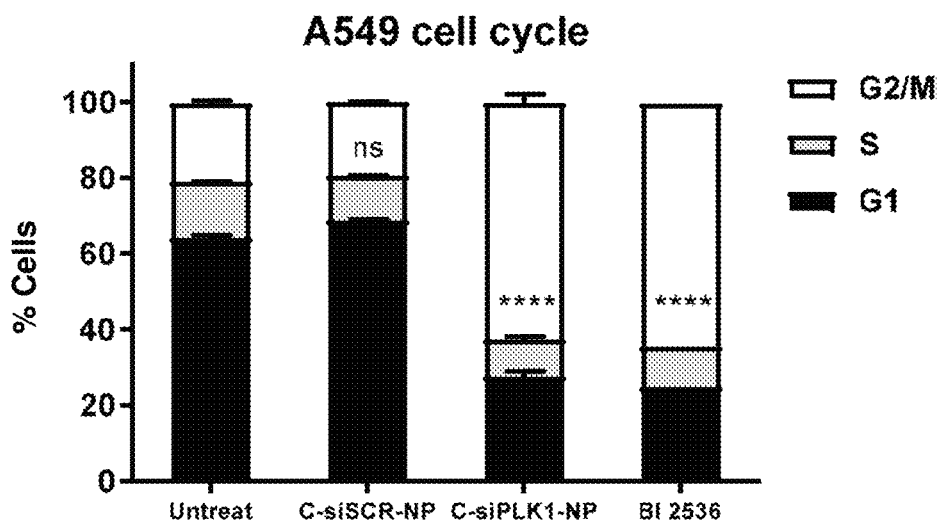

PLK1 Knock-Down Induces Expression of PD-L1 in Cancer Cells:

Mitotic kinase inhibitors such as small molecule inhibitor (e.g., B12536) or siRNA against PLK1 delivered on a nanoparticle (see Patent Publication No. 2017/0173169) which knocked down PLK1 (FIGS. 2A-2B), leading to lung cancer cell death (FIG. 2C), and putting the cancer cells in G2/M growth arrest (FIG. 2D). This agrees with a previous report that PLK1 inhibition or knock-down results in cell cycle arrest in G2/M in breast cancer (Morry et al., *Mol Cancer Ther.*, 16(4):763-772, 2017).

Figure 3A:
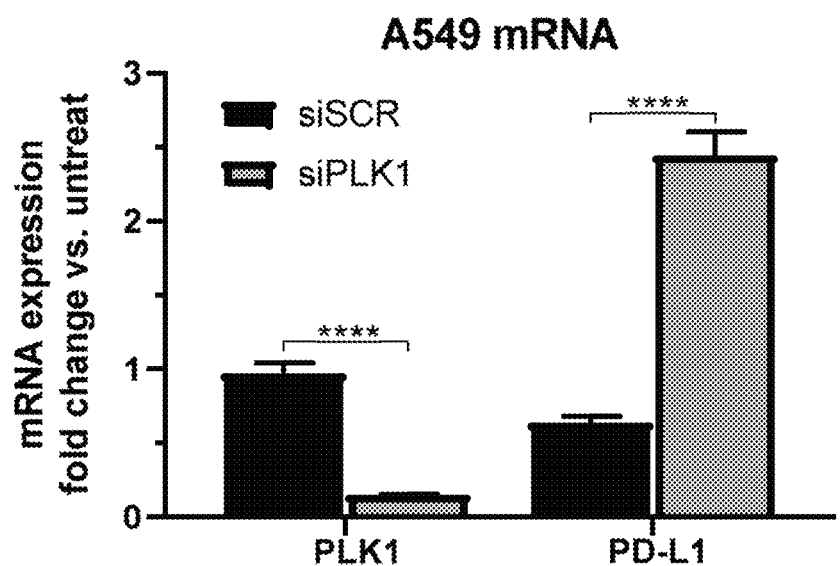
FIGS. 3A-3C. PLK1 knock-down by siRNA induces PD-L1 expression.
Figure 3B:
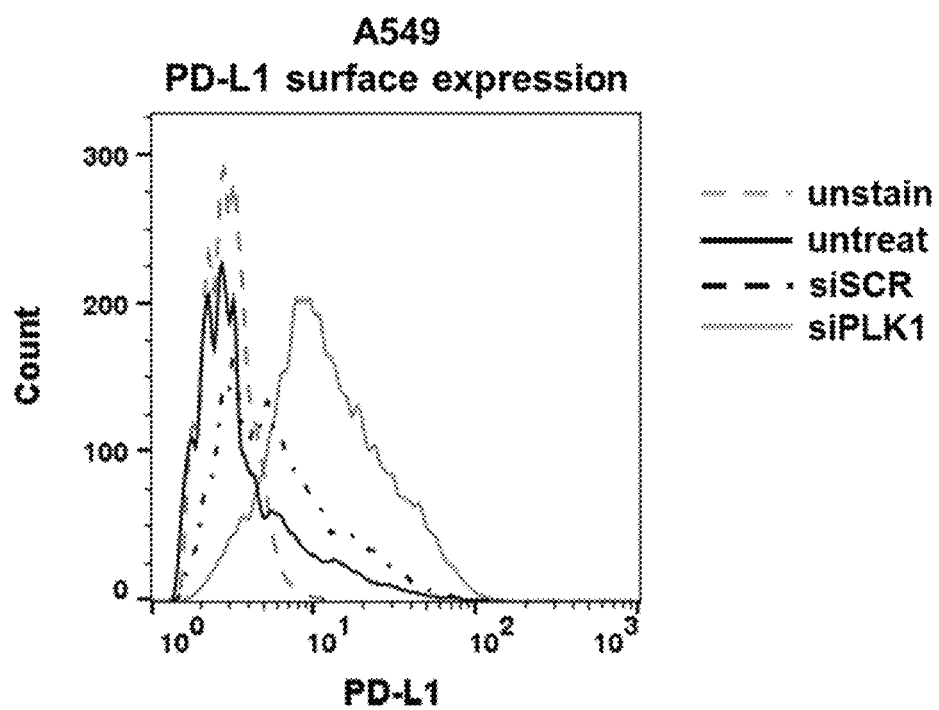
Figure 3C:
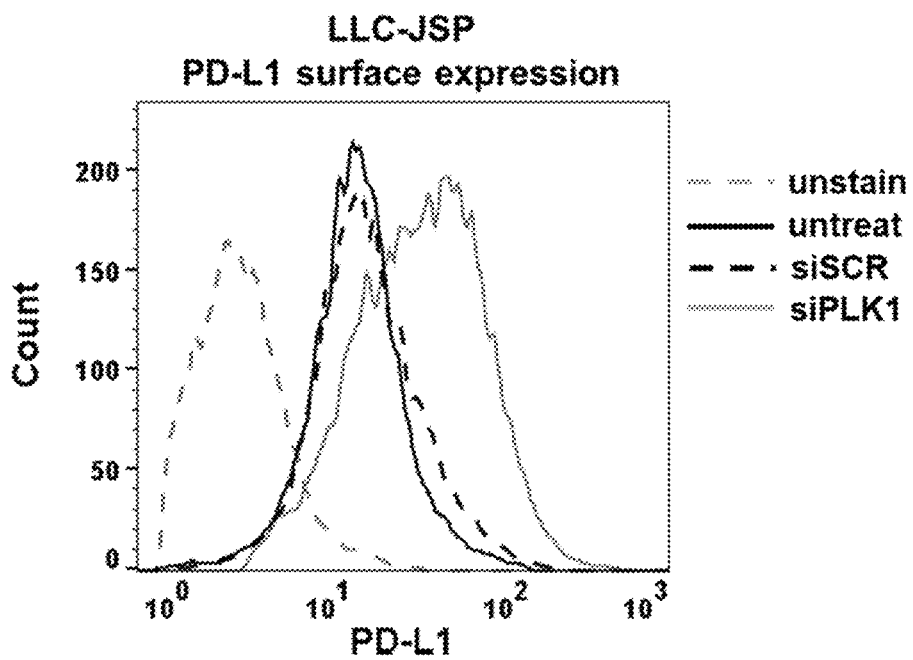

The PLK1 knockdown resulted in an increase in PD-L1 surface expression in both human (A549, FIGS. 3A-3B) and murine (LLC-JSP, FIG. 3C) lung cancer cell lines. As shown in FIG. 3A, 85% knockdown of PLK1 mRNA (by siRNA against PLK1) resulted in 2.5-fold increase in PD-L1 mRNA expression in A549 cell line compared with control treated cells. This was then confirmed at the surface protein level in A549 (FIG. 3B) and LLC-JSP (FIG. 3C) lung cancer cell lines at 3 days post siRNA treatments.

Mitotic Kinase Inhibitors Kill Cancer Cells and Upregulate PD-L1 Expression.

Figure 4A:
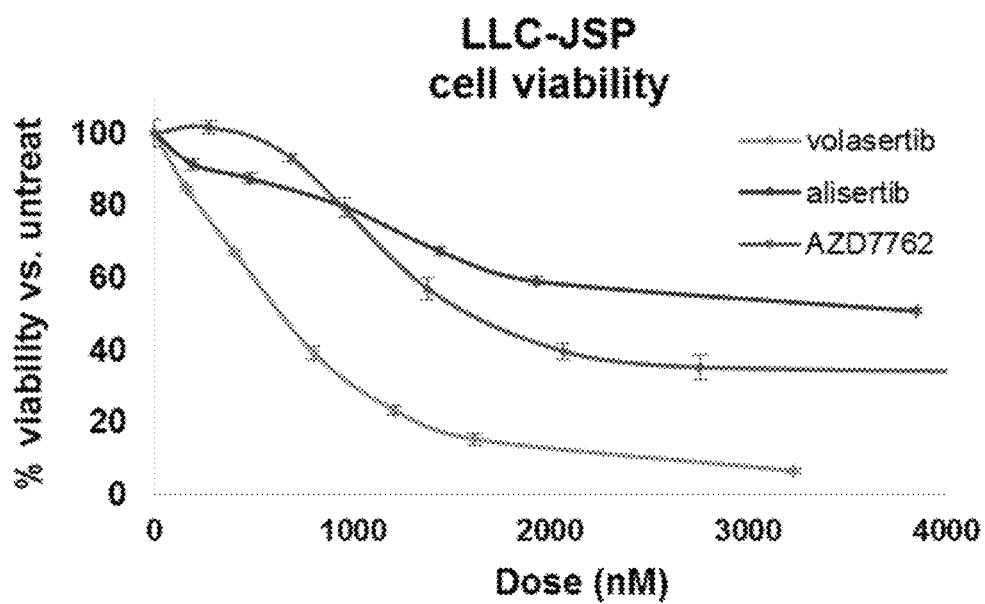
FIGS. 4A-4C Treatment effects of mitotic kinase inhibitors on (A) 3-day viability of LLC-JSP cells, (B) PD-L1 expression levels of surviving cells post treatment with 500 ng/ml of volasertib, alisertib, or AZD7762 as determined by flow cytometry and (C) their quantification.
Figure 4B:
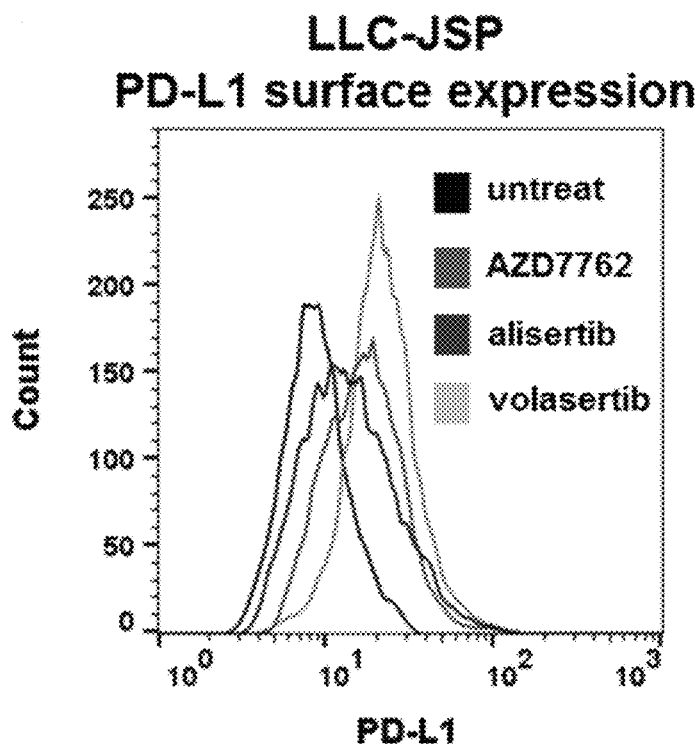
Figure 4C:
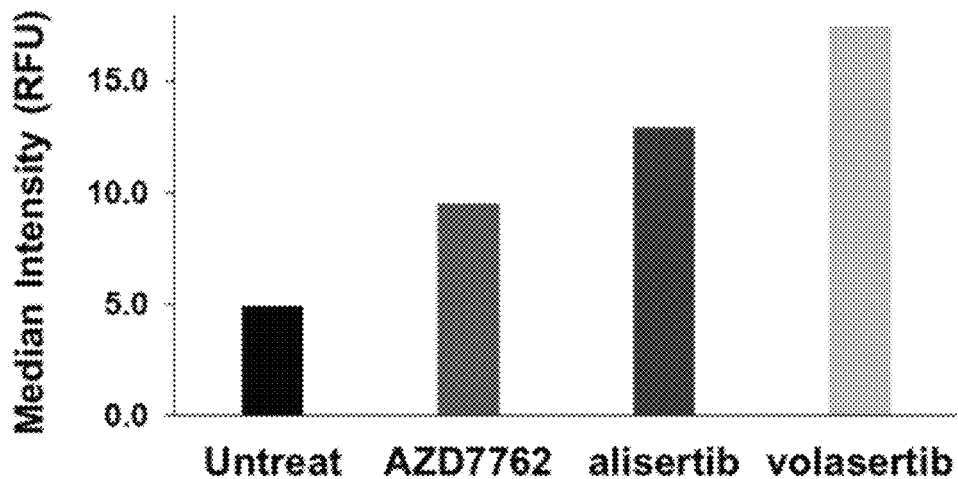

Following on our discovery that PLK1 knockdown results in PD-L1 upregulation, we sought to determine whether this holds true for inhibition of mitotic kinases in general. Three leading mitotic kinase inhibitors screened against PLK1 (volasertib), Aurora kinase A (alisertib), and CHK1 (AZD7762) in mouse lung cancer cell lines. As shown in FIG. 4, treatment of LLC-JSP (a murine lung cancer cell line) with volasertib, alisertib, or AZD7762 led to significant cell death (FIG. 4A) and upregulated surface PD-L1 level (FIGS. 4B-4C) in each case. This confirmed the link between mitotic kinase inhibition (regardless of the kinase classes) and PD-L1 upregulation. The surviving cells have increased levels of immune checkpoint molecules (e.g., PD-L1, FIGS. 3A-3C and FIGS. 4B-4C), which prevents cytotoxic T cells from attacking the surviving cancer cells. Thus, co-delivery of a mitotic inhibitor (e.g., PLKs, Aurora kinases, CHK1, CDK1/2, HASPIN, Mps1, NEK inhibitors) and immune checkpoint inhibitor (e.g., monoclonal antibody against PD-L1, PD-1, CTLA-4) on the same construct will yield greater cancer death.

Figure 5A:
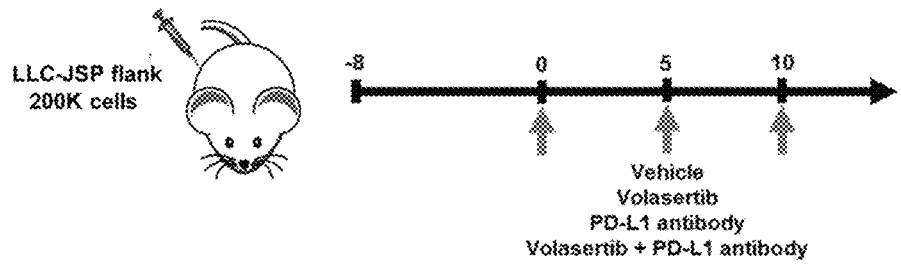
FIGS. 5A-5C. Enhanced cancer treatment with PD-L1 inhibitor and PLK1 inhibitor given as free drugs.
Figure 5B:
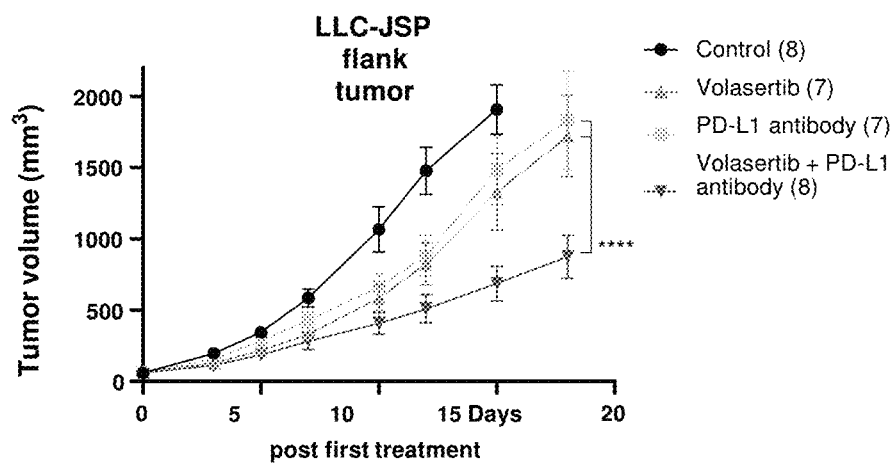
Figure 5C:
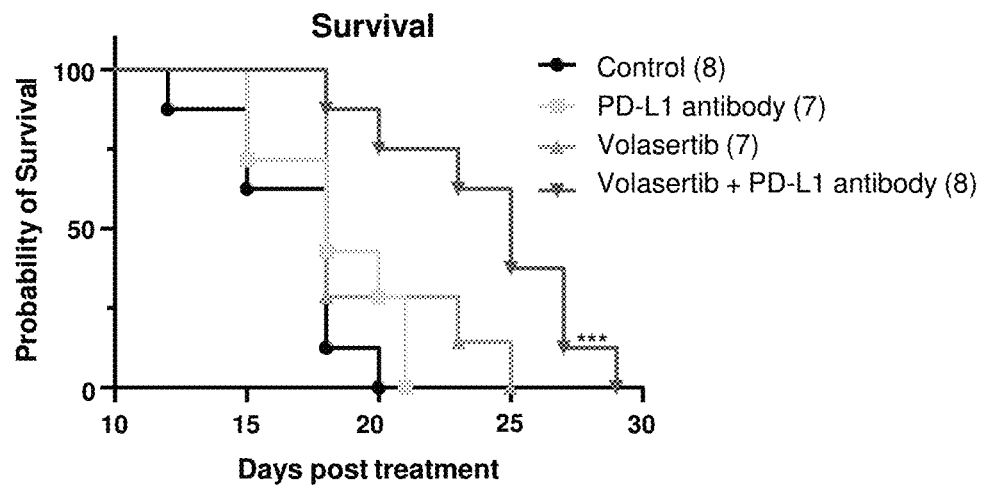

Combination of PLK1 Inhibition with PD-L1 Blockade Enhances Tumor Control In Vivo:

Based on our finding that PLK1 reduction results in PD-L1 increase, we sought to investigate whether PLK1 inhibition and PD-L1 blockade would synergize in vivo. We used LLC-JSP cell line to develop flank tumor model in immune-competent mice (Chen et al., *Nature Communications*, 5: 5241, 2014). Established tumors (>60 mm$^3$) at day 8 post tumor inoculation were treated i.p. with the PLK1 inhibitor volasertib (20 mg/kg) and PD-L1 monoclonal antibody (10 mg/kg) every 5 days for a total of 3 doses (FIG. 5A). As shown in FIG. 5B, the combination treatment significantly reduced tumor growth compared with single drug administrations. Moreover, the combination significantly prolonged survival of mice (FIG. 5C), confirming our hypothesis.

Figure 6A:
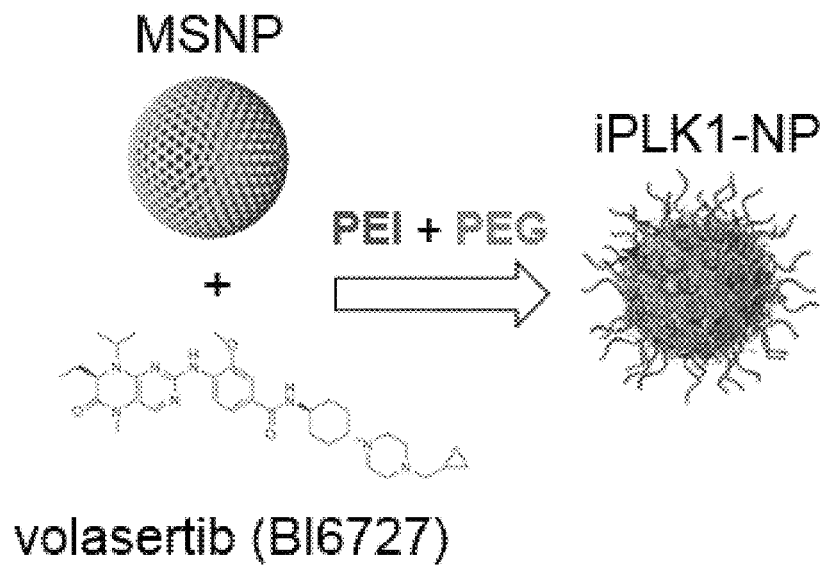
FIGS. 6A-6D Nanoparticle delivery of PLK1 inhibitor volasertib (iPLK1-NP) to mouse NSCLC cells.
Figure 6B:
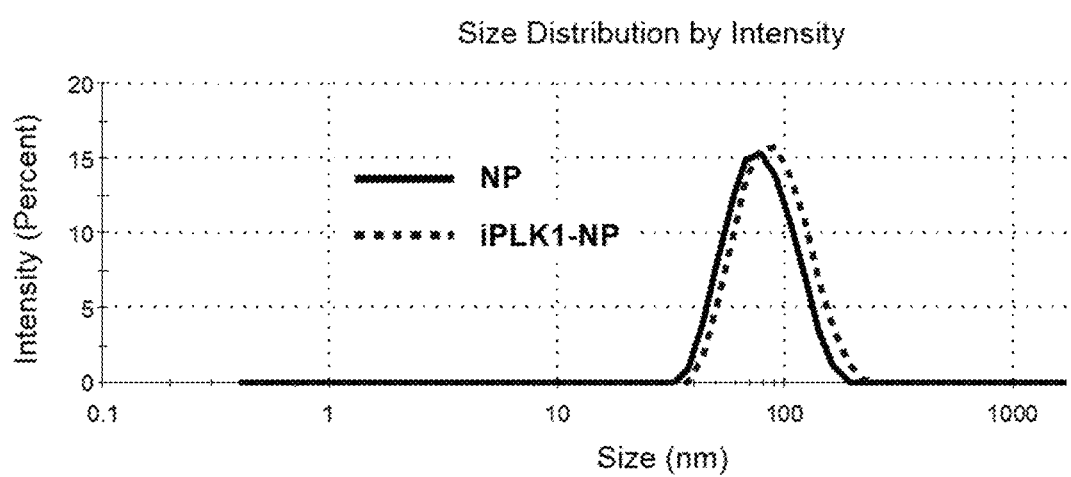
Figure 6C:
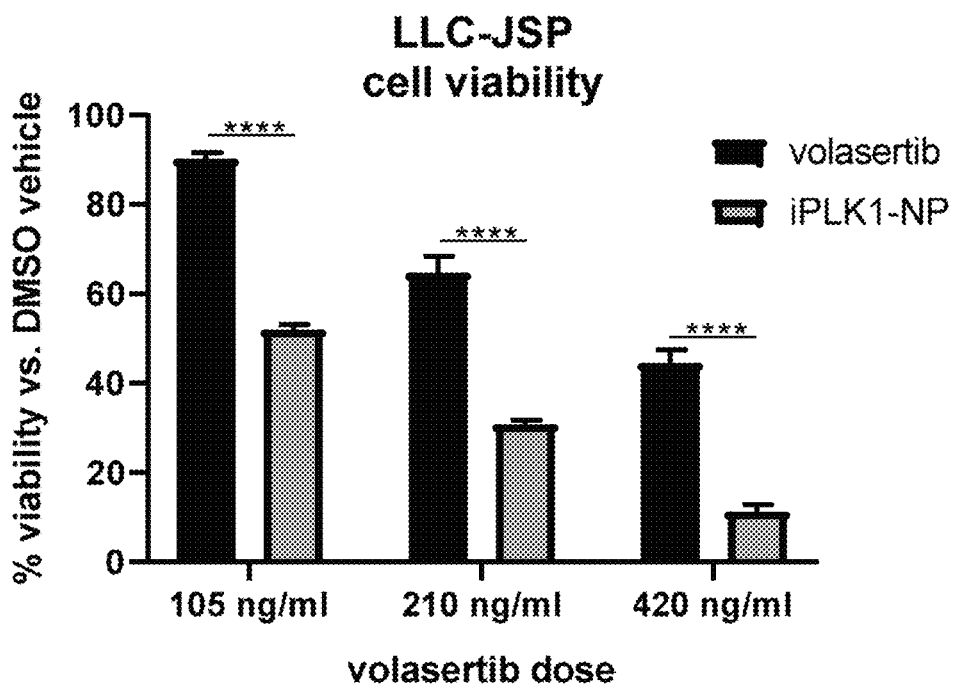
Figure 6D:
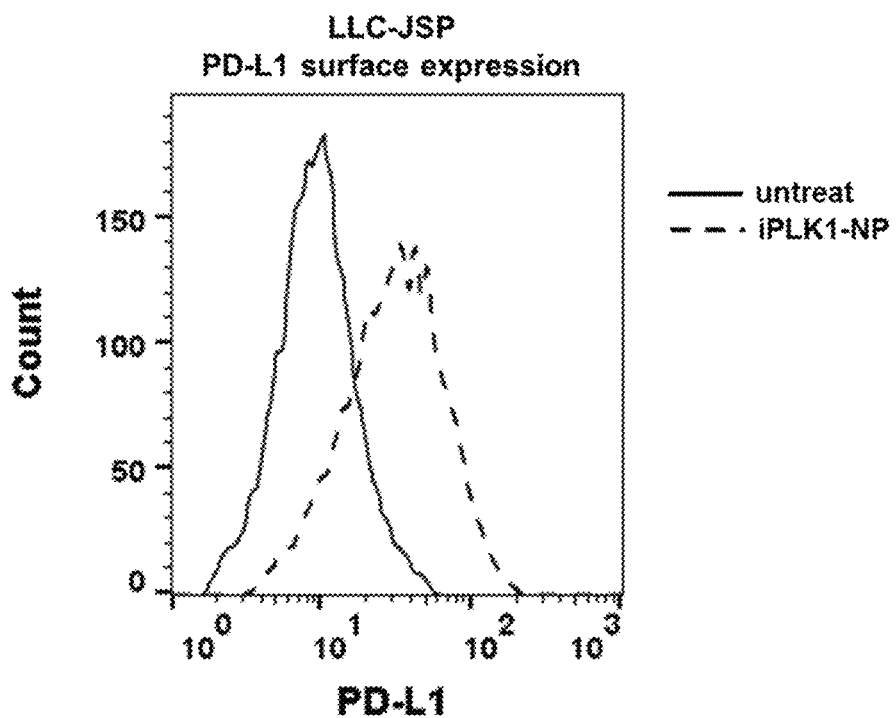

Nanoparticle Delivery of PLK1 Inhibitor Volasertib (iPLK1-NP):

Despite the promise of mitotic kinase PLK1 as a therapeutic target, clinical trials with current small molecule inhibitors have been disappointing. All six of PLK1 inhibitors (GSK461364, B12536, Tak960, NMS-P937, TKM-PLK1, and B16727) have failed in clinical trials. To reduce toxicity and improve tumor bioavailability of PLK1 inhibitor, we investigated whether our MSNP platform could improve the efficacy of a clinically available PLK1 inhibitor. Morry et al. (*Mol Cancer Ther,* 16(4):763-772, 2017) demonstrated the promise of this MSNP platform to target and deliver siRNA to breast tumors including those metastasized to lungs and orthotopic lung tumors. In this research, we utilized the platform to deliver the small molecule inhibitor volasertib, which is the most advanced inhibitor of PLK1. Volasertib was loaded onto mesoporous silica (FIG. 6A) prior to surface modification with polyethylene imine (PEI) and polyethylene glycol (PEG). The final nanoparticle (referred to as iPLK1-NP) size is 90 nm (FIG. 6B) which is in the appropriate range to take advantage of the EPR effect, and contains 0.5 wt. % PLK1 inhibitor volasertib. As shown in FIG. 6C, treatment of LLC-JSP cells with volasertib or iPLK1-NP significantly reduced cell viability compared with vehicle treated cells in a dose-dependent manner. Further, treatment with iPLK1-NP reduced cell viability more than the free PLK1 inhibitor (FIG. 6C). In agreement with previous finding using PLK1 siRNA (FIGS. 3A-3C) and mitotic kinase inhibitors (FIGS. 4B-4C), treatment with iPLK1-NP resulted in significant increase in PD-L1 cell surface expression (FIG. 6D).

Figure 7A:
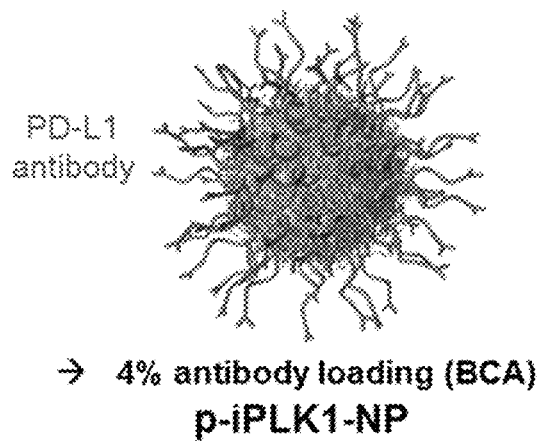
FIGS. 7A-7E. Nanoparticle for co-delivery of PLK1 inhibitor (iPLK1) and PD-L1 antibody (p-iPLK1-NP).
Figure 7B:
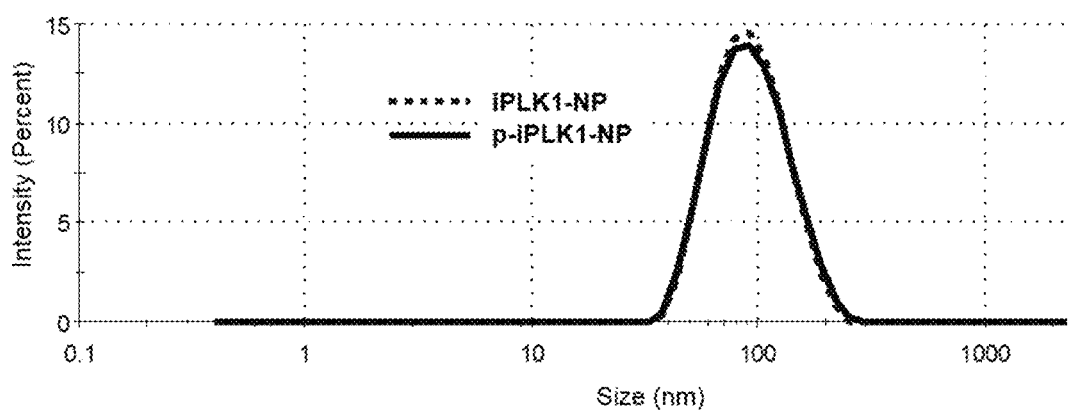
Figure 7C:
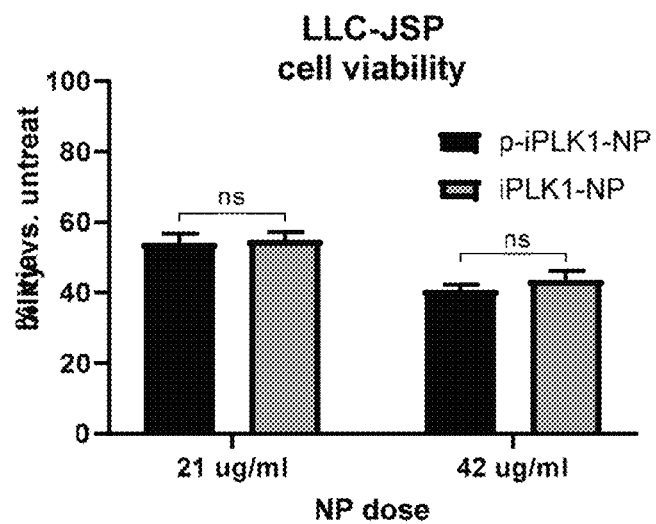
Figure 7D:
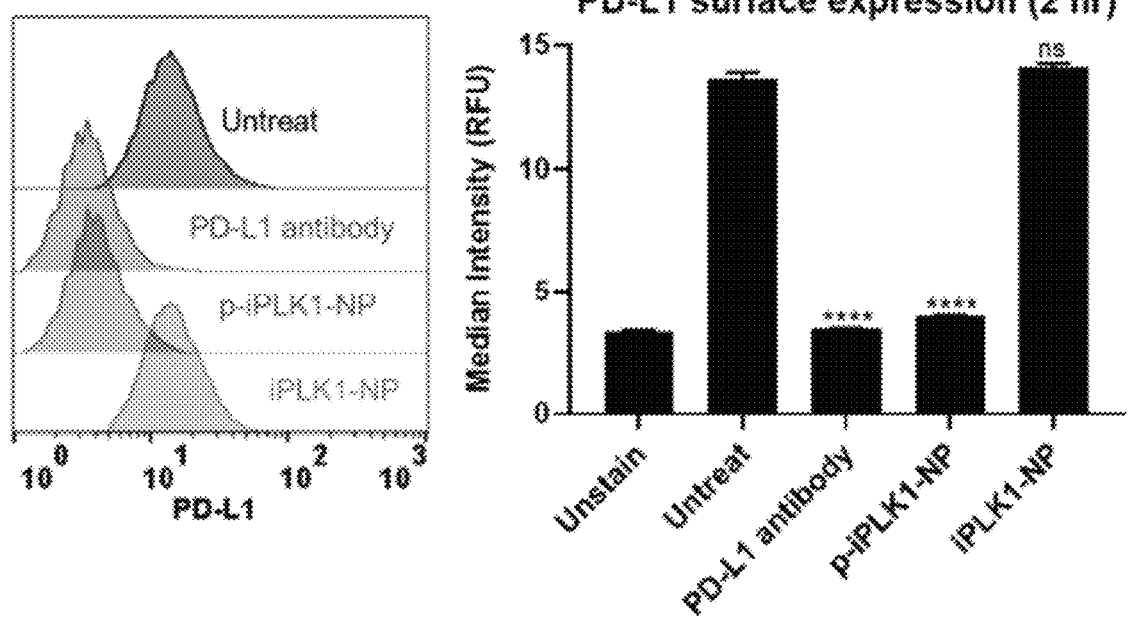
Figure 7E:
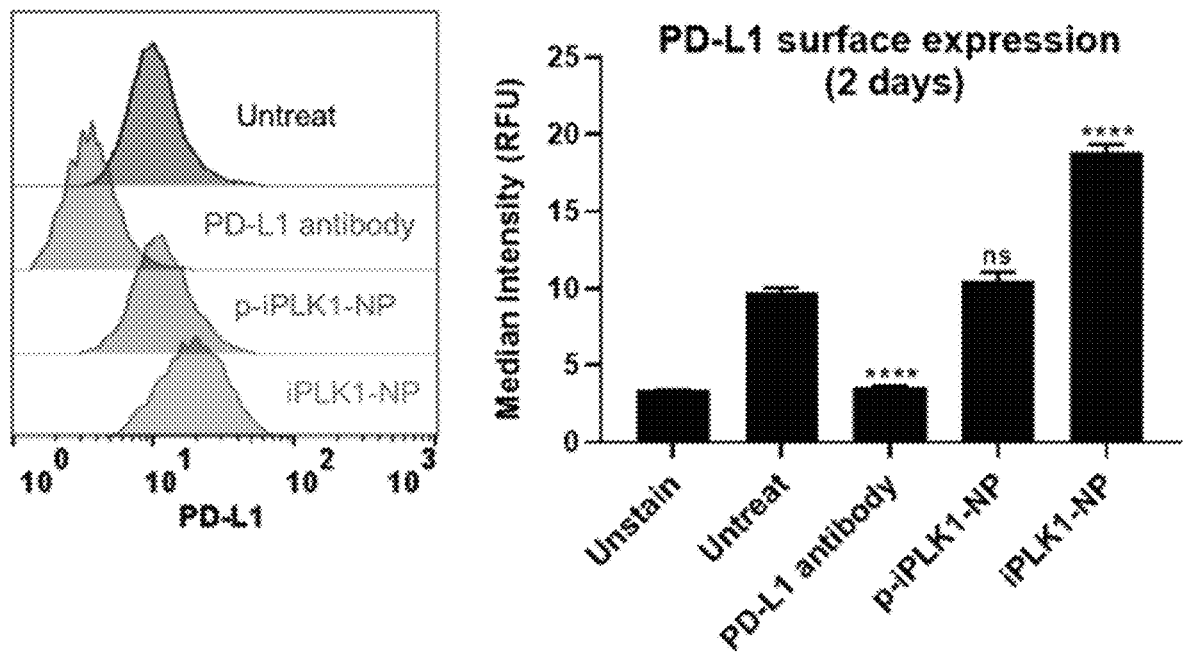

Nanoparticle for Co-Delivery of iPLK1 and PD-L1 Antibody (p-iPLK1-NP):

As iPLK1-NP could effectively kill cancer cells and simultaneously upregulate PD-L1 of the surviving cells, we aimed to utilize this as an advantage to target PD-L1+ cancer cells by conjugating PD-L1 antibody on iPLK1-NP. In this sense, a feed-forward loop can be generated where repeated administrations of PD-L1 targeted iPLK1-NP (referred to as p-iPLK1-NP) would upregulate PD-L1 expression and allow for superior tumor targeting to induce both apoptosis (via PLK1 inhibition) and anti-tumor immune responses (via PD-L1 blockade). This would be particularly advantageous for treating tumors without obvious targets/receptors for nanoparticle delivery, and may ultimately allow for higher response rates of immune checkpoint blockade. As illustrated in FIG. 7A, PD-L1 antibody was conjugated to PEG on NPs, and antibody amount was determined by BCA assay to be 4 wt. %. The hydrodynamic size of the construct is shown in FIG. 7B to be about 90 nm. As with iPLK1-NP, treatment with p-iPLK1-NP significantly reduced cell viability in LLC-JSP cell line (FIG. 7C). Furthermore, LLC-JSP cells incubated for 2 hours with p-iPLK1-NP blocked PD-L1 surface receptors as much as free PD-L1 antibody delivered at 25-fold higher dose (FIG. 7D). This is likely due to the high local concentration of antibody the cell experienced when antibody was delivered with nanoparticles. The iPLK1-NP had no effect on PD-L1 level at this short time point (FIG. 7D). Treatment of cells for 2 days with iPLK1-NP increased PD-L1 level as anticipated, which was reduced to normal level (see untreat) upon treatment with nanoparticle containing PD-L1 antibody (p-iPLK1-NP) (FIG. 7E). This demonstrates the nanoparticle targeting and blockade of PD-L1 receptors, which are induced by PLK1 inhibition.

Figure 8A:
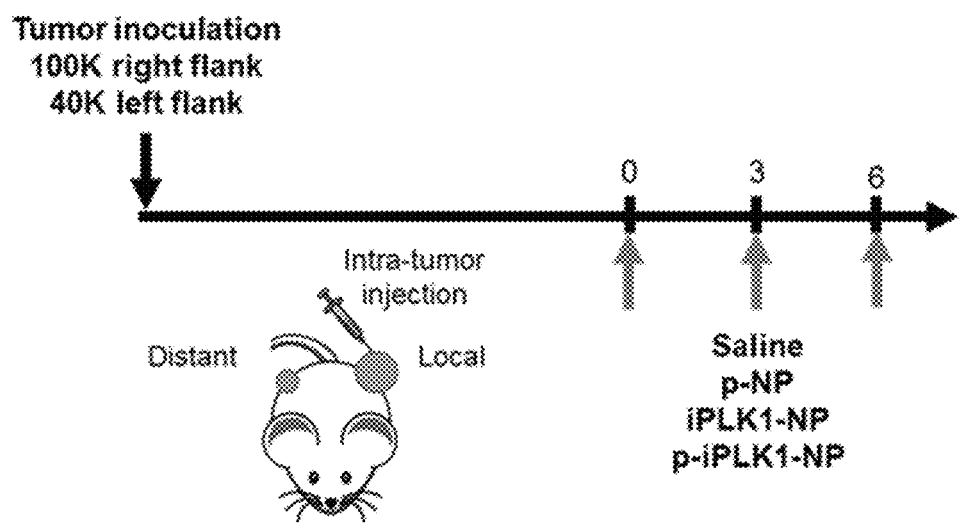
FIGS. 8A-8E. p-iPLK1-NP elicits anti-tumor immune effects.
Figure 8B:
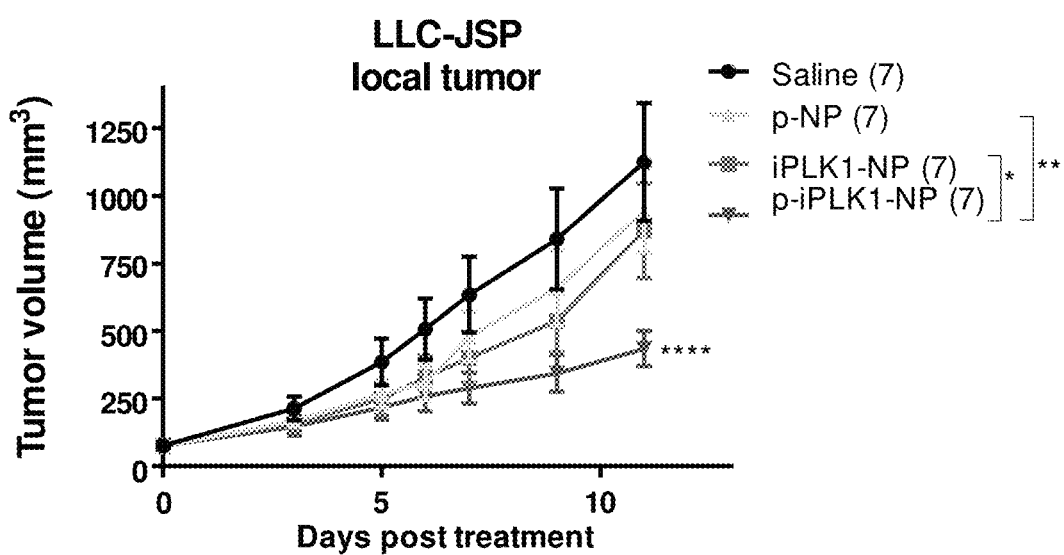
Figure 8C:
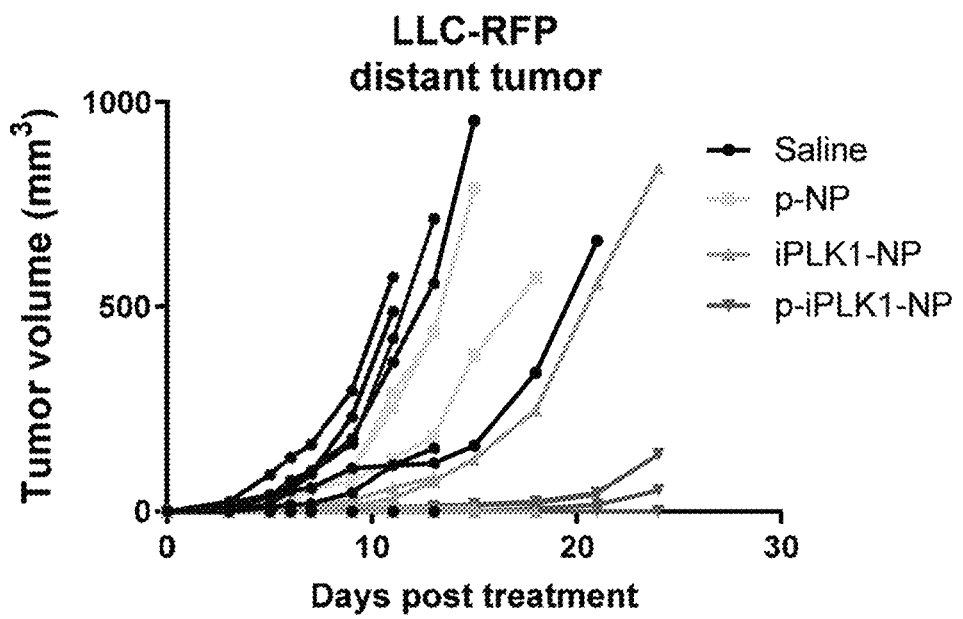
Figure 8D:
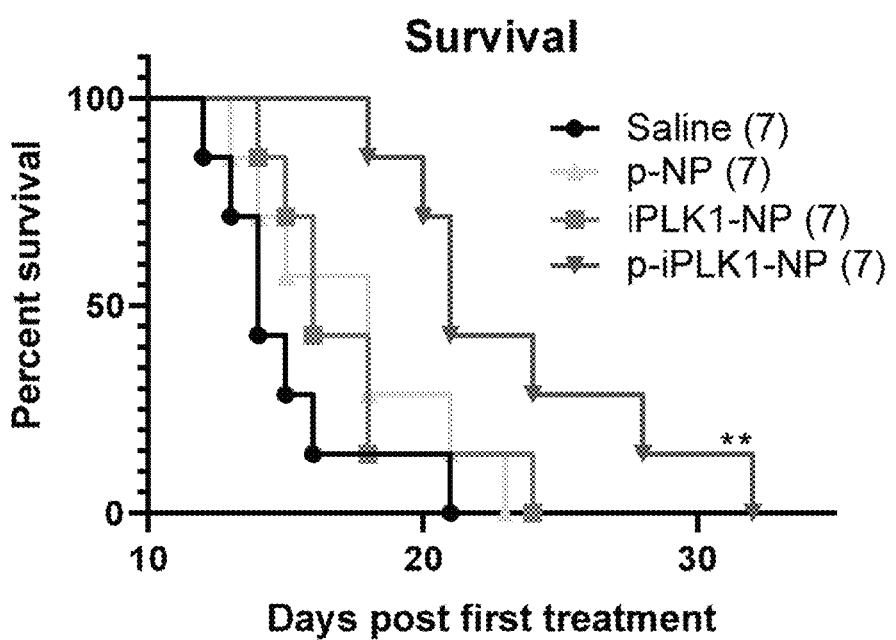
Figure 8E:
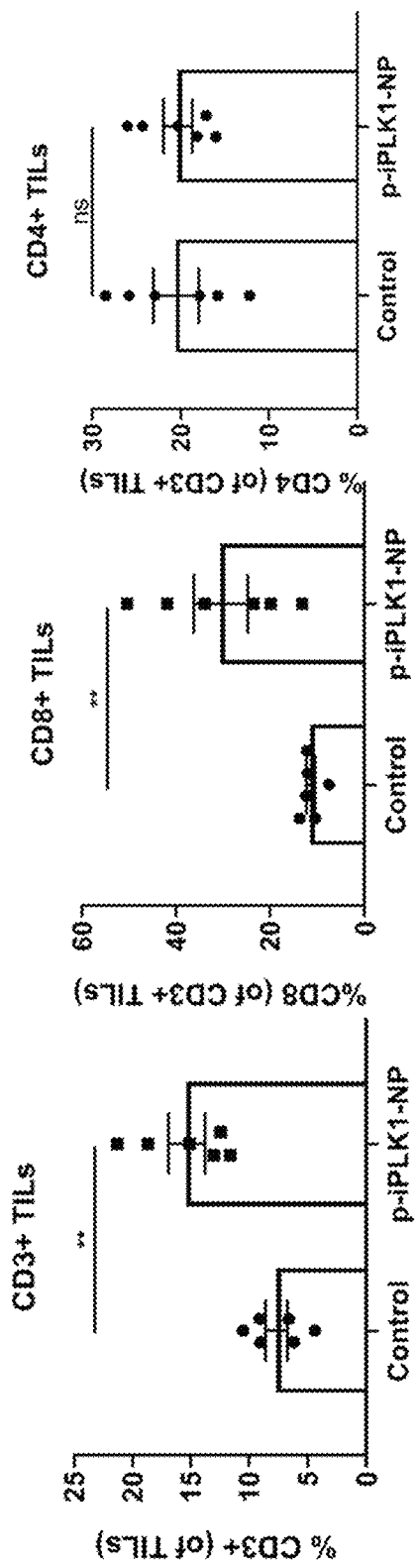

Local Delivery of p-iPLK1-NP Reduces Local and Distant Tumor Growth:

To assess the anti-tumor immune response of p-iPLK1-NP, we utilized a bilateral flank tumor model. C57BL/6 mice were injected with 100K and 40K LLC-JSP cells on the right and left flank, respectively. At day 12 post injection, the right flank (local) tumors were injected with PBS, p-NP, iPLK1-NP, or p-iPLK1-NP (0.5 mg NP, 2.5 µg iPLK1, 20 µg PD-L1) every 3 days for a total of 3 injections (FIG. 8A). Tumor growth of local (treated) and distant (untreated) tumors were monitored. Treatments with p-iPLK1-NP significantly reduced tumor growth of local tumor compared with nanoparticle containing a single drug (p-NP or iPLK1-NP) (FIG. 8B). Importantly, a delay in the onset of distant tumors was also observed for p-iPLK1-NP treated mice (FIG. 8C), which illustrates that an anti-tumor immune response was generated. The antitumor immune effects did not come from PD-L1 on nanoparticle alone but were contributed by both PD-L1 and PLK1 inhibitors on the nanoparticle (FIG. 8C). Furthermore, treatment of p-iPLK1-NP significantly prolonged survival of mice compared with saline control or single drug NPs (FIG. 8D). Additionally, in a separate study, mice were injected with saline or p-iPLK1-NP as illustrated in FIG. 8A and tumors were harvested one day after last treatment to assess T cell infiltration. As shown in FIG. 8E, tumors treated with p-iPLK1-NP had significantly higher CD3+ and CD8+ tumor infiltrating lymphocytes (TILs), while CD4+TILs were not enhanced compared with the control tumors.

Figure 9A:
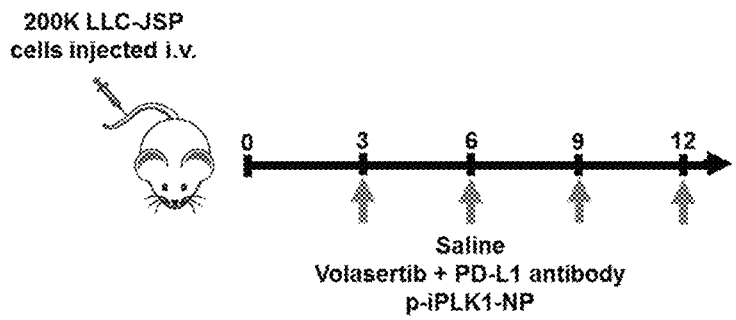
FIGS. 9A-9C. p-iPLK1-NP improves survival of mice bearing metastatic lung tumors.
Figure 9B:
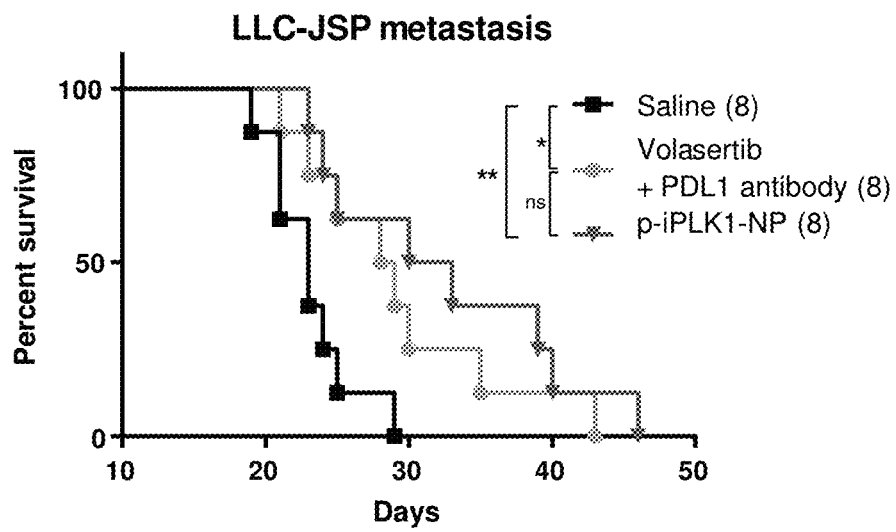
Figure 9C:
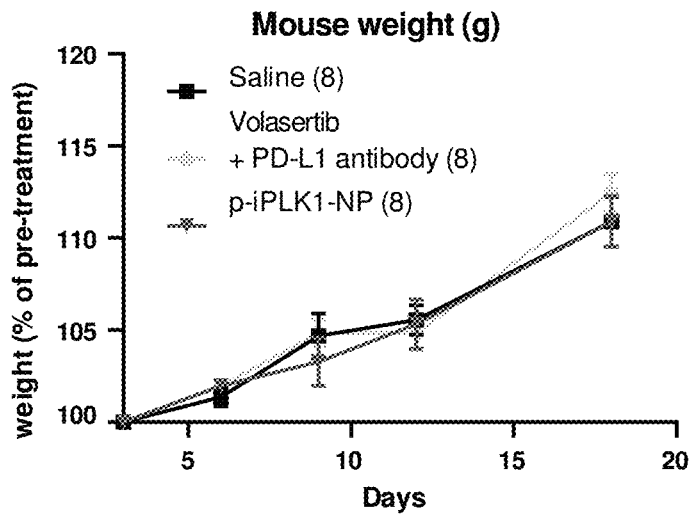

Systemic Administration of p-iPLK1-NP Prolongs Survival of Mice with Experimental Metastatic Tumors:

To demonstrate the clinical potential of p-iPLK1-NP for lung cancer, we developed an experimental metastatic lung tumor model by intravenous injection of LLC-JSP cells (200K cells). Three days post cell injection, mice were randomly grouped and treated with saline, p-iPLK1-NP, or free drugs (volasertib+PD-L1 antibody) every 3 days for 4 doses total, as shown in FIG. 9A. The free drugs were administered at 5-fold higher dose than the amounts on NP. Mice treated with p-iPLK1-NP survived significantly longer than those treated with saline (FIG. 9B). The presence of lung tumor was confirmed visually for each deceased mouse. Data indicate that p-iPLK1-NP was as effective as the free drugs administered at 5-fold higher dose owing to the ability of nanoparticles for tumor targeting and co-localizing the therapeutic effects as well as triggering adaptive antitumor immunity. Furthermore, treatment with p-iPLK1-NP did not cause any weight loss, demonstrating the safety of the construct (FIG. 9C). Systemic applications of the therapeutic construct allow the treatment of other cancers that are not applicable for local delivery.

Figure 10:
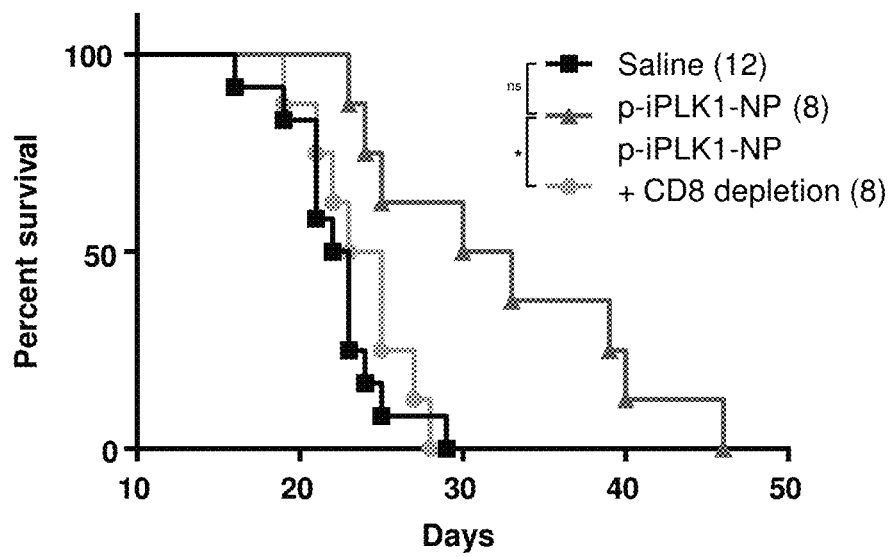
FIG. 10. Efficacy of p-iPLK1-NP is dependent on CD8+ T cells. C57BL/6 mice were injected with 200K LLC-JSP cells intravenously. After 3 days, mice were treated with saline, p-iPLK1-NP (i.v., containing 2.5 µg volasertib and 20 µg PD-L1), or p-iPLK1-NP+anti-CD8 (200 µg twice weekly). (A) Kaplan-Meier Survival curve. *P<0.05, P<0.01, *P<0.001 (Log-rank Mantel-Cox test).

Systemic Administration of p-iPLK1-NP is Dependent on CD8+ T Cells:

C57BL/6 mice were injected with 200K LLC-JSP cells intravenously. After 3 days, mice were treated with saline, p-iPLK1-NP (i.v., containing 2.5 µg volasertib and 20 µg PD-L1 antibody), or p-iPLK1-NP+anti-CD8 (200 µg twice weekly). As shown in FIG. 10, the efficacy of p-iPLK1-NP was immune-mediated as CD8 depletion abolished the effects of p-iPLK1-NP and prolonged survival was not observed (saline vs. p-iPLK1-NP+anti-CD8 antibody; p>0.05=ns). Immune mediated response supersedes direct drug effect with this specific nanoconstruct.

Feed-Forward (Positive Feedback Loop) Delivery and Specificity of Anti-PD-L1 Conjugated NP.

Figure 11A:
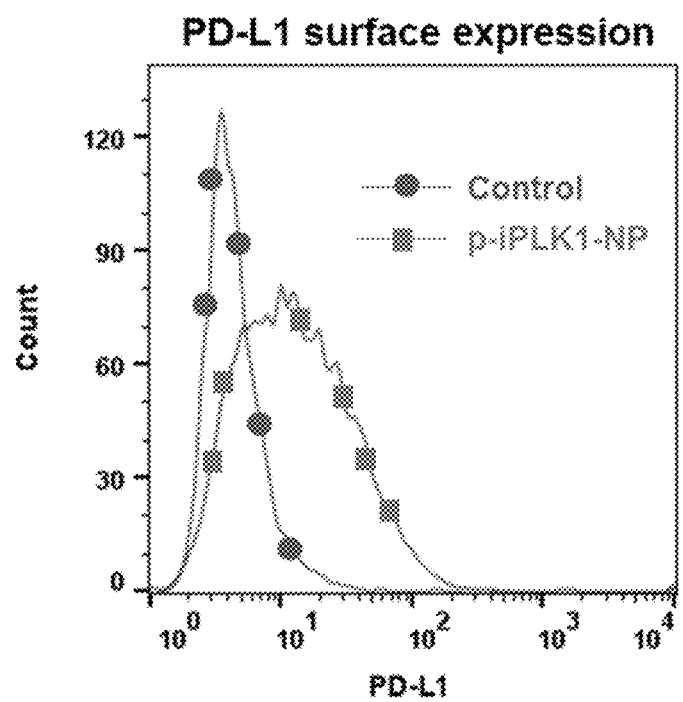
FIGS. 11A-11C. Targeting and treatment specificity of p-iPLK1-NP.
Figure 11B:
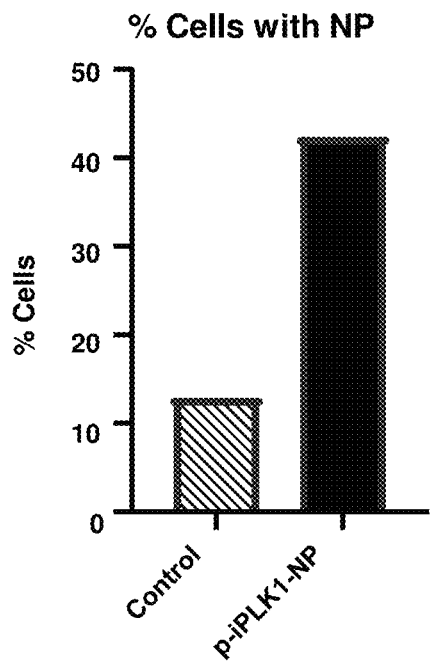
Figure 11C:
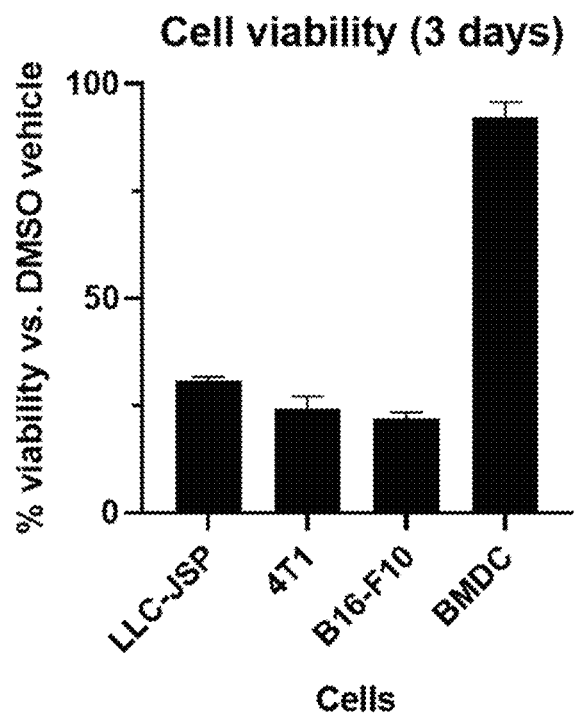

While p-iPLK1-NP initially reduces PD-L1 levels upon binding and internalization (as shown in FIG. 7D-E), surviving cells have upregulated PD-L1 level (FIG. 6D) due to the signaling effects of PLK1 inhibition. In this context, unregulated PD-L1 is used as the homing target for subsequent delivery of p-iPLK1-NP, leading to cancer targeting in a feedforward manner (i.e., higher targeting as increased doses of the treatment until all cancer is gone). To investigate the feedforward targeting of p-iPLK1-NP, we used 4T1 murine cancer cells which express low baseline PD-L1 levels. p-iPLK1-NP led to the upregulation of PD-L1 in 4T1 cells 4 days post treatment (FIG. 11A). We then assessed the cellular uptake of p-iPLK1-NP in control (with low PD-L1) and p-iPLK1-NP-treated 4T1 cells (with upregulated PD-L1). As shown in FIG. 11B, after 1 hour of exposure, p-iPLK1-NP was preferentially taken up by the PD-L1 high cells vs. PD-L1 low cells by nearly 4-fold, demonstrating the selectivity and feed-forward targeting by p-iPLK1-NP. We also evaluated the cell killing selectivity by comparing viability of various cancer cells (lung LLC-JSP, breast 4T1, melanoma B16-F10 cancer cells) vs. bone marrow-derived dendritic cells (BMDC) after treatment with p-iPLK1-NP. As shown in FIG. 11C, p-iPLK1-NP led to significant cell killing in cancer cells but minimal killing in dendritic cells, needed for antigen presentation to develop anti-tumor T cells. Inhibition of mitotic kinases such as PLK1 (e.g., with siRNA, FIG. 12A) also reduced phosphorylation of STAT3, thus would be beneficial to modulating immunosuppressive environment of tumors.

DISCUSSION

In this example, it is shown that inhibition of PLK1 and other mitotic kinases Aurora Kinase A and CHK1 results in an increase of immune checkpoint PD-L1 expression in human and mouse NSCLC cells. This suggests that avoiding the immune response is a mechanism exploited by cancer cells that survive mitotic kinase inhibition.

Figure 12A:
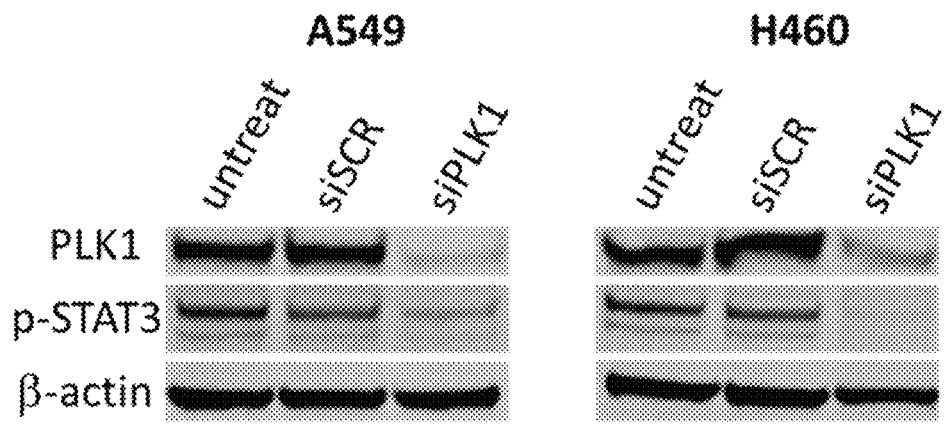
FIGS. 12A and 12B. Inhibition of PLK1 reduces phosphorylation of STAT3.
Figure 12B:
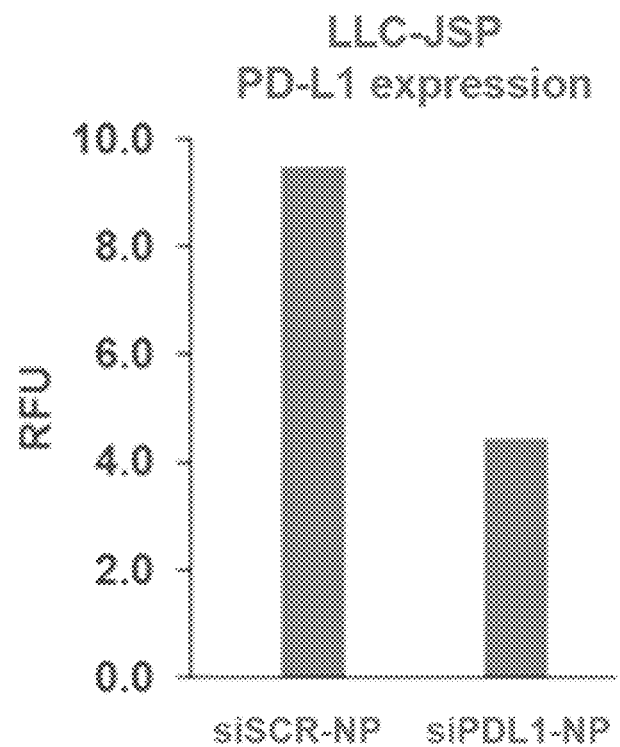

Previous studies have also shown roles of PLK1 in regards to immunity. For instance, PLK1 has been shown to be a regulator of STAT3 activation (Zhang et al., Gastroenterology, 142(3): 521-30.e3, 2012), which promotes an immune suppressive microenvironment, and inhibiting PLK1 resulted in loss of phosphorylated STAT3 in NSCLC cells (Yan et al., Oncology Letters, 16(5): 6801-7, 2018) and as reported herein (FIG. 12A). Further, PLK1 was found to associate with the MAVS and negatively controls its activity in inducing type I interferons (Gringhuis et al., Nature Immunology, 18(2): 225-35, 2017; Vitour et al., J Biological Chemistry, 284(33): 21797-809, 2009). Intriguingly, PLK1 inhibition has also been shown to significantly increase HLA mRNA which encode MHC class I protein, the antigen presenting surface receptors (Li et al., Journal of Oncology, 2018: 3979527, 2018). These studies suggest that PLK1 inhibition may be promising to augment immunotherapy. However, to the best of our knowledge, this is the first study to report the effectiveness of the combination of PLK1 inhibition with immunotherapy.

PLK1 inhibition induces PD-L1 upregulation and co-delivery of PD-L1 antibodies and PLK1 inhibitors significantly enhance the treatment outcome as shown in for NSCLC. Other cytotoxic agents have also been shown to increase PD-L1 expression, including paclitaxel in ovarian cancer (Peng et al., Cancer Research, 75(23): 5034-45, 2015), CDK4/6 inhibitors (Zhang et al., Nature, 553(7686): 91-5, 2018), and PARP inhibitors (Jiao et al., Clin Cancer Res, 23(14): 3711-20, 2017) in breast cancer. Therefore, it is logical that these drugs are now in clinical investigations in combination with PD-L1 checkpoint blockade (Esteva et al., The Lancet Oncology, 20(3): e175-e86, 2019). Our findings also suggest that these and other cytotoxic agents can be combined with PD-L1 immune checkpoint blockade on our nanoparticles to facilitate effective therapy and reduce toxicity in clinics.

The research presented in this example focused on lung cancer, the leading cancer killer (American Cancer Society, Cancer Facts & Figures. 2018). Like melanoma, where immunotherapy has been the most promising, lung cancer is a disease with a high mutational load which drives the expression of various neo-epitopes which can be recognized by host immune system (Campbell et al., Nature Genetics, 48(6): 607-16, 2016; Rizvi et al., Science, 348(6230): 124-8, 2015). Consequently, immunotherapy is a promising approach to treat lung cancer. However, objective response rates are much lower for lung cancer patients than melanoma. The research described here illustrates how superior responses can be achieved for lung cancers when combining PLK1 inhibition with PD-L1 blockade. Further, as the increase of PD-L1 is not specific to PLK1 inhibitors, other cytotoxic agents that induce upregulation of PD-L1 can be explored to synergize with current immune checkpoint blockade agents. Additionally, by co-localizing therapeutic effects with our MSNP platform, the dose of the drugs required can be reduced by 5-fold. This suggests that nanoparticles can improve efficacy and reduce systemic toxicities of free drugs. This is key to improving outcomes as current combination therapy strategies with immune checkpoint blockade can lead to higher rates of adverse events. Lastly, due to the versatility of the MSNP platform, siRNA can also be loaded to target any gene identified as a regulator of cancer progression or immune evasion, in addition to the targeting antibody (e.g. PD-L1) and PLK1 inhibitor.

Example 2: Adjuvant Oligonucleotides to Enhance Therapeutic Construct Function

Figure 13:
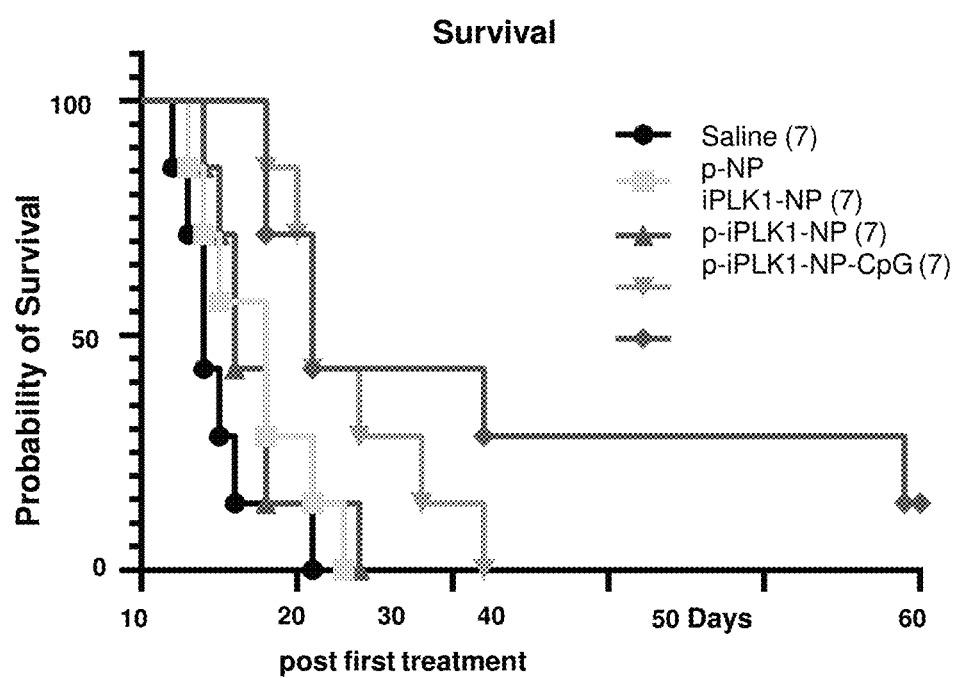
FIG. 13. Adding CpG to p-iPLK1-NP enhances therapeutic benefit as demonstrated by Kaplan Meier Survival curve. 100K LLC-JSP cells were injected in right flank and 40K cells were injected in left flank of C57BL/6 mice. On day 12 post tumor inoculation, mice received intratumoral treatments of saline, p-NP, iPLK1-NP, p-iPLK1-NP, or p-iPLK1-NP-CpG to the right (local) tumor. 0.5 mg NP (2.5 µg iPLK1, 20 µg PD-L1 antibody, 20 µg CpG) in 50 µl was administered every 3 days for a total of 3 doses.

Adjuvant oligonucleotides can also be incorporated to enhance anti-tumor immunity. For instance, incorporation of CpG on p-iPLK1-NP (referred to as p-iPLK1-NP-CpG) significantly improved survival of 2 out of 7 mice, and one mouse was completely free of tumors (FIG. 13). CpG oligodeoxynucleotides act as a danger associated molecular pattern (DAMP) to stimulate PRR, specifically the toll-like receptor 9 (TLR9). This serves as a danger signal for the activation of antigen presenting cells and subsequent priming of T cells. Thus, by releasing antigens (via cancer killing by mitotic inhibitor), delivering CpG adjuvant, and blocking immune checkpoints, this therapeutic tackles various strategies by which cancer cells evade the immune response (Patel & Minn, Immunity 48(3):417-433, 2018).

Example 3: Antibody-Drug Conjugate (ADC) of Alisertib and PD-L1 Antibody Lead to Enhance Cell Killing Compared to Free Drug Counterparts Immune checkpoint antibody-mitotic kinase inhibitor ADC is composed of an immune checkpoint antibody, an MKI, and linkers. The antibody serves as the carrier for drugs (MKIs). The linkers can be tailored to get desired ADC's physicochemical properties and pharmacokinetics and to control the drug liberation. The drugs can be release outside or inside targeted cells. If the drug is released inside the targeted cells, the antibody also serves as the targeting moiety to enhance the drug uptake into cells. The drug-to-antibody ratio may range from 1 to 20. Ideal ratio (e.g., about 2 to 8 or about 4 to 6) should yield best pharmacokinetics and tumor accumulation, as well as highest antitumor activities.

Materials and Methods.

The synthesis of PD-L1-alisertib contained 3 steps. (1) Alisertib-PEG conjugation, (2) PD-L1 activation, and (3) PD-L1-alisertib conjugation. (1): 0.3 ml of 5 mg/ml alisertib (Selleck Chemicals, USA) in dimethyl sulfoxide (DMSO) (Fisher Scientific, USA) was mixed with 50 µl of 60 mg/ml (1-ethyl-3-(3-dimethylaminopropyl)carbodiimide hydrochloride (Thermo Scientific, USA) in DMSO and 27 µl of d60 mg/ml N-hydroxysuccinimide (Sigma Aldrich, USA) in DMSO. After that, 57.8 µl of 40 mg/ml H2N-PEG-SH (MW 400) (Nanocs, USA) in DMSO was added. The reactant mixture was purged with N2 for 1 minute and then stirred at room temperature for 12 hours. Distilled water was then added to precipitate alisertib-PEG-SH. Alisertib-PEG-SH was collected by centrifuge at 15,000 rpm, 4° C. for 10 minutes and washed 3 times with distilled water. The final clean alisertib-PEG-SH was lyophilized (AdVantage 2.0, SP Scientific, USA) for long term storage. (2): 0.147 ml of 6.76 mg/ml PD-L1 (BioXCell, USA) was mixed with 0.9 ml of phosphate buffer saline (PBS) (pH 7.2) and 29 µl of 5 mg/ml sulfosuccinimidyl 4-(N-maleimidomethyl)cyclohexane-1-carboxylate (sulfo-SMCC) (Thermo Fisher, USA) solution in water. The reactant mixture was stirred at room temperature for 1 hour. The pure PD-L1-SMCC was collected by using a desalting column (Thermo Fisher, USA). (3): 750 μg of PD-L1-SMCC and 70 μg of alisertib-PEG-SH were dissolved in a mixture of PBS (pH 7.2) (1 ml), DMSO (50 μl), and propylene glycol (50 μl). The reactant mixture was purged with N2 for 1 minute and then stirred at room temperature for 24 hours. The PD-L1-alisertib solution was collected by a desalting column and then lyophilized. The drug-to-antibody ratio was determined by UV absorbance at 280 nm and 318 nm.

Figure 14A:
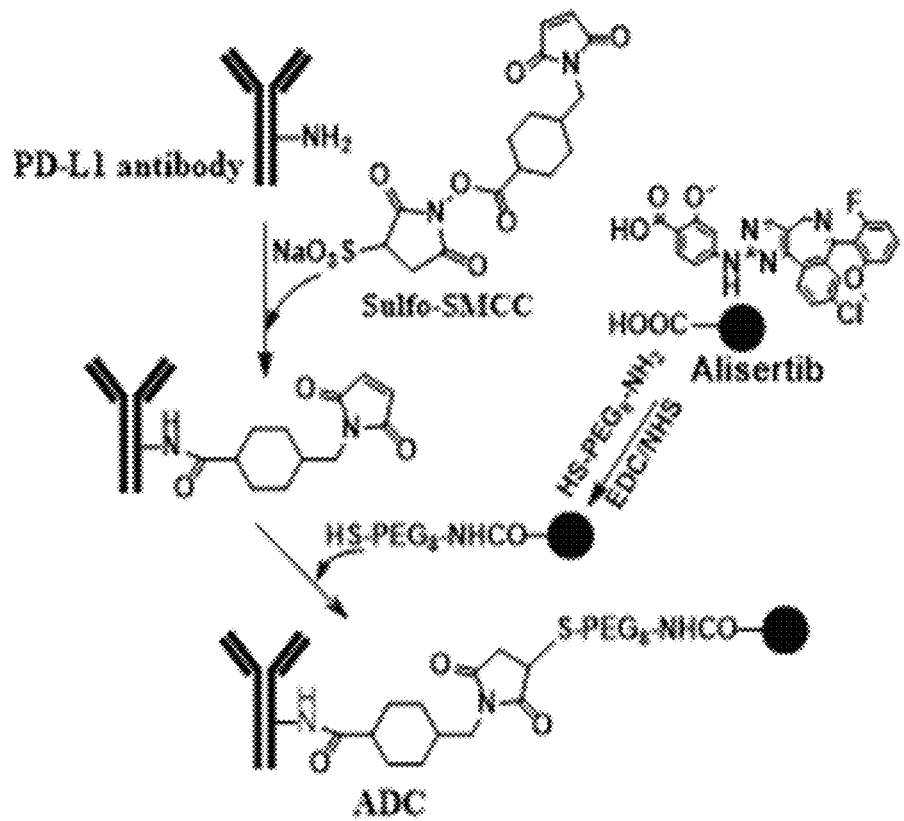
FIGS. 14A-14C. Antibody-drug conjugate (ADC) of alisertib (Aurora Kinase A inhibitor) and PD-L1 antibody.
Figure 14B:
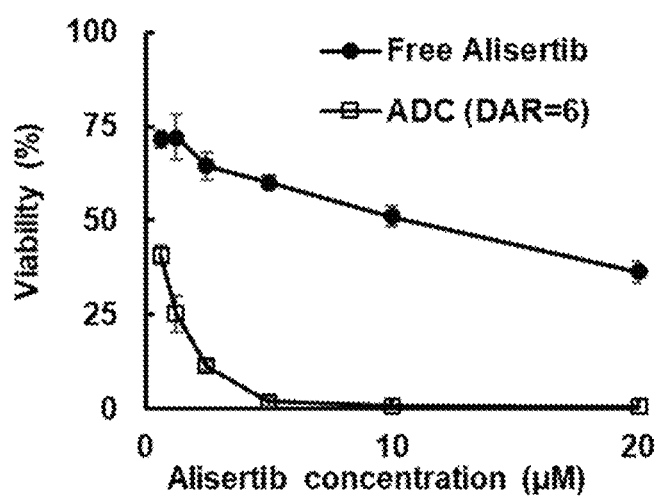
Figure 14C:
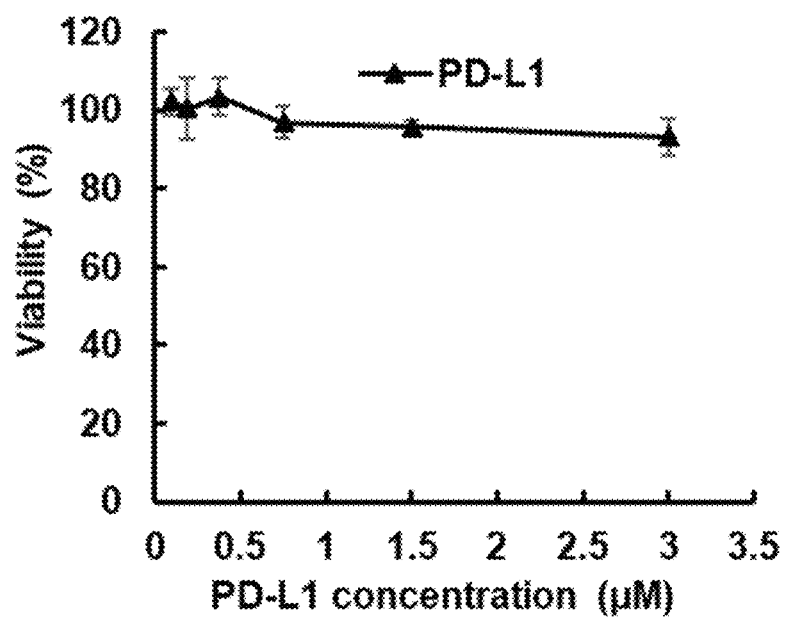

Results:

We have prepared PD-L1 antibody-alisertib conjugates using N-(maleimidomethyl) cyclohexane-1-carboxylate (MCC) linker used in an FDA-approved ADC drug (Kadcyla or T-DM1). MCC linker is not cleavable, but, before conjugation to antibody-MCC, alisertib was modified with a short PEG chain via —HN—CO— bond (FIG. 14A). This amide bond could be hydrolyzed by acidic conditions in endosomes and lysosomes, releasing alisertib intact. The short $PEG_8$ (MW 400 Da) was used to enhance the solubility of alisertib and introduce a thiol group for conjugation with antibody-MCC. Desalting columns were used for removing free alisertib and thiolated alisertib. The drug-to-antibody ratio (DAR) was 6 alisertib molecules per antibody (determined by UV-Vis). The ADC had significantly greater cytotoxicity in LLC-JSP cells when compared to free alisertib (FIG. 14B), while free PD-L1 did not have any effects on the cell viability (FIG. 14C).

Example 4: Topical Formulation and Application of Therapeutic Construct

The therapeutic constructs disclosed herein can be formulated into topical formulations. Several vehicles known in the art can be mixed with the construct, e.g., Aquaphor (ointment-based) and Carbopol (gel-based). Heat or surfactant (e.g., Polysorbate 80 (Tween 80) as an emulsifier) can be used to allow better mixing of the vehicle and an aqueous suspension of AIRISE. As an example, it was confirmed that 10 wt. % Tween-80 did not cause any premature leakage of siRNA from the nanoparticle. It was also shown that 2.5 wt. % Tween-80 was sufficient to enhance the mixing of siRNA-NP and Aquaphor upon warming the mixture to 55° C.

Methods to enhance penetration simultaneously can be used, such as ultrasound and microneedle rollers (e.g., Dermaroller® with the needle height ranging from 0.5 mm to 1.5 mm). Application of microneedles with needle height as short as 0.5 mm can enhance penetration of topical siRNA-nanoparticle formulation when tested in pig skin (FIG. 15) and in mice (FIG. 16).

Figure 15:
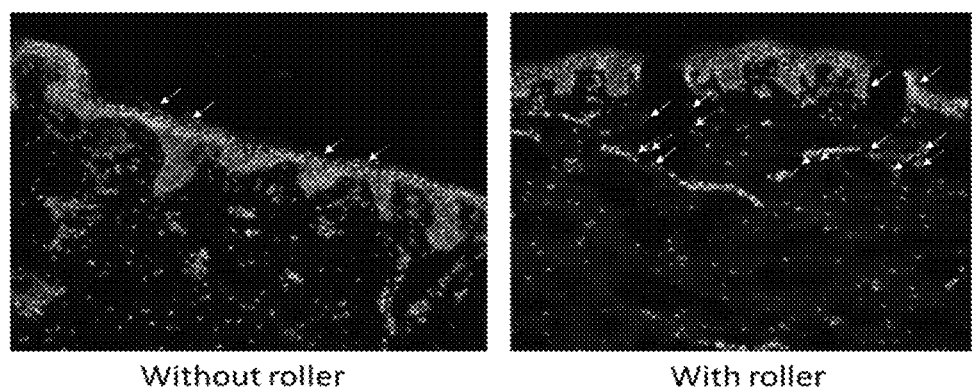
FIG. 15. Topical siRNA-NP in pig skin with and without microneedle roller pre-treatment. Fluorescent images of pig skin treated with one topical application of Dy677-siSCR-NP in Aquaphor for one hour with and without pre-treating skin with a microneedle roller. siRNA signal is noted with arrows. Tissues were also stained for nuclei with Hoechst 33342.

FIG. 15 shows that microneedle roller enhances penetration of siRNA nanoparticle construct when tested in pig skin, which is similar in thickness to human skin. Pig skins were incubated with the formulation (Dy677-siSCR-NP in Aquaphor) for 1.5 h (37° C.; 5% CO2). After 1.5 hours, a skin punch was taken from the treated area and processed for fluorescent imaging using a standard approach. Significant enhancement in skin penetration with a microneedle roller was observed. While siRNA signal (arrows) was confined to the outer surface of the pig skin when siRNA-NP in Aquaphor was given without a roller, we observed siRNA signal (arrows) past the epidermis down to the dermis layer with microneedle pre-application (FIG. 15).

Figure 16:
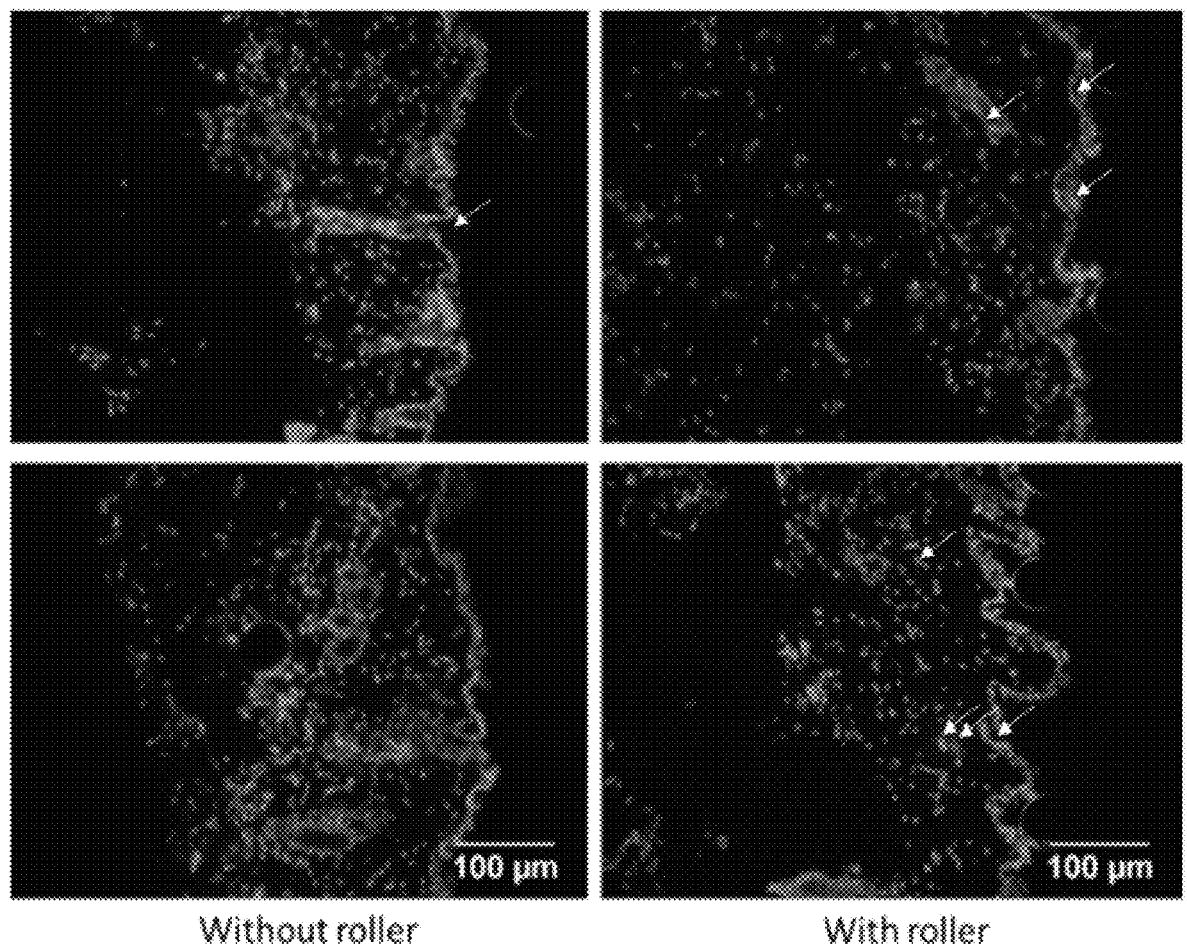
FIG. 16. Topical siRNA-NP/Tween-Aquaphor in mice with and without microneedle roller pre-treatment. Fluorescent images of mouse skin treated with one topical application of Dy677-siSCR-NP in Tween/Aquaphor for 1.5 hour with and without pre-treating skin with a microneedle roller. siRNA signal is noted with arrows. Tissues were also stained for nuclei with Hoechst 33342.

FIG. 16 shows that microneedle roller enhances topical delivery of siRNA-NP. First, mice were shaved one day before treatment. Dy677-siSCR-NP (0.72 nmol siRNA) was mixed with 100 μL of 2.5% Tween-Aquaphor (per one application). Right before treatment, a dermal microroller was applied to only one side of the back in four directions consistently, while the other side was not pre-treated. The mixture was applied to the shaved area (approximately 2 $cm^2$ application area) with and without microneedle pre-treatments for comparison. After 1.5 hr of treatment time, treated skin samples were harvested and processed for imaging.

Figure 17A:
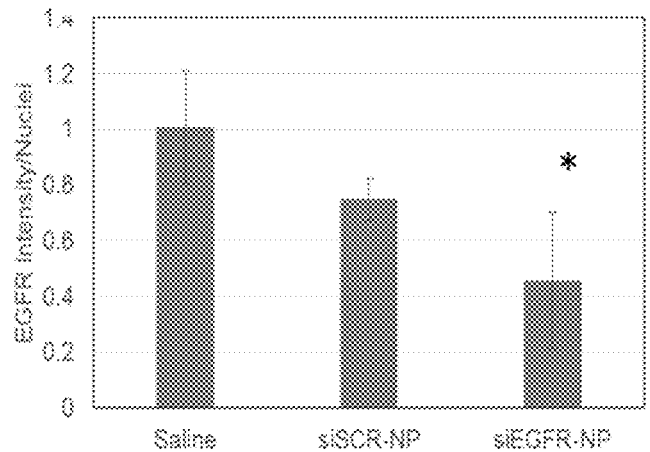
FIGS. 17A and 17B. EGFR knock down efficacy of topical siRNA-NP with microneedle roller versus injected siRNA-NP. Mouse skin was harvested at 3 days after one topical treatment with siEGFR-NP or siSCR-NP in Tween/Aquaphor with microneedle roller application (FIG. 17A) or 3 days after one injection of siEGFR-NP or siSCR-NP in saline (FIG. 17B). Skin tissue was fixed and stained with fluorescently labelled EGFR antibody for EGFR signal quantification. 4-8 images (20λ) were processed per condition and 3 animals per group.
Figure 17B:
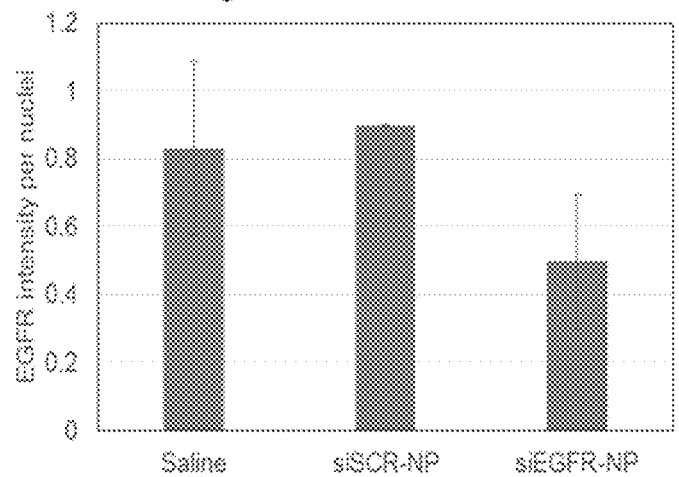
Figure 18:
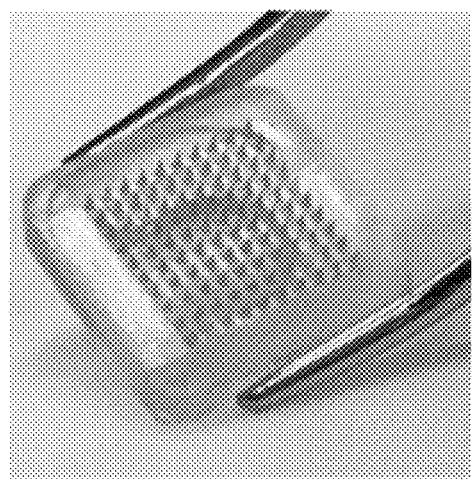
FIG. 18. Dextran-based microneedle containing NP loaded with Dy677-siRNA.

FIGS. 17A-17B show the resulting gene knockdown at 3 days after microroller+topical siRNA nanoconstruct application. A 55% EGFR knockdown in siEGFR-NP versus saline treated group (*p<0.05) (FIG. 17A) was observed. In comparison, one intradermal injection of siEGFR-NP (with same siEGFR dose of 0.72 nmol) resulted in 40% EGFR knock down versus saline treated groups (FIG. 17B). Microneedle form of therapeutic construct. The use of dissolvable microneedles based on dextran, amylopectin, PVP, PEG, methylcellulose, chitosan, or other polymers or compounds known in the arts were explored for microneedle fabrications, as shown in FIG. 18, which allow for painless in-home treatment and are highly effective at delivering AIRISE-02 owing to high needle density (100 needles per 1 $cm^2$). As an example (FIG. 18), a dextran solution (300 mg/ml in water) containing NP loaded with Dy677-conjugated siRNA was cast onto a microneedle mold. The solution was centrifuged or vacuumed to fill the mold compactly. The microneedle was dried by air, desiccator, vacuum oven, fridge, or combination thereof and removed from the mold. Heights of the needles varied from 300 to 800 microns depending on the templates and optimization. siRNA-NP was successfully loaded into these needle arrays (at about 0.5 nmol siRNA per array) and the needles were fully dissolved within 5 min after applying to pig skins. Different dissolving time can be engineered by varying the ingredients of the microneedles. Microneedle patches of different shape and forms can also be manufactured with different templates.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect, in this context, is a measurable reduction in a biological impact (such as an anti-cancer effect) of a therapeutic construct.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A therapeutic construct comprising:
a mesoporous silica nanoparticle comprising (MSNP) platform loaded with: a small molecule Polo-like Kinase (PLK1) inhibitor or a PLK1 siRNA; and
a Programmed Death-Ligand 1 (PD-L1) antibody conjugated onto the MSNP platform: wherein the small molecule PLK1 inhibitor makes up 0.01% to 5% by weight of the therapeutic construct.

2. The therapeutic construct of claim 1, wherein the small molecule PLK1 inhibitor comprises at least one of GSK461364, BI2536, Tak960, NMS-P937, or volasertib.

3. The therapeutic construct of claim 1, wherein the small molecule PLK1 inhibitor comprises volasertib.

4. The therapeutic construct of claim 1, wherein the nanoparticle is coated with cross-linked polyethylenimine (PEI) and polyethylene glycol.

5. The therapeutic construct of claim 1, wherein the PLK1 siRNA makes up 0.1% to 20% by weight of the therapeutic construct.

6. The therapeutic construct of claim 1, wherein the PD-L1 antibody makes up 0.1% to 20% by weight of the therapeutic construct.

7. The therapeutic construct of claim 1, wherein the nanoparticle has a mean particle size of about 30-80 nm.

8. The therapeutic construct of claim 1, having a hydrodynamic size of about 80-200 nm.

9. The therapeutic construct of claim 1, further comprising an adjuvant.

10. The therapeutic construct of claim 9, wherein the adjuvant is a CpG oligonucleotide.

11. The therapeutic construct of claim 10, wherein the adjuvant is CpG ODN 7909.

12. A composition comprising:
the therapeutic construct of claim 1; and
a pharmaceutically acceptable carrier, excipient, or diluent.

13. A method of treating a subject diagnosed as having a hyperproliferative disease or condition, comprising administering to the subject an effective amount of the composition of claim 12.

14. The method of claim 13, wherein the subject is a mammal.

15. The method of claim 14, wherein the mammal is a human.

16. The method of claim 15, wherein the hyperproliferative disease comprises one or more of cancer, precancer, or cancer metastasis.

17. The method of claim 16, wherein the hyperproliferative disease comprises one or more of melanoma, lung cancer, breast cancer, pancreatic cancer, brain cancer, prostate cancer, head and neck cancer, kidney cancer, colorectal cancer, lymphoma, colon cancer, or liver cancer.

18. The method of claim 17, wherein administering comprises one or more of:
injection to or at a tumor in the subject;
infusion locally to or at a tumor in the subject;
systemic injection in the subject;
systemic infusion in the subject;
oral administration to the subject; or
topical application to the subject.

19. The method of claim 17, wherein administering comprises:
intravenous injection; or
intratumoral injection.

20. The method of claim 17, further comprising administering to the subject an anti-cancer therapy comprising an anti-cancer agent or any form of radiation therapy.

21. A therapeutic construct comprising:
a mesoporous silica nanoparticle (MSNP) platform comprising 0.01% to 5% mitotic kinase inhibitor, by weight of the therapeutic construct; and
an antibody against PD-L1 conjugated onto the MSNP platform.

22. The therapeutic construct of claim 12, wherein the mitotic kinase inhibitor comprises at least one of volasertib, alisertib, or AZD7762.

23. The therapeutic construct of claim 12, wherein the nanoparticle is coated with cross-linked polyethylenimine and polyethylene glycol.

24. The therapeutic construct of claim 21, wherein the PD-L1 antibody makes up 0.1% to 20% by weight of the therapeutic construct.

25. The therapeutic construct of claim 21, wherein the nanoparticle has a mean particle size of about 30-80 nm.

26. The therapeutic construct of claim 12, having a hydrodynamic size of about 80-200 nm.

27. The therapeutic construct of claim 21, further comprising an adjuvant.

28. The therapeutic construct of claim 27, wherein the adjuvant is a CpG oligonucleotide.

29. The therapeutic construct of claim 28, wherein the adjuvant is CpG ODN 7909.

30. A composition comprising:
the therapeutic construct of claim 21; and
a pharmaceutically acceptable carrier, excipient, or diluent.

31. A method of treating a subject diagnosed as having a hyperproliferative disease or condition, comprising administering to the subject an effective amount of the composition of claim 30.

32. The method of claim 31, wherein the subject is a mammal.

33. The method of claim 32, wherein the mammal is a human.

34. The method of claim 33, wherein the hyperproliferative disease comprises one or more of cancer, precancer, or cancer metastasis.

35. The method of claim 34, wherein the hyperproliferative disease comprises one or more of melanoma, lung cancer, breast cancer, pancreatic cancer, brain cancer, prostate cancer, head and neck cancer, kidney cancer, colorectal cancer, lymphoma, colon cancer, or liver cancer.

36. The method of claim 35, wherein administering comprises one or more of:
injection to or at a tumor in the subject;
infusion locally to or at a tumor in the subject;
systemic injection in the subject;
systemic infusion in the subject;
oral administration to the subject; or
topical application to the subject.

37. The method of claim 35, wherein administering comprises:
intravenous injection; or
intratumoral injection.

38. The method of claim 35, further comprising administering to the subject an anti-cancer therapy comprising an anti-cancer agent or any form of radiation therapy.

39. A therapeutic construct comprising:
a mesoporous silica nanoparticle (MSNP) platform comprising PLK1 siRNA; and
an antibody against PD-L1 conjugated onto the MSNP platform.

40. The therapeutic construct of claim 39, wherein the MSNP platform comprises 0.1% to 20% PLK1 siRNA, by weight of the therapeutic construct.

41. The therapeutic construct of claim 39, wherein the MSNP platform comprises 2-4% PLK1 siRNA, by weight of the therapeutic construct.

42. The therapeutic construct of claim 39, wherein the nanoparticle is coated with cross-linked polyethylenimine and polyethylene glycol.

43. A composition comprising:
the therapeutic construct of claim 39; and
a pharmaceutically acceptable carrier, excipient, or diluent.

44. A method of treating a subject diagnosed as having a hyperproliferative disease or condition, comprising administering to the subject an effective amount of the composition of claim 43.

45. The method of claim 44, wherein the subject is a mammal.

46. The method of claim 45, wherein the mammal is a human.

47. The method of claim 46, wherein the hyperproliferative disease comprises one or more of cancer, precancer, or cancer metastasis.

48. The method of claim 47, wherein the hyperproliferative disease comprises one or more of melanoma, lung cancer, breast cancer, pancreatic cancer, brain cancer, prostate cancer, head and neck cancer, kidney cancer, colorectal cancer, lymphoma, colon cancer, or liver cancer.

49. The method of claim 48, wherein administering comprises one or more of:
injection to or at a tumor in the subject;
infusion locally to or at a tumor in the subject;
systemic injection in the subject;
systemic infusion in the subject;
oral administration to the subject; or
topical application to the subject.

50. The method of claim 49, wherein administering comprises:
intravenous injection; or
intratumoral injection.

51. The method of claim 50, further comprising administering to the subject an anti-cancer therapy comprising an anti-cancer agent or any form of radiation therapy.

* * * * *